United States Patent
Kusik et al.

(10) Patent No.: US 10,758,180 B2
(45) Date of Patent: *Sep. 1, 2020

(54) METHOD FOR IMPROVING PSYCHOPHYSIOLOGICAL FUNCTION FOR PERFORMANCE UNDER STRESS

(71) Applicant: Biofeedback Systems Design, LLC, Carlisle, MA (US)

(72) Inventors: Daniel A. Kusik, Carlisle, MA (US); Dejan Stankovic, Medford, MA (US); Andrew M. Bourhis, San Rafael, CA (US)

(73) Assignee: Biofeedback Systems Design, LLC, Carlisle, MA (US)

( * ) Notice: Subject to any disclaimer, the term of this patent is extended or adjusted under 35 U.S.C. 154(b) by 618 days.

This patent is subject to a terminal disclaimer.

(21) Appl. No.: 15/614,076

(22) Filed: Jun. 5, 2017

(65) Prior Publication Data
US 2017/0265805 A1    Sep. 21, 2017

Related U.S. Application Data

(60) Continuation of application No. 15/202,894, filed on Jul. 6, 2016, now Pat. No. 9,668,693, which is a
(Continued)

(51) Int. Cl.
*A61B 5/00* (2006.01)
*A61M 21/02* (2006.01)
(Continued)

(52) U.S. Cl.
CPC .......... *A61B 5/4884* (2013.01); *A61B 5/0022* (2013.01); *A61B 5/02* (2013.01);
(Continued)

(58) Field of Classification Search
CPC ....... A61B 5/165; A61B 5/167; A61B 5/0002; A61B 5/486; A61B 5/4076; A61B 5/4035; A61B 2505/09; A61B 5/4884
(Continued)

(56) References Cited

U.S. PATENT DOCUMENTS

| 3,821,949 A | 7/1974 | Hartzell et al. |
| 4,573,472 A | 3/1986 | Ito |

(Continued)

FOREIGN PATENT DOCUMENTS

| EP | 0 208 007 A1 | 1/1987 |
| EP | 1 156 851 B1 | 11/2001 |

(Continued)

OTHER PUBLICATIONS

Blanchard et al., "The Effects of Thermal Biofeedback and Autogenic Training of Cardiovascular Reactivity: The Joint USSR-USA Behavioral Hypertension Treatment Project," Boifeedback and Self-Regulation, vol. 13, No. 1, pp. 25-38, (1988).
(Continued)

*Primary Examiner* — John P Lacyk
(74) *Attorney, Agent, or Firm* — Sunstein LLP

(57) ABSTRACT

A method of improving psychophysiological function of a subject performing a stress-inducing activity using a computer includes, after a plurality of sensors that monitor stress-indicating physiological parameters have been coupled to the subject and to the computer, providing, by the computer to the subject, a set of training segments that each present the subject with one or more visual, audible, or tactile prompts, wherein in at least one of the training segments, the prompts induce the subject to simultaneously perform both the stress-inducing activity and a relaxation-inducing protocol. The computer provides the set of training segments until a value of at least one physiological param-
(Continued)

eter that indicates stress in the subject is within a pre-defined range of a baseline value of the parameter, thereby indicating that the subject has successfully performed the stress-inducing activity while maintaining alertness with a relative minimum of stress.

21 Claims, 43 Drawing Sheets

Related U.S. Application Data continuation of application No. 14/823,662, filed on Aug. 11, 2015, now Pat. No. 9,402,581, which is a division of application No. 14/309,497, filed on Jun. 19, 2014, now Pat. No. 9,138,558.

(51) Int. Cl.

| | |
|---|---|
| A61B 5/02 | (2006.01) |
| G06F 19/00 | (2018.01) |
| A61B 5/16 | (2006.01) |
| G16H 40/63 | (2018.01) |
| G16H 50/20 | (2018.01) |
| A61B 5/0205 | (2006.01) |
| G09B 19/00 | (2006.01) |
| A61M 21/00 | (2006.01) |
| A61B 5/021 | (2006.01) |
| A61B 5/053 | (2006.01) |
| A61B 5/08 | (2006.01) |

(52) U.S. Cl.
CPC .......... *A61B 5/02055* (2013.01); *A61B 5/165* (2013.01); *A61B 5/4035* (2013.01); *A61B 5/486* (2013.01); *A61B 5/4836* (2013.01); *A61B 5/742* (2013.01); *A61M 21/02* (2013.01); *G06F 19/34* (2013.01); *G06F 19/3481* (2013.01); *G09B 19/00* (2013.01); *G16H 40/63* (2018.01); *G16H 50/20* (2018.01); *A61B 5/021* (2013.01); *A61B 5/0531* (2013.01); *A61B 5/0816* (2013.01); *A61M 2021/005* (2013.01); *A61M 2021/0022* (2013.01); *A61M 2021/0027* (2013.01); *A61M 2021/0088* (2013.01); *A61M 2205/3584* (2013.01); *A61M 2230/04* (2013.01); *A61M 2230/42* (2013.01); *A61M 2230/65* (2013.01)

(58) Field of Classification Search
USPC .................................................. 600/300, 301
See application file for complete search history.

(56) References Cited

U.S. PATENT DOCUMENTS

| | | | |
|---|---|---|---|
| 4,984,158 A | 1/1991 | Hillsman | |
| 5,007,430 A | 4/1991 | Dardik | |
| 5,267,942 A | 12/1993 | Saperston | |
| 5,368,042 A | 11/1994 | O'Neal et al. | |
| 5,377,100 A | 12/1994 | Pope et al. | |
| 5,406,957 A | 4/1995 | Tansey | |
| 5,694,939 A | 12/1997 | Cowings | |
| 6,097,981 A | 8/2000 | Freer | |
| 6,293,904 B1 | 9/2001 | Blazey et al. | |
| 6,540,663 B1 | 4/2003 | Vau et al. | |
| 6,554,763 B1 | 4/2003 | Amano et al. | |
| 6,836,681 B2 | 12/2004 | Stabler et al. | |
| 7,150,715 B2 | 12/2006 | Collura et al. | |
| 8,062,129 B2 | 11/2011 | Pope et al. | |
| 8,328,420 B2 | 12/2012 | Abreu | |
| 9,138,558 B1 | 9/2015 | Kusik et al. | |
| 9,402,581 B2* | 8/2016 | Kusik | A61B 5/486 |
| 9,668,693 B2* | 6/2017 | Kusik | A61B 5/486 |
| 2003/0009087 A1 | 1/2003 | Keirsbilck | |
| 2004/0133082 A1 | 7/2004 | Abraham-Fuchs et al. | |
| 2005/0096555 A1 | 5/2005 | Elliott | |
| 2005/0124851 A1 | 6/2005 | Patton et al. | |
| 2005/0131273 A1 | 6/2005 | Asano et al. | |
| 2005/0154264 A1 | 7/2005 | Lecompte et al. | |
| 2006/0022214 A1 | 2/2006 | Morgan et al. | |
| 2006/0057549 A1 | 3/2006 | Prinzel, III et al. | |
| 2007/0056582 A1 | 3/2007 | Wood et al. | |
| 2007/0056594 A1 | 3/2007 | El-Nokaly et al. | |
| 2007/0123756 A1 | 5/2007 | Kitajima et al. | |
| 2008/0071137 A1 | 3/2008 | Schachter et al. | |
| 2008/0171914 A1 | 7/2008 | Ouwerkerk et al. | |
| 2008/0214903 A1* | 9/2008 | Orbach | A61B 5/486 |
| | | | 600/301 |
| 2008/0221401 A1 | 9/2008 | Derchak et al. | |
| 2009/0082685 A1 | 3/2009 | Stabler et al. | |
| 2009/0105605 A1 | 4/2009 | Abreu | |
| 2009/0137915 A1 | 5/2009 | Childre et al. | |
| 2010/0022852 A1 | 1/2010 | Westerink et al. | |
| 2011/0015468 A1 | 1/2011 | Aarts et al. | |
| 2011/0066005 A1 | 3/2011 | Rotenberg | |
| 2011/0105859 A1 | 5/2011 | Popovic et al. | |
| 2012/0116176 A1 | 5/2012 | Moravec et al. | |
| 2012/0289789 A1 | 11/2012 | Jain et al. | |
| 2013/0089851 A1 | 4/2013 | Drane et al. | |

FOREIGN PATENT DOCUMENTS

| | | |
|---|---|---|
| EP | 1 269 910 A2 | 1/2003 |
| WO | WO 2006/011076 A1 | 2/2006 |
| WO | WO 2006/082565 A1 | 8/2006 |
| WO | WO 2006/090371 A2 | 8/2006 |
| WO | WO 2008/099320 A1 | 8/2008 |
| WO | WO 2008/147958 A1 | 12/2008 |
| WO | WO 2009/112983 A1 | 9/2009 |
| WO | WO 2009/136307 A1 | 11/2009 |
| WO | WO 2009/144502 A1 | 12/2009 |
| WO | WO 2010/104480 A1 | 9/2010 |
| WO | WO 2010/124247 A2 | 10/2010 |
| WO | WO 2012/061707 A2 | 5/2012 |

OTHER PUBLICATIONS

Cowings et al., "Autogenic-Feedback Training (AFT) as a Preventive Method for Space Motion Sickness: Background and Experimental Design," NASA Technical Memorandum 108780, 20 pages, (Aug. 1993).
Cowings et al., "Autogenic-Feedback Training Exercise is Superior to Promethazine for Control of Motion Sickness Symptoms," Journal of Clinical Pharmacology, vol. 40, pp. 1154-1165, (2000).
Hjortskov et al. "The Effect of Mental Stress on Heart Rate Variability and Blood Pressure During Computer Work," European Journal of Applied Physiology, vol. 92, pp. 84-89, (Feb. 27, 2004).
Kober et al. "Learning to Modulate One's Own Brain Activity: The Effect of Spontaneous Mental Strategies," Frontiers in Human Neuroscience, vol. 7, Article 695, 12 pages, (Oct. 18, 2013).
McCraty, "Enhancing Emotional, Social, and Academic Learning With Heart Rhythm Coherence Feedback," Biofeedback, pp. 130-134, (Winter 2005).
McCraty et al., "The Coherent Heart Heart-Brain Interactions, Psychophysiological Coherence, and the Emergence of System-Wide Order," Integral Review, vol. 5, No. 2, 106 pages, (Dec. 2009).
Miu et al. "Reduced Heart Rate Variability and Vagal Tone in Anxiety: Trait Versus State, and the Effects of Autogenic Training," Autonomic Neuroscience: Basic and Clinical, vol. 145, pp. 99-103, (2009).
Stout et al., "Reliability of Psychophysiological Responses Across Multiple Motion Sickness Stimulation Tests," Journal of Vestibular Research, vol. 5, No. 1, pp. 25-33, (1995).
International Searching Authority, International Search Report—International Application No. PCT/US2015/036476, dated Sep. 18,

(56) References Cited

OTHER PUBLICATIONS 2015, together with the Written Opinion of the International Searching Authority, 14 pages.

* cited by examiner

Stress Profile Test 2: Math Test

1701

1703

13 * 24 =

| 1 | 2 | 3 |
| 4 | 5 | 6 |
| 7 | 8 | 9 |
|   | 0 |   |

Enter

1707

1705
- Question 1 ☒
- Question 2 ☐
- Question 3 ☒
- Question 4 ☒
- Question 5 ☒
- Question 6 ☒
- Question 7 ☐
- Question 8 ☐
- Question 9 ☒
- Question 10 ☐
- Question 11 ☐
- Question 12 ☐
- Question 13 ☐
- Question 14 ☐
- Question 15 ☐
- Question 16 ☐
- Question 17 ☐
- Question 18 ☐
- Question 19 ☐
- Question 20 ☐

1709 — *Time Remaining: 01:20 (min:sec)*

*Fig. 17*

METHOD FOR IMPROVING PSYCHOPHYSIOLOGICAL FUNCTION FOR PERFORMANCE UNDER STRESS

CROSS-REFERENCE TO RELATED APPLICATIONS

This application is a continuation of prior application Ser. No. 15/202,894, filed Jul. 6, 2016, now U.S. Pat. No. 9,668,693, which is a continuation of prior application Ser. No. 14/823,662, filed Aug. 11, 2015, now U.S. Pat. No. 9,402,581, which is a divisional of prior application Ser. No. 14/309,497, filed Jun. 19, 2014, now U.S. Pat. No. 9,138,558. The contents of these prior Applications are incorporated herein by reference in their entireties.

TECHNICAL FIELD

The present invention relates to psychophysiological function, and more particularly to apparatus and methods for computer-implemented improvement of psychophysiological function.

BACKGROUND ART

It is known in the prior art to measure physiological parameters during training. United States application publication number 2006/0057549 A1 discloses training for attaining a physiological state consistent with the successful performance of a task, wherein the training takes place in the physical environment of the task in question (putting green, tennis court, lacrosse field, etc.) and the training comprises static repetition of the task in the presence of information related to the user's physiological state during iterations of the task.

United States application publication number US2009/0137915 A1, which does not disclose training, does disclose determining the state of overlap between biological systems which exhibit oscillatory behavior such as heart rhythms, respiration, blood pressure waves, low frequency brain waves, based on a determination of heart rate variability (HRV), and an evaluation of the power spectrum thereof.

In addition the following patent publications concern related subject matter: US20100022852A1, US20080214903A1, US20090105605A1, US20030009087A1, US20080171914A1, US20120116176A1, US20090082685A1, and US20110015468A1.

SUMMARY OF THE EMBODIMENTS

In a first embodiment of the invention there is provided a computer-implemented method for improving psychophysiological function for performance of a subject under stress. The method of this embodiment includes:
  after a plurality of sensors that monitor stress-indicating physiological parameters have been coupled to the subject, in a baseline computer process, obtaining from the sensors baseline measurements of a baseline set of stress-indicating physiological parameters and storing the baseline measurements;
  in a stress determination computer process, causing the subject to be exposed to a second plurality of potentially stress-inducing activities while obtaining from the sensors stress-condition measurements of the baseline set of parameters and storing the stress-condition measurements;
  in a relaxation determination computer process, causing the subject to be exposed to a third plurality of potentially relaxation-inducing protocols while obtaining from the sensors relaxation-condition measurements of the baseline set of parameters and storing the relaxation-condition measurements; and
  in a characterization computer process, retrieving the baseline, stress-condition, and relaxation-condition measurements, and using them to identify a selected parameter, which is one of the baseline set of parameters, as particularly indicative of stress and of relaxation in the subject, and with respect to the selected parameter, identifying a selected stress-inducing activity and a selected relaxation-inducing protocol pertinent to the subject, and storing data characterizing the selected set of stress-inducing activities and the selected set of relaxation-inducing protocols pertinent to the subject.

Optionally, the method further includes in a training computer process, providing training in carrying out the selected relaxation-inducing protocol in a manner tending to cause achievement of coherence. In a further related embodiment providing training includes, in a first training segment, exposing the subject to the selected relaxation-inducing protocol alone until there is achieved a targeted level of the selected parameters as to be indicative of coherence in the subject. Optionally, the method further includes in a target determination process, retrieving the baseline, stress-condition, and relaxation-condition measurements, and using the retrieved measurements, together with a set of measurements obtained in the training computer process, to determine the targeted level of the selected parameters, wherein the targeted level is re-determined in the course of each training segment.

In another related embodiment, training further includes, in a second training segment, next exposing the subject to the selected relaxation-inducing protocol in the presence of feedback indicative of the value of the selected parameter until there is achieved the targeted level of the selected parameter as to be indicative of coherence in the subject. Optionally, providing training thereafter includes, in a third training segment, exposing the subject only to feedback indicative of the value of the selected parameter until there is achieved the targeted level of the selected parameter as to be indicative of coherence in the subject. As a further option, providing training thereafter includes, in a fourth training segment, exposing the subject to the selected relaxation-inducing protocol in the presence of (i) feedback indicative of the value of the selected set of parameters and (ii) prompts presenting the selected set of stress-inducing activities, until there is achieved the targeted level of the selected set of parameters as to be indicative of coherence in the subject.

As yet a further option, providing training thereafter includes, in a fifth training segment, exposing the subject only to (i) feedback indicative of the value of the selected set of parameters and (ii) prompts indicative of the selected set of stress-inducing activities, until there is achieved the targeted level of the selected set of parameters as to be indicative of coherence in the subject. In a still further option, providing training thereafter includes, in a sixth training segment, exposing the subject only to prompts indicative of the selected set of stress-inducing activities until there is achieved the targeted level of the selected set of parameters as to be indicative of coherence in the subject.

In another related embodiment, one of the relaxation-inducing protocols is passive muscle relaxation, and the passive muscle relaxation is structured in a manner tending to cause achievement of coherence. In another related embodiment, one of the relaxation-inducing protocols is autogenics, and the autogenics is structured in a manner tending to cause achievement of coherence. In another related embodiment, one of the relaxation-inducing protocols is guided imagery and the guided imagery is structured in a manner tending to cause achievement of coherence. In yet another related embodiment, one of the relaxation-inducing protocols is mindfulness, and the mindfulness is structured in a manner tending to cause achievement of coherence. In another related embodiment, one of the relaxation-inducing protocols is controlled breathing, and the controlled breathing is structured in a manner tending to cause achievement of coherence.

In another embodiment, the invention provides a computer-implemented method for improving psychophysiological function for performance of a subject under stress. The method of this embodiment includes:

after a plurality of sensors that monitor stress-indicating physiological parameters have been coupled to the subject, exposing the subject, using computer processes, to a series of training segments as follows:

in a first training segment, exposing the subject to a relaxation-inducing protocol alone until there is achieved a targeted level of at least one stress-indicating physiological parameter as to be indicative of coherence in the subject;

in a second training segment, next exposing the subject to a relaxation-inducing protocol in the presence of feedback indicative of the value of at least one stress-indicating physiological parameter until there is achieved the targeted level of the at least one parameter as to be indicative of coherence in the subject;

in a third training segment, exposing the subject only to feedback indicative of the value of at least one parameter until there is achieved the targeted level of the at least one parameter as to be indicative of coherence in the subject;

in a fourth training segment, exposing the subject to a relaxation-inducing protocol in the presence of (i) feedback indicative of the value of at least one of the parameters and (ii) prompts presenting at least one of the stress-inducing activities, until there is achieved the targeted level of at least one parameter as to be indicative of coherence in the subject.

in a fifth training segment, exposing the subject only to (i) feedback indicative of the value of at least one of the parameters and (ii) prompts presenting at least one of the stress-inducing activities, until there is achieved the targeted level of at least one parameter as to be indicative of coherence in the subject.

in a sixth training segment, exposing the subject only to prompts indicative of at least one of stress-inducing activities until there is achieved the targeted level of at least one parameter as to be indicative of coherence in the subject.

Optionally, using computer processes further includes, in a target determination process, using a set of measurements obtained in the training computer process, to determine the targeted level of the at least one stress-indicating physiological parameter, wherein the targeted level is re-determined in the course of each training segment.

Also optionally, using computer processes further includes, the course of each segment, providing, to the subject, feedback indicative of a degree to which the subject has achieved the targeted level of the at least one parameter as to be indicative of coherence in the subject.

As a further option the feedback includes a visual component, and the visual component is in the form of a virtual race involving virtual objects, wherein a first virtual object represents achievement by the subject in reaching the targeted level of the at least one parameter, and other distinct virtual objects represent distinct amounts of shortfall by the subject in reaching the targeted level of the at least one parameter.

In another embodiment, the invention provides a computer-implemented method for improving psychophysiological function for performance of a subject under stress. The method of this embodiment includes:

after a plurality of sensors that monitor stress-indicating physiological parameters have been coupled to the subject, exposing the subject, using computer processes, to at least one training segment during which is determined a degree to which the subject has achieved a targeted level of least one stress-indicating physiological parameter as to be indicative of coherence in the subject; and providing, to the subject, feedback indicative of the degree to which the subject has achieved the targeted level of the at least one parameter as to be indicative of coherence in the subject.

In a further related embodiment, the feedback includes a visual component, and the visual component is in the form of a virtual race involving virtual objects, wherein a first virtual object represents achievement by the subject in reaching the targeted level of the at least one parameter, and other distinct virtual objects represent distinct amounts of shortfall by the subject in reaching the targeted level of the at least one parameter.

In another embodiment, the invention provides a sensor interface device providing a set of sensor outputs characterizing a set of physiological parameters to a computer running a training program for training to improve psychophysiological function for performance under stress. the apparatus of this embodiment includes:

a microcontroller, including an analog-to-digital converter and a processor;

a set of sensor inputs coupled to the microcontroller; and an output port, coupled to the microcontroller, that is configured to be coupled to the computer;

wherein the processor is running a communication program that handles all communication with the training program and formats incoming data received at the sensor inputs in a manner permitting consumption of that data by the training program, including for purposes of display, storage, and manipulation.

BRIEF DESCRIPTION OF THE DRAWINGS

The foregoing features of embodiments will be more readily understood by reference to the following detailed description, taken with reference to the accompanying drawings, in which:

FIG. 17 is a representation of a screen display associated with a stress-inducing activity (math test) established and monitored by the program of FIG. 13;

Figure 1:
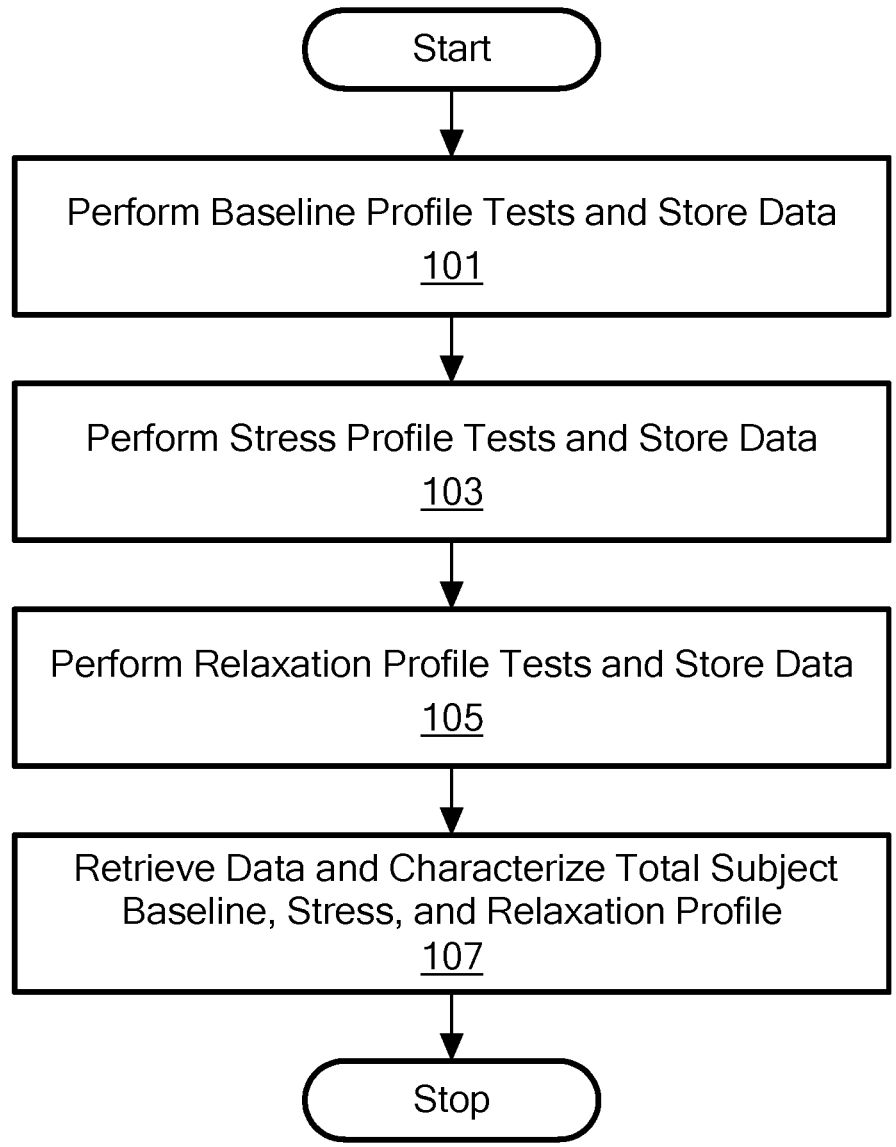
FIG. 1 is a block diagram of logical flow in an embodiment of a method in accordance with the present invention.
Figure 2:
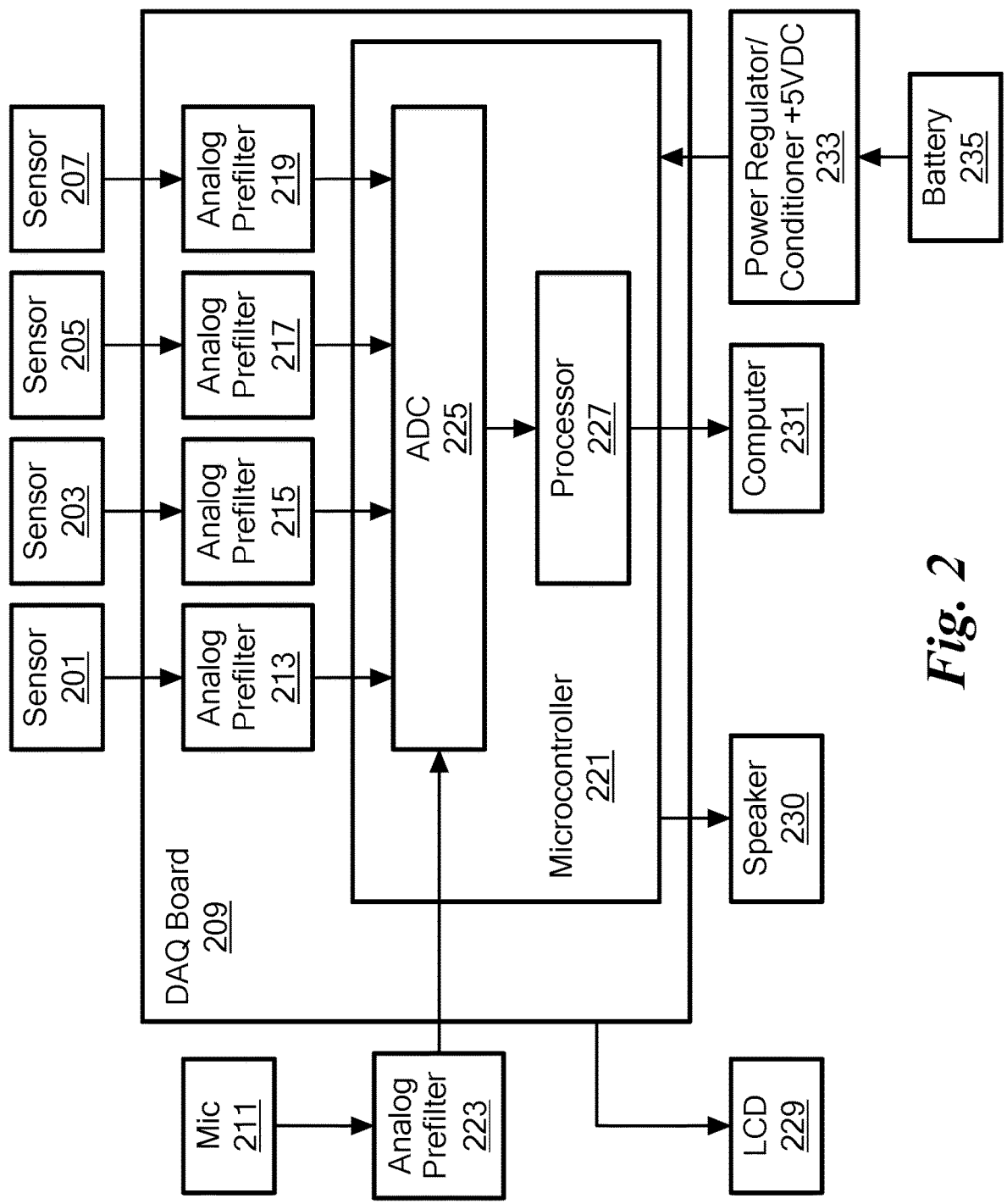
FIG. 2 is block diagram of architecture of a system, in accordance with an embodiment of the present invention, for carrying out the method embodiment of FIG. 1.
Figure 41:
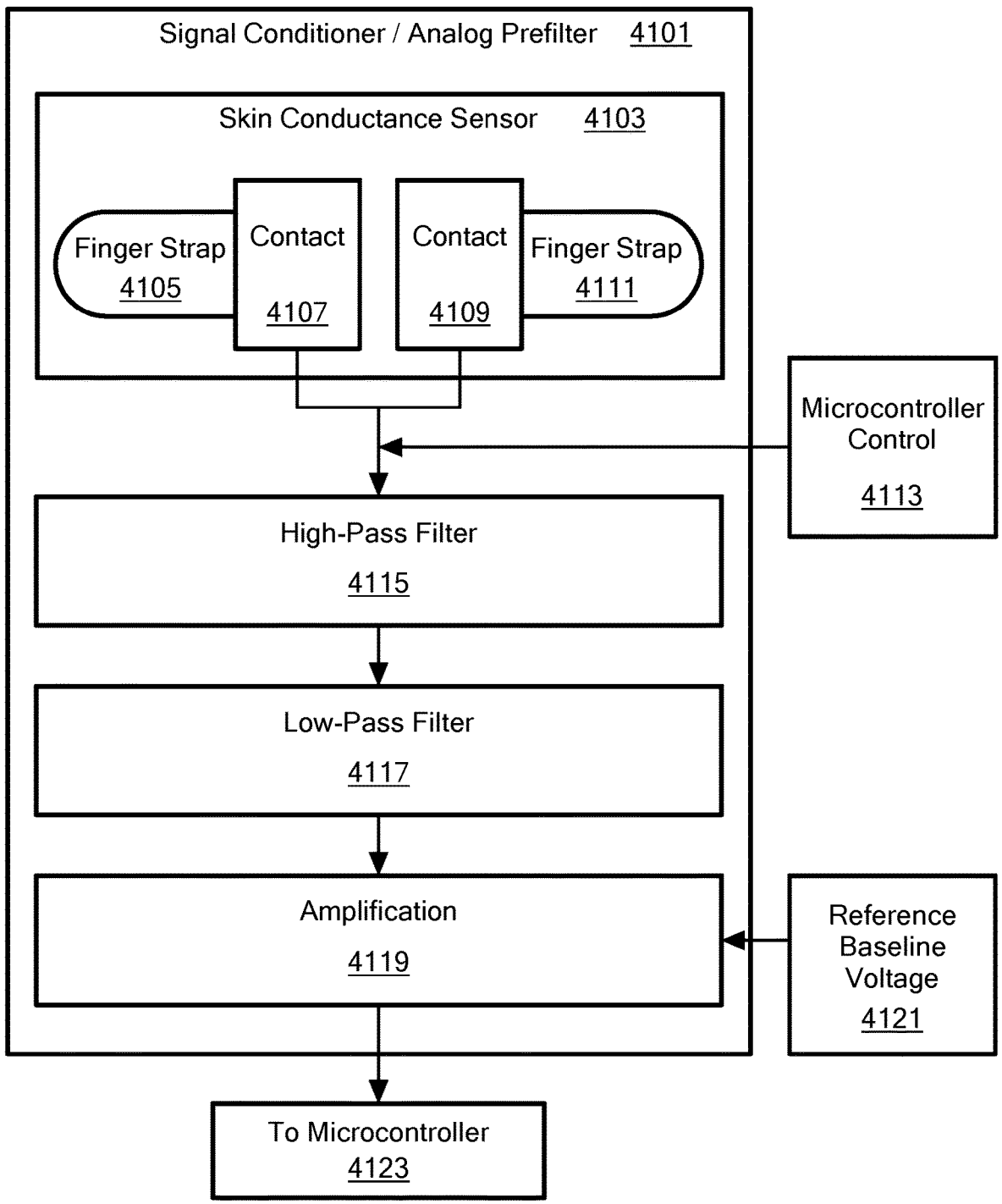
Figure 42:
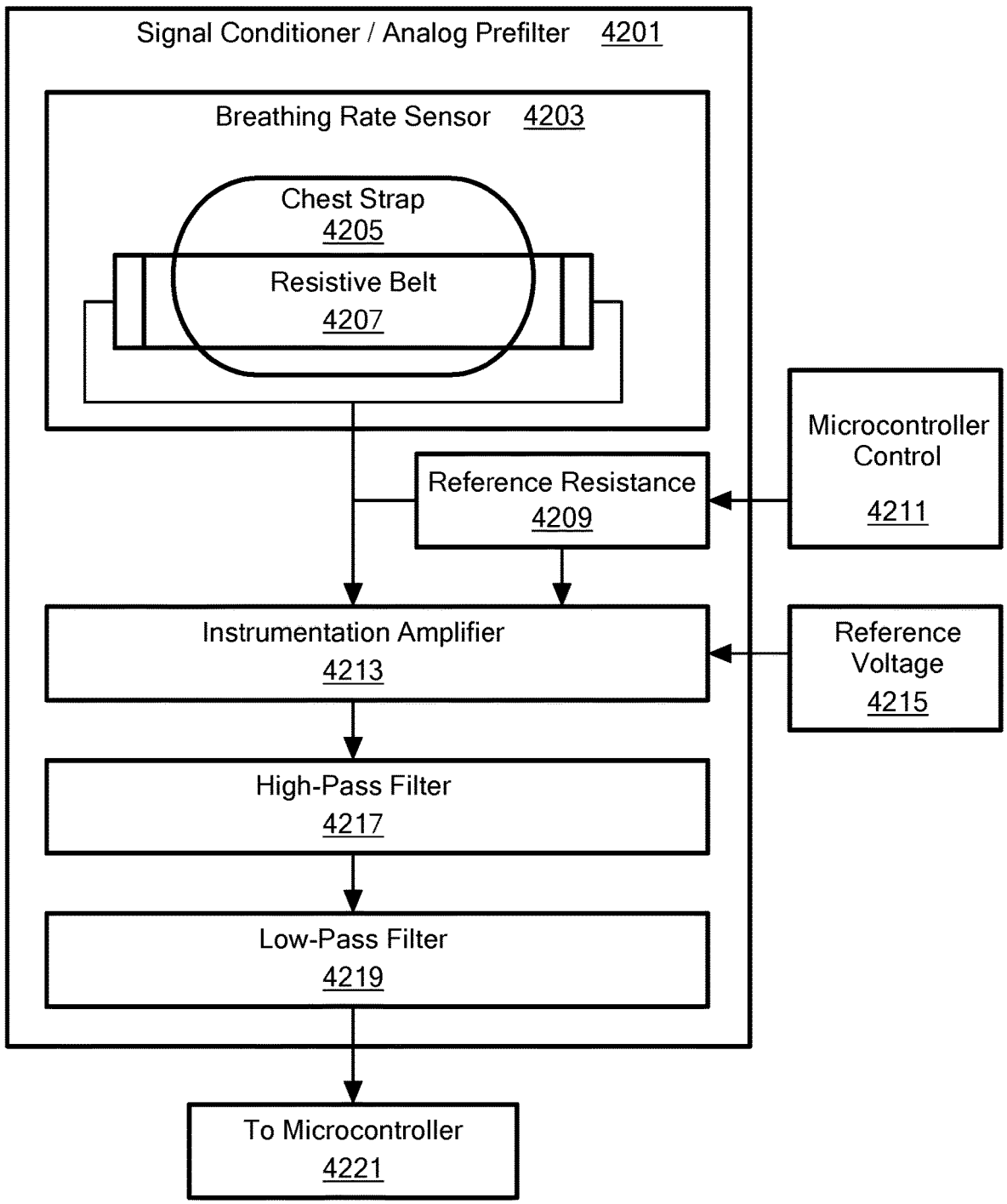
Figure 43:
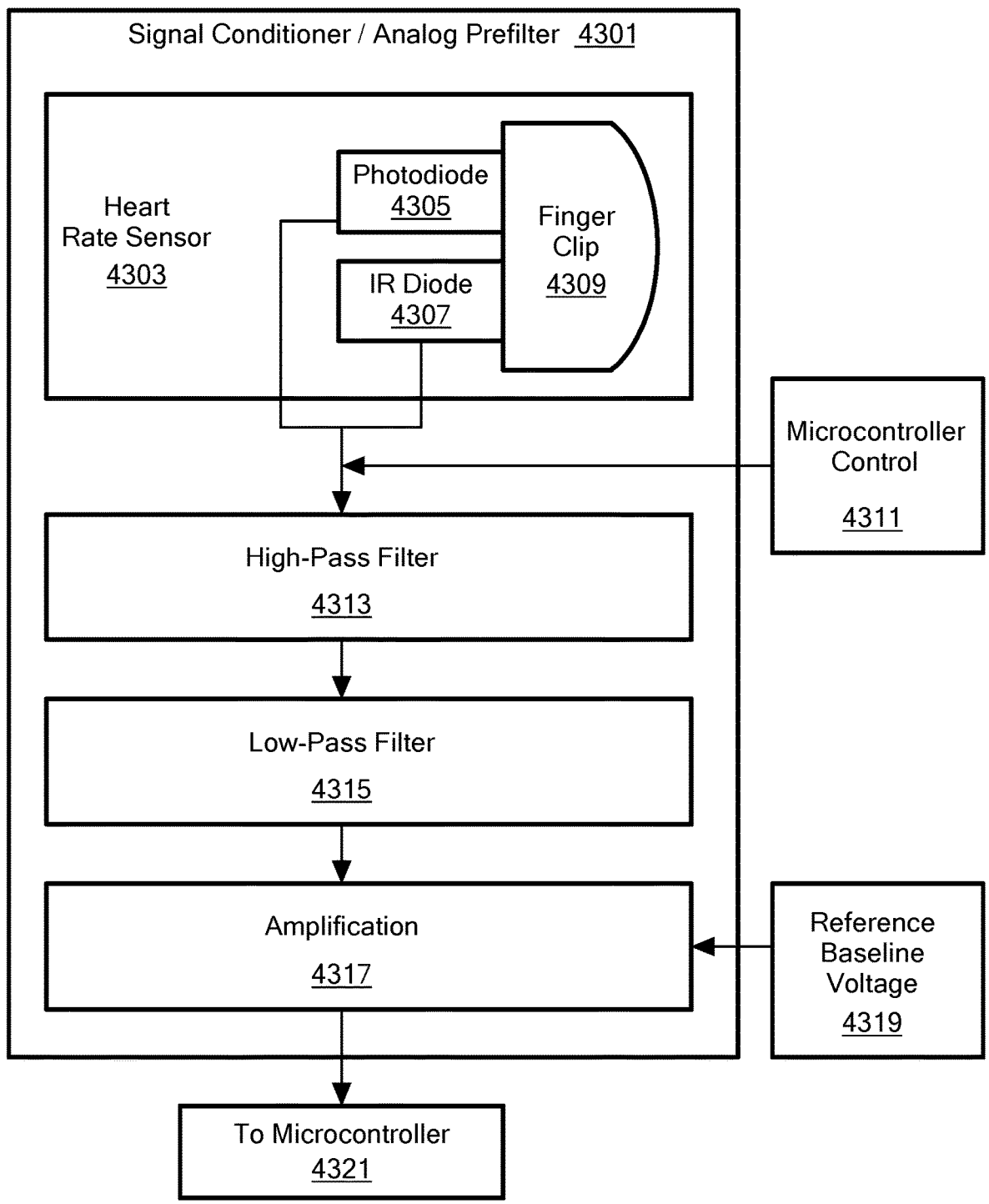
Figure 44:
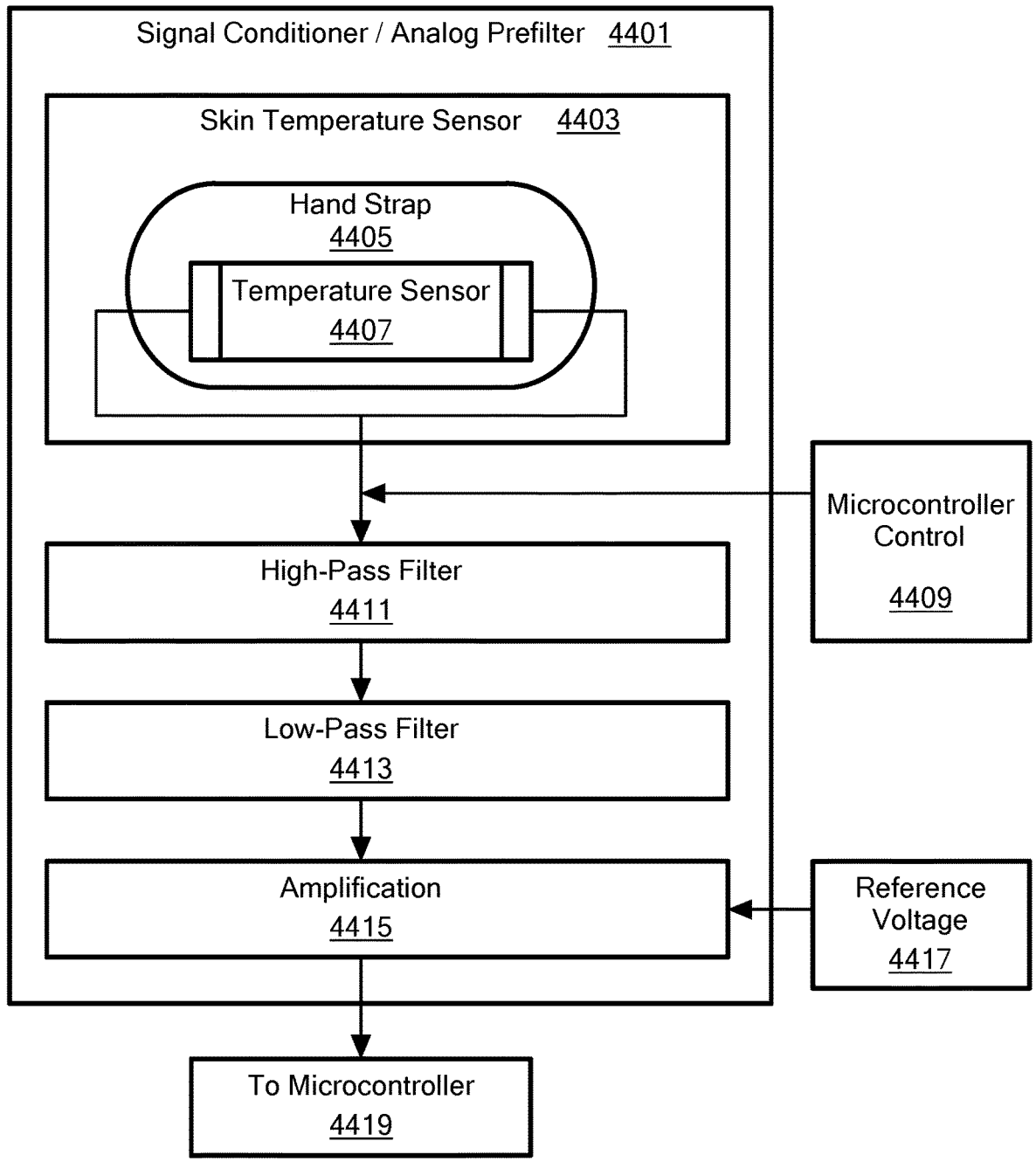

2, in accordance with an embodiment of the present invention, for carrying out the method embodiment of FIG. 1;

FIG. 41 is block diagram of architecture of a skin conductance sensor system associated with the system architecture of FIG. 2, in accordance with an embodiment of the present invention, for carrying out the method embodiment of FIG. 1;

FIG. 42 is block diagram of architecture of a respiration rate sensor system associated with the system architecture of FIG. 2, in accordance with an embodiment of the present invention, for carrying out the method embodiment of FIG. 1;

FIG. 43 is block diagram of architecture of a heart rate sensor system associated with the system architecture of FIG. 2, in accordance with an embodiment of the present invention, for carrying out the method embodiment of FIG. 1; and FIG. 44 is block diagram of architecture of a skin temperature sensor system associated with the system architecture of FIG. 2, in accordance with an embodiment of the present invention, for carrying out the method embodiment of FIG. 1.

DETAILED DESCRIPTION OF SPECIFIC EMBODIMENTS

Definitions. As used in this description and the accompanying claims, the following terms shall have the meanings indicated, unless the context otherwise requires:

The term "stress-indicating physiological parameter" means a physiological parameter, associated with a subject, with respect to which a change in value may be indicative of stress experienced by the subject. Typical stress-indicating physiological parameters are heart rate, respiration rate, skin conductance, skin temperature, muscle tension, and EEG alpha, beta, and delta brain waves.

The term "coherence" of a subject means a state of the subject wherein the subject maintains alertness with a relative minimum of stress.

A "set" has at least one member.

A "stress-inducing activity" is an activity carried out by a subject tending to cause the subject to experience stress.

A "relaxation-inducing protocol" is a series of procedures carried out by a subject tending to cause relaxation in the subject.

"Feedback indicative of the value of a parameter" means information provided, under computer program control, on a recurrent basis to the subject about the value of the parameter. The information may be provided in any of a variety of forms, including visual, audible, and tactile, or combinations of these forms. For example, the information may be provided by visual indication, such as on a display of computer, and can be in the form of text (wherein the parameter value is given, for example, as a number), or a graph (wherein value of the parameter can be shown evolving over time), or a color or other indication based on a mapping between color and parameter value. Alternatively, or in addition, the information may be provided in the form of sound, for example in headphones or a loudspeaker, and the sound may be spoken words characterizing the value of the parameter, or it may be a set of distinct sounds where each member of the set is selected for use depending on the value of the parameter.

A "prompt presenting a stress-inducing activity" means a presentation to the subject, under computer program control, of an activity determined to induce stress in the subject, wherein the presentation may be provided in any of a variety of forms, including visual, audible, and tactile, or combinations of these forms. If the presentation is visual, it may involve, for example, a quiz provided in the form of text on a computer screen. On the other hand, the presentation may be audible, in the form of a quiz provided orally under computer control.

"Feedback indicative of a degree to which the subject has achieved a targeted level of at least one parameter" means information provided, under computer program control, on a recurrent basis to the subject, about the degree to which the subject has achieved the targeted level of the at least one parameter. The information may be provided in any of a variety of forms, including visual, audible, and tactile, or combinations of these forms. For example, the information may be provided by visual indication, such as on a display of computer, and can be in the form of text, or a graph, or a color or other indication based on a mapping between color and parameter value. Alternatively, or in addition, the information may be provided in the form of sound, for example in headphones or a loudspeaker, and the sound may be spoken words, or it may be a set of distinct sounds where each member of the set is selected for use depending on the extent to which the subject has achieved the targeted level of the at least one parameter.

A "computer process" is the performance of a described function in a computer using computer hardware (such as a processor, field-programmable gate array or other electronic combinatorial logic, or similar device), which may be operating under control of software or firmware or a combination of any of these or operating outside control of any of the foregoing. All or part of the described function may be performed by active or passive electronic components, such as transistors or resistors. In using the term "computer process" we do not necessarily require a schedulable entity, or operation of a computer program or a part thereof, although, in some embodiments, a computer process may be implemented by such a schedulable entity, or operation of a computer program or a part thereof. Furthermore, unless the context otherwise requires, a "process" may be implemented using more than one processor or more than one (single- or multi-processor) computer.

Figure 4:
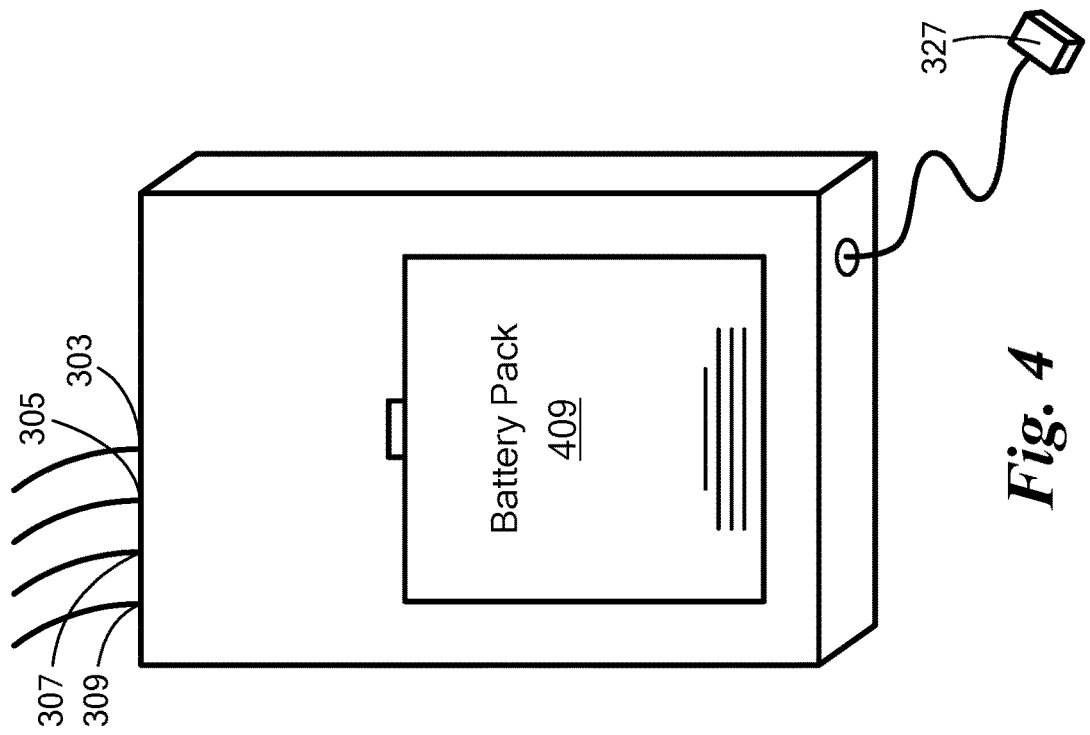
FIG. 4 is a rear perspective view of the sensor interface device of FIG. 3.
Figure 3:
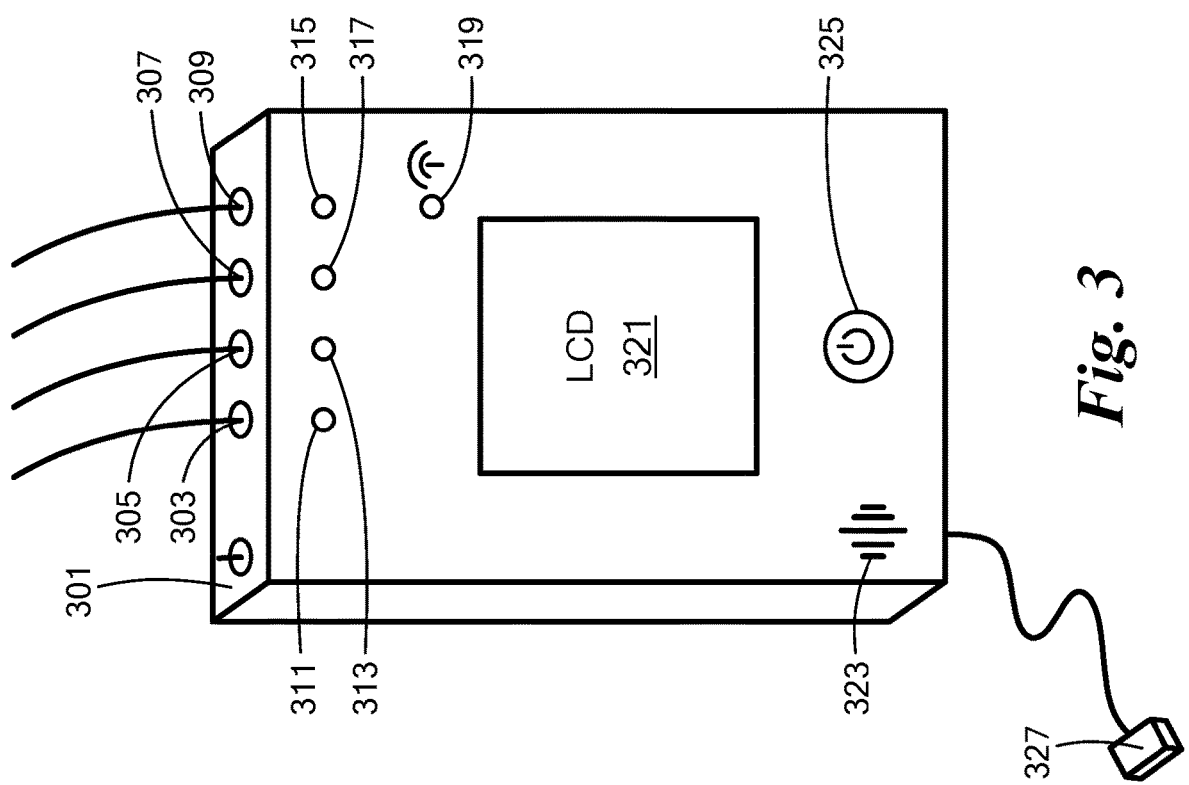
FIG. 3 is a front perspective view of a sensor interface device in accordance with an embodiment of the present invention.

FIG. 1 is a block diagram of logical flow in an embodiment of a method in accordance with the present invention. In accordance with this embodiment, a computer program (sometimes called "the training program"), which is run on a computer operated by the subject, carries out a series of processes. In operation of the embodiment, the sensor interface device described below in connection with FIGS. 2-4 is coupled to the computer, and a set of sensors is coupled to the sensor interface device and to the subject. In process 101, baseline testing of the subject is performed and the data resulting from such baseline testing is stored. In process 103, stress profile testing of the subject is carried out, and the data resulting from such stress profile testing is stored. In process 105, relaxation profile testing of the subject is performed, and the data resulting from such relaxation profile testing is stored. Finally, in process 107, the stored data are retrieved, and the total subject baseline profile, stress profile, and relaxation profile are characterized. As described in more detail below, this characterization permits identification of a parameter that is particularly indicative of stress and of relaxation in the subject. In view of this identification, a set of relaxation-inducing protocols may be developed to train the subject to achieve coherence.

FIG. 2 is block diagram of architecture of a sensor interface device, in accordance with an embodiment of the present invention, for carrying out the method embodiment of FIG. 1. The sensor interface device includes a data acquisition (DAQ) board 209 that has a set of analog prefilters 213, 215, 217, and 219, and a microcontroller 221. The microcontroller 221 includes a processor 227 and an analog-to-digital converter 225, and provides a sensor data output to a user computer 231. Each of four different sensors 201, 203, 205, and 207, is coupled to the analog-to-digital converter 225 through a corresponding analog prefilter 213, 215, 217, and 219. The microcontroller 221 is coupled to user computer 231, and the coupling may, for example, be over a USB link or wirelessly using a Bluetooth protocol. The DAQ board 209 and its components may be powered by a battery 235 through a power regulator/conditioner 233, or by the user computer 231 via the USB link. Similarly, a microphone 211 is coupled to the analog-to-digital converter 225 through analog prefilter 223 to permit audio input to the microcontroller 221, and an LCD display 229 is coupled to the microcontroller 221 to permit display of information regarding the functioning of the sensor interface device. Additionally, a speaker 230 is coupled to the microcontroller 221 to permit audio output of information regarding the functioning of the sensor interface device The microcontroller 221 runs a communication program that handles all communication with the training program and formats the incoming data from the sensors 201, 203, 205, and 207 in a manner permitting consumption of that data by the training program, including for purposes of display, storage, and manipulation. This communication program effectively provides a wrapper around the USB communication functionalities of the operating system of the computer 231. The aforementioned components may be operatively assembled using materials and techniques currently known in the art, however their collective operation in accordance with various embodiments of the invention is new.

FIG. 3 is a front perspective view of a sensor interface device in accordance with an embodiment of the present invention. Wire 301 acts as a ground to the sensor interface device. Cables 303, 305, 307, and 309 connect to sensors measuring skin conductance, respiration rate, heart rate, and skin temperature, respectively, as shown in more detail in connection with FIGS. 41-44. It should be appreciated that the assignment of cables to sensors is purely exemplary, and that different embodiments may assign the cables to the sensors in a different physical or logical order. LEDs 311, 313, 315, and 317 indicate whether the sensors that are connected to the sensor interface device via cables 303, 305, 307, and 309 are functioning properly. LED 319 indicates whether communication between the sensor interface device and the computer 231 is occurring wirelessly via Bluetooth protocols. LCD display 321 displays information regarding the functioning of the sensor interface device. Speaker 323 emits audio information. Button 325 powers the sensor interface device on and off. USB cable 327 connects the sensor interface device to computer 231 as an alternative or supplement to the use of Bluetooth protocols for communication between the sensor interface device and the computer.

FIG. 4 is a rear perspective view of the sensor interface device of FIG. 3. Cables 303, 305, 307, and 309 connect to sensors measuring skin temperature, heart rate, skin conductance, and respiration rate, respectively. USB cable 327 connects the sensor interface device to computer 231. Door 409 allows access to the batteries that power the sensor interface device.

Figure 5:
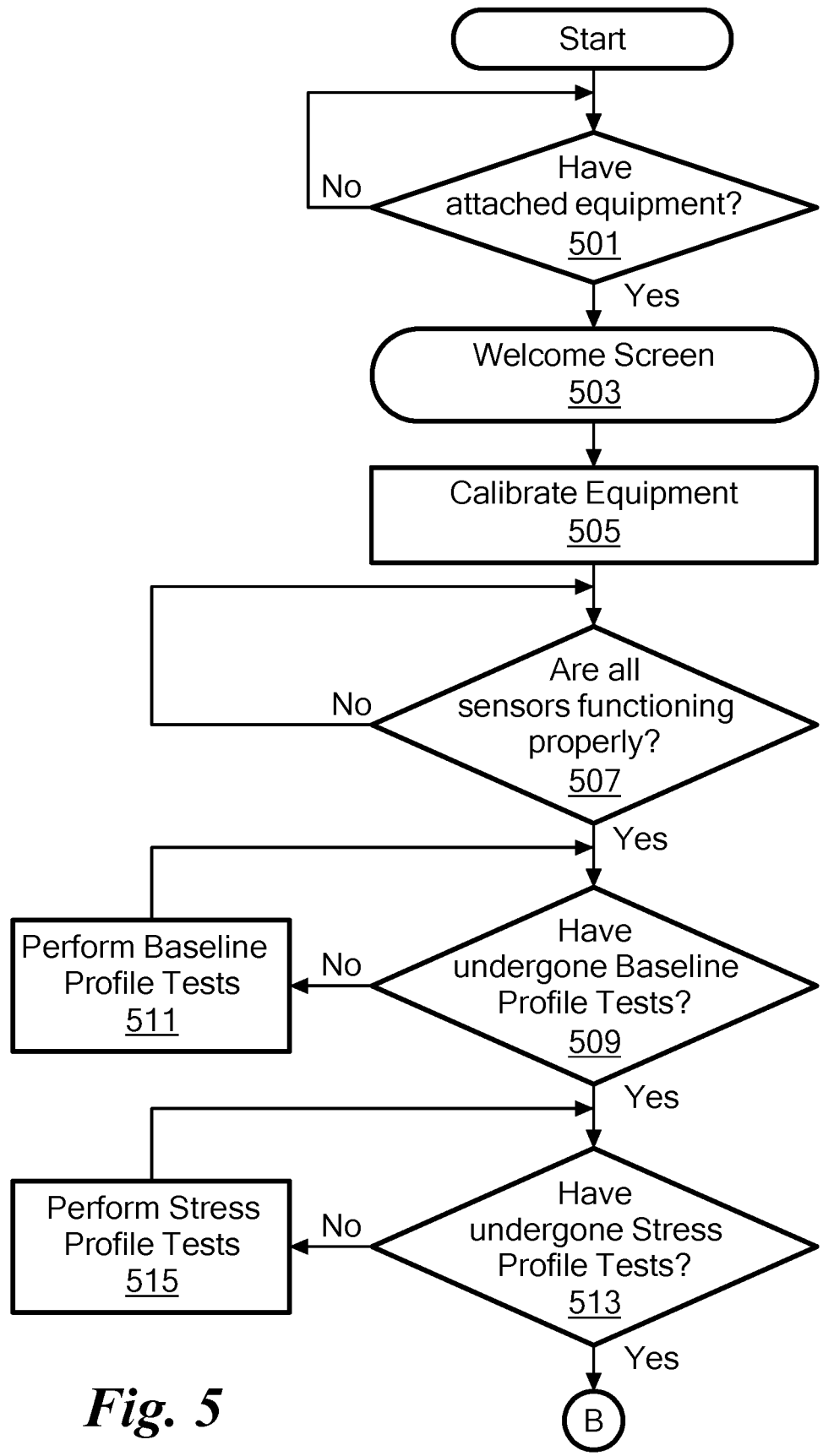
FIGS. 5 and 6 are detailed block diagrams of logical flow of an embodiment of the present invention, providing a sample of the range of capabilities of a rather fully implemented embodiment.
Figure 6:
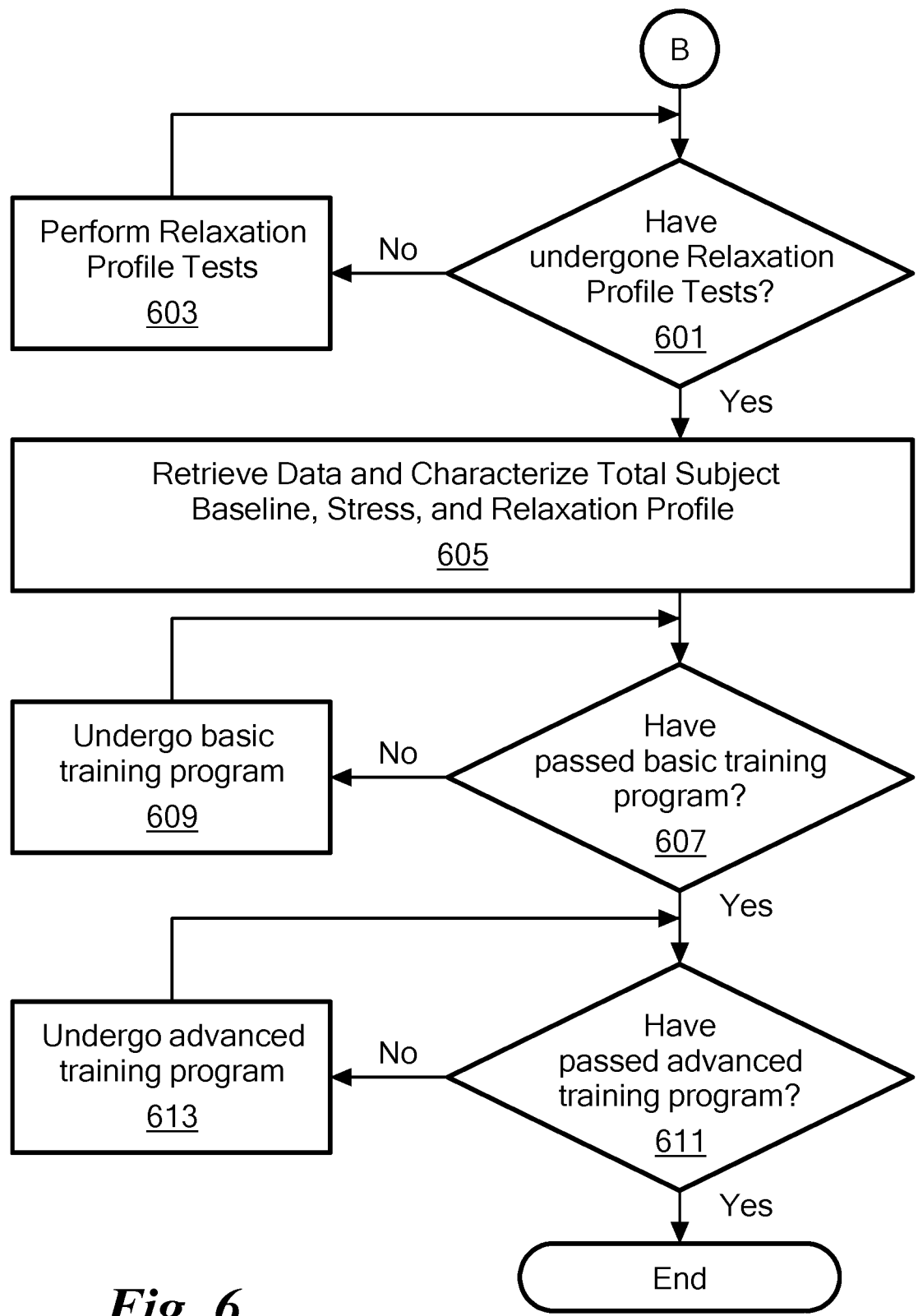

FIGS. 5 and 6 are detailed block diagrams of logical flow of an embodiment of the present invention, providing a sample of the range of capabilities of a rather fully implemented embodiment. In process 501, a program running in the computer 231 determines whether the sensing equipment (namely the sensors and the sensor interface device) is coupled to the computer 231. Until the determination is positive, the program continues to loop back to the beginning. Upon a determination that the equipment is coupled to the computer 231, the program causes a welcome screen to be presented in process 503. In process 505 and 507, the program running in the computer 231 determines whether the equipment (namely the sensors and the sensor interface device) is calibrated (namely, able to obtain measurements) to the computer 231. Until the determination is positive, the program continues to loop back to the beginning of process 507. Upon a determination that the equipment is calibrated to the computer 231, the program initiates process 509, wherein the program running in the computer 231 determines whether the subject has undergone Baseline Profile testing. If the determination of process 509 is negative, the program initiates process 511, Baseline Profile testing, and loops back until the determination of process 509 is positive. With a positive determination of process 509, the program running in the computer 231 initiates process 513, wherein the program running in the computer 231 determines whether the subject has undergone Stress Profile testing. If the determination of process 513 is negative, the program initiates process 515, Stress Profile testing, and loops back until the determination of process 513 is positive. With a positive determination of process 513, the program running in the computer 231 initiates process 601, wherein the program running in the computer 231 determines whether the subject has undergone Relaxation Profile testing. If the determination of process 601 is negative, the program initiates process 603, Stress Profile testing, and loops back until the determination of process 601 is positive. With a positive determination of process 601, the program running in the computer 231 initiates process 605, wherein the program running in the computer 231 retrieves data from processes 511, 515, and 603 and characterizes this data as the subject's total Baseline, Stress, and Relaxation Profile. In process 607 the program running in the computer 231 determines whether the subject has passed the basic training program. If the determination of process 607 is negative, the program initiates process 609, wherein the subject undergoes the basic training program, and loops back until the determination of process 607 is positive. With a positive determination of process 607, the program running in the computer 231 initiates process 611, wherein the program running in the computer 231 determines whether the subject has undergone the advanced training program. If the determination of process 611 is negative, the program initiates process 613, wherein the subject undergoes the advanced training program, and loops back until the determination of process 611 is positive, thereby causing the program running on computer 231 to end.

Figure 7:
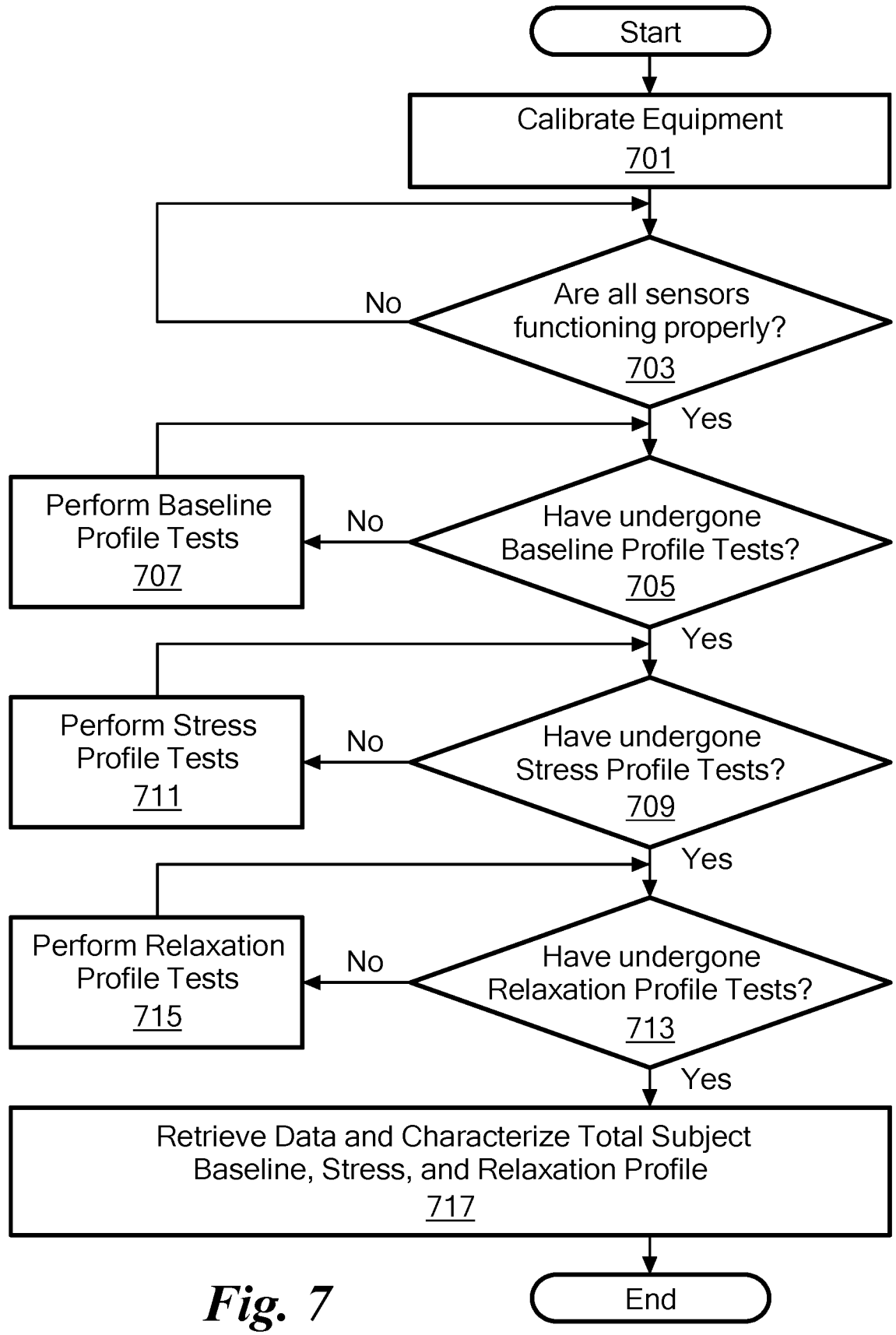
FIG. 7 is a block diagram of logical flow of an embodiment, similar to that of FIG. 1, that provides further details.

FIG. 7 is a block diagram of logical flow of an embodiment, similar to that of FIG. 1, which provides further details. In process 701, the program running in the computer 231 calibrates the sensing equipment (namely the sensors and the sensor interface device) that is coupled to the computer 231. In process 703, the program running in the computer 231 determines whether all of the sensors are functioning properly. Until the determination is positive, the program continues to loop back to the beginning. Upon a determination that the equipment is functioning properly, the program initiates process 705, wherein the program running in the computer 231 determines whether the subject has undergone Baseline Profile testing. If the determination of process 705 is negative, the program initiates process 707, Baseline Profile testing, and loops back until the determination of process 705 is positive. With a positive determination of process 705, the program running in the computer 231 initiates process 709, wherein the program running in the computer 231 determines whether the subject has undergone Stress Profile testing. If the determination of process 709 is negative, the program initiates process 711, Stress Profile testing, and loops back until the determination of process 709 is positive. With a positive determination of process 709, the program running in the computer 231 initiates process 713, wherein the program running in the computer 231 determines whether the subject has undergone Relaxation Profile testing. If the determination of process 713 is negative, the program initiates process 715, Relaxation Profile testing, and loops back until the determination of process 713 is positive. With a positive determination of process 713, the program running in the computer 231 initiates process 717, wherein the program running in the computer 231 retrieves data from processes 707, 711, and 715 and characterizes this data as the subject's total Baseline, Stress, and Relaxation Profile.

Figure 8:
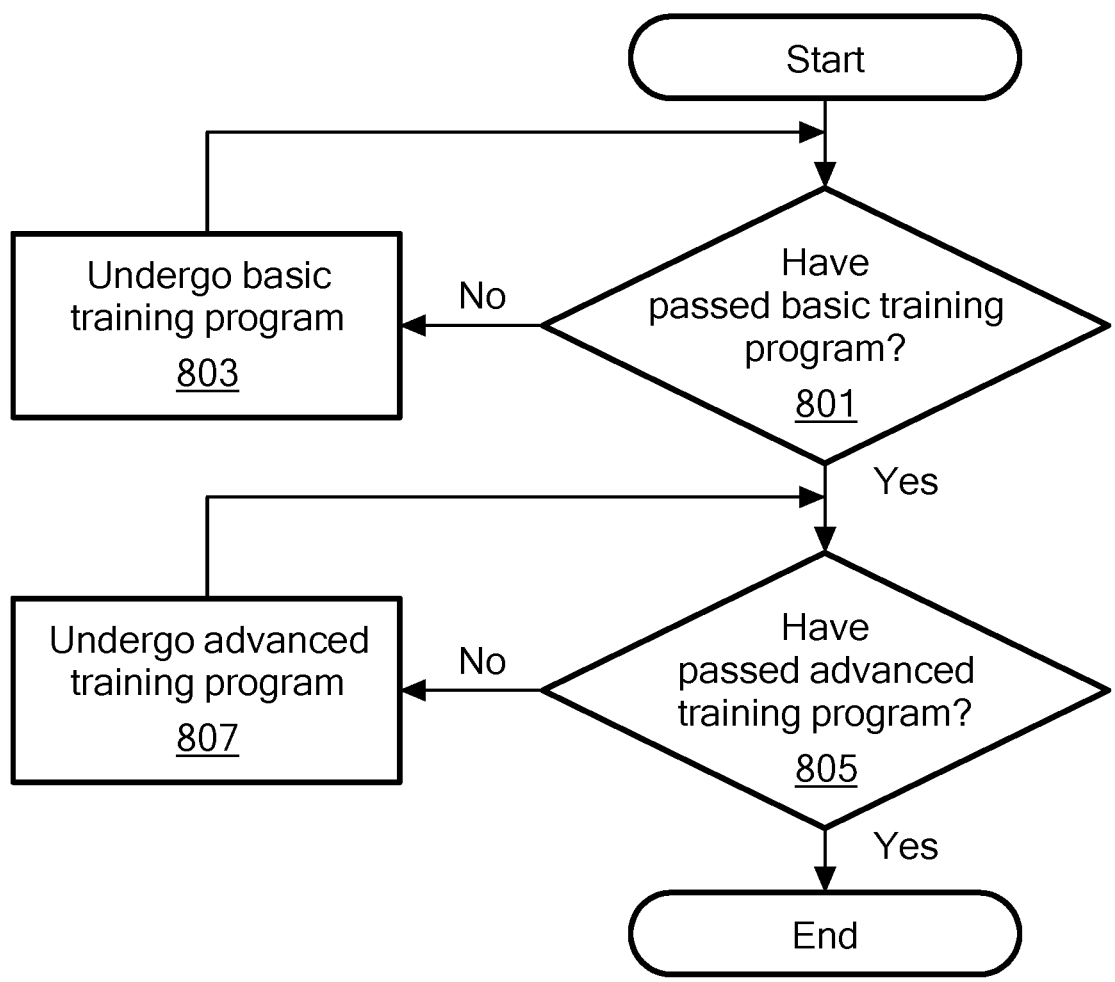
FIG. 8 is block diagram of logical flow of an embodiment of the present invention in which training is provided.

FIG. 8 is block diagram of logical flow of an embodiment of the present invention in which training is provided. In process 801, the program running in the computer 231 determines whether the subject has passed the basic training program. If the determination of process 801 is negative, the program initiates process 803, wherein the subject undergoes the basic training program, and loops back until the determination of process 801 is positive. With a positive determination of process 801, the program running in the computer 231 initiates process 805, wherein the program running in the computer 231 determines whether the subject has undergone the advanced training program. If the determination of process 805 is negative, the program initiates process 807, wherein the subject undergoes the advanced training program, and loops back until the determination of process 805 is positive, thereby causing the program running on computer 231 to end.

Figure 9:
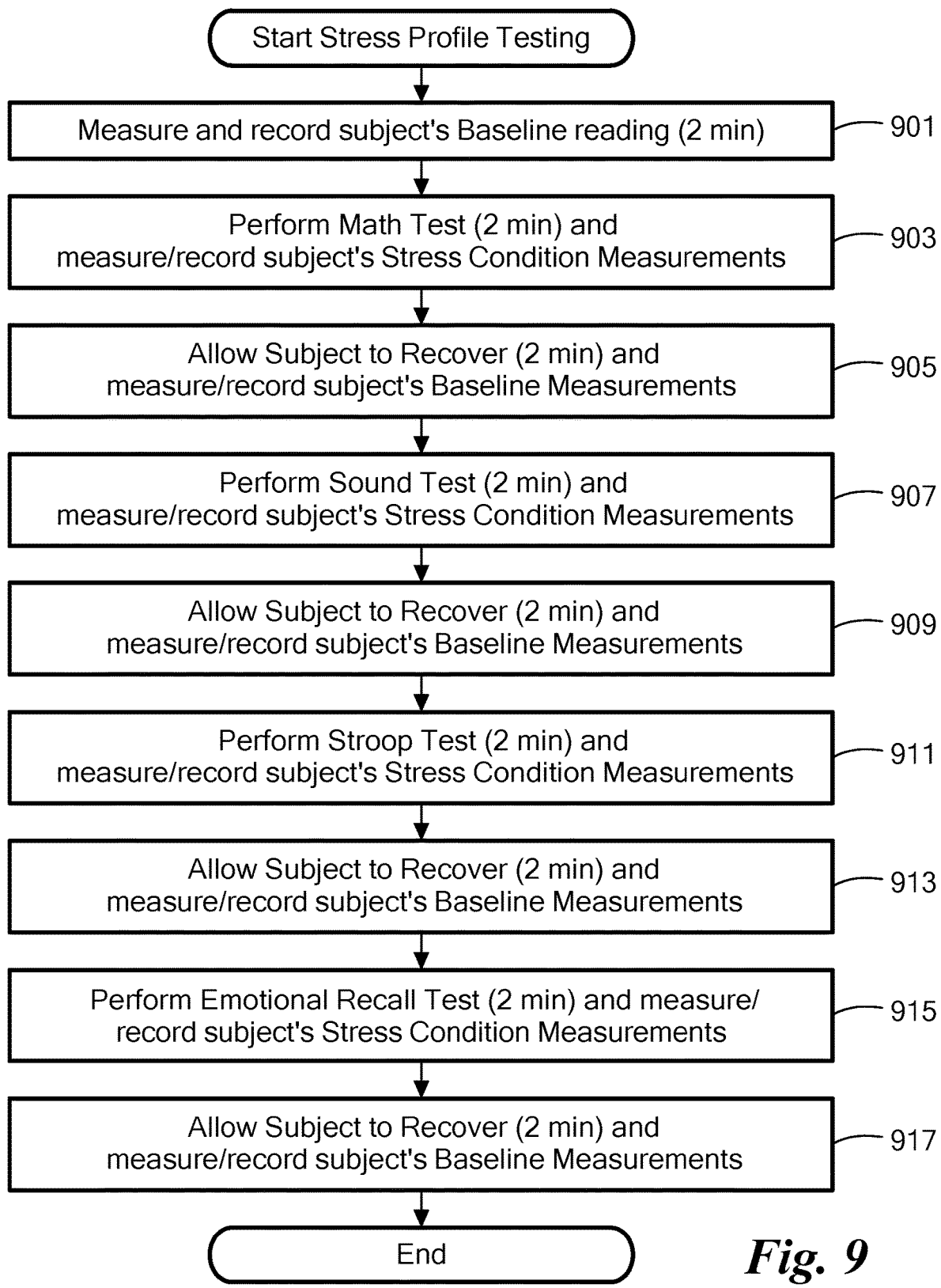
FIG. 9 is a block diagram of logical flow of an embodiment of the present invention, adding detail to FIG. 1, in which stress testing is performed.

FIG. 9 is a block diagram of logical flow of an embodiment of the present invention, adding detail to FIG. 1, in which the Stress Profile testing is performed. In process 901, the program running in the computer 231 initiates measurement and recording of the subject's baseline readings (e.g. heart rate, skin conductance, skin temperature, and respiration rate) for a specified period of time. In process 903, the program running in the computer 231 initiates a math test, wherein the subject is prompted to answer a series of math questions within a specified period of time. During process 903, the subject's stress condition measurements (e.g. heart rate, skin conductance, skin temperature, and respiration rate) are measured and recorded. In process 905, the program running in the computer 231 initiates a recovery period, wherein the subject is prompted to recover from the previous testing for a specified period of time. During process 905, the subject's baseline measurements in recovery are measured and recorded. In process 907, the program running in the computer 231 initiates a sound test, wherein the subject is exposed to a series of discordant sounds within a specified period of time. During process 907, the subject's stress condition measurements are measured and recorded. In process 909, the program running in the computer 231 initiates a recovery period, wherein the subject is prompted to recover from the previous testing for a specified period of time. During process 909, the subject's baseline measurements in recovery are measured and recorded. In process 911, the program running in the computer 231 initiates a Stroop test, wherein the subject is exposed to a series of questions related to color and word meaning within a specified period of time. During process 911, the subject's stress condition measurements are measured and recorded. In process 913, the program running in the computer 231 initiates a recovery period, wherein the subject is prompted to recover from the previous testing for a specified period of time. During process 913, the subject's baseline measurements in recovery are measured and recorded. In process 915, the program running in the computer 231 initiates an Emotional Recall test, wherein the subject is prompted to recall and retell the details of a stressful event that the subject has experienced within the recent past within a specified period of time. During process 915, the subject's stress condition measurements are measured and recorded. In process 917, the program running in the computer 231 initiates a recovery period, wherein the subject is prompted to recover from the previous testing for a specified period of time. During process 917, the subject's baseline measurements in recovery are measured and recorded. The periods of time specified in this exemplary figure are each two minutes, however other periods of time may be specified in different embodiments, and each such period of time may be set independently of the others.

Figure 10:
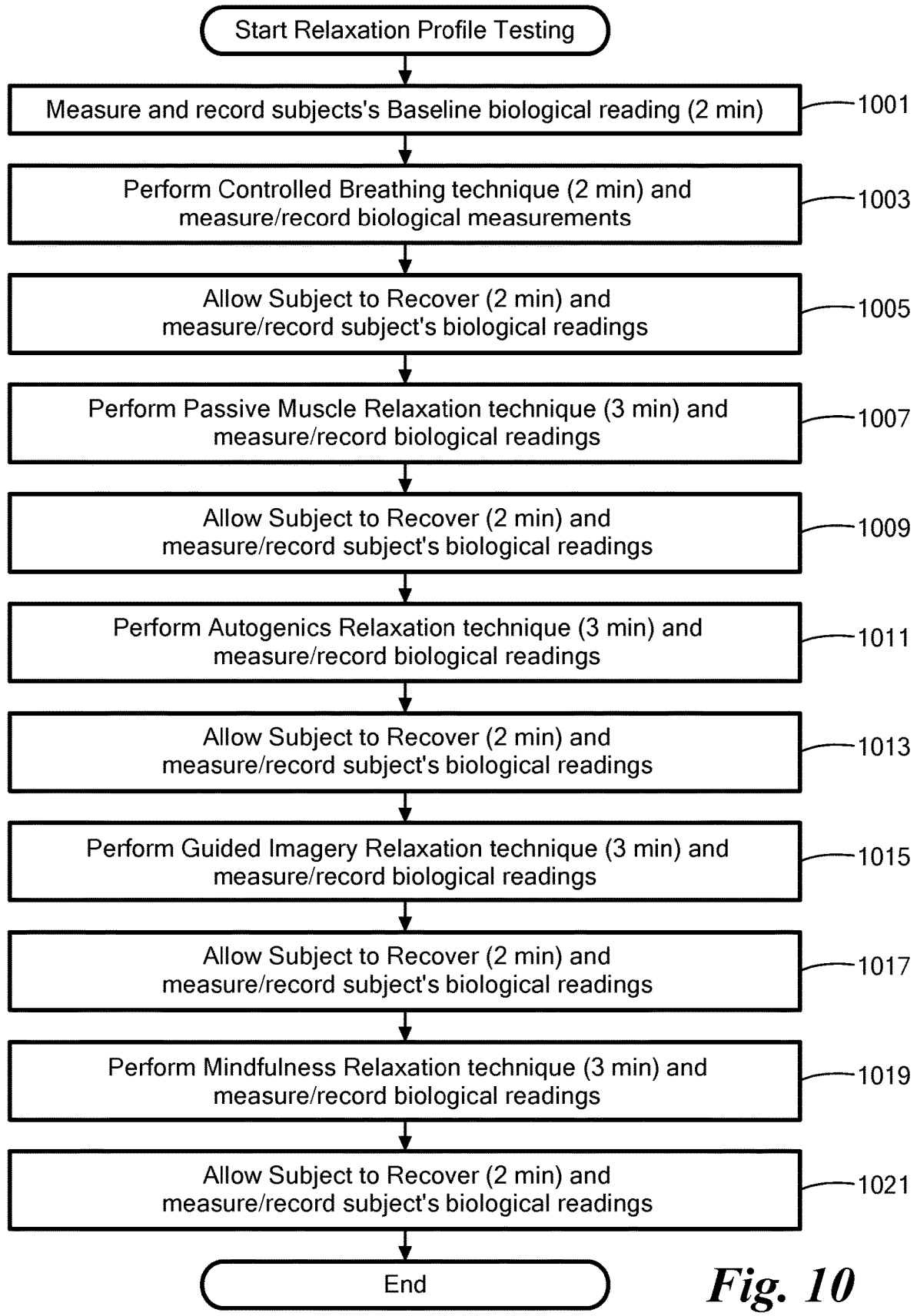
FIG. 10 is a block diagram of logical flow of an embodiment of the present invention, adding detail to FIG. 1, in which relaxation testing is performed.

FIG. 10 is a block diagram of logical flow of an embodiment of the present invention, adding detail to FIG. 1, in which Relaxation Profile testing is performed. In process 1001, the program running in the computer 231 initiates measurement and recording of the subject's baseline readings (heart rate, skin conductance, skin temperature, and respiration rate) for a specified period of time. In process 1003, the program running in the computer 231 initiates a controlled breathing relaxation protocol, wherein the subject is prompted to breathe at a measured pace within a specified period of time. During process 1003, the subject's relaxation condition measurements (heart rate, skin conductance, skin temperature, and respiration rate) are measured and recorded. In process 1005, the program running in the computer 231 initiates a recovery period, wherein the subject is prompted to recover from the previous testing for a specified period of time. During process 1005, the subject's baseline measurements in recovery are measured and recorded. In process 1007, the program running in the computer 231 initiates a passive muscle relaxation protocol, wherein the subject is prompted to relax his or her muscles within a specified period of time. During process 1007, the subject's relaxation condition measurements are measured and recorded. In process 1009, the program running in the computer 231 initiates a recovery period, wherein the subject is prompted to recover from the previous testing for a specified period of time. During process 1009, the subject's baseline measurements in recovery are measured and recorded. In process 1011, the program running in the computer 231 initiates an autogenics relaxation protocol, wherein the subject is exposed to a series of autogenics techniques within a specified period of time. During process 1011, the subject's stress condition measurements are measured and recorded. In process 1013, the program running in the computer 231 initiates a recovery period, wherein the subject is prompted to recover from the previous testing for a specified period of time. During process 1013, the subject's baseline measurements in recovery are measured and recorded. In process 1015, the program running in the computer 231 initiates a guided imagery relaxation protocol, wherein the subject is guided through mental imagery procedures within a specified period of time. During process 1015, the subject's relaxation condition measurements are measured and recorded. In process 1017, the program running in the computer 231 initiates a recovery period, wherein the subject is prompted to recover from the previous testing for a specified period of time. During process 1017, the subject's baseline measurements in recovery are measured and recorded. In process 1019, the program running in the computer 231 initiates a mindfulness relaxation protocol, wherein the subject is exposed to mindfulness exercises within a specified period of time. During process 1019, the subject's relaxation condition measurements are measured and recorded. In process 1021, the program running in the computer 231 initiates a recovery period, wherein the subject is prompted to recover from the previous testing for a specified period of time. During process 1021, the subject's baseline measurements in recovery are measured and recorded. The periods of time specified in this exemplary figure may differ in different embodiments, and each such period of time may be set independently of the others.

Figure 11:
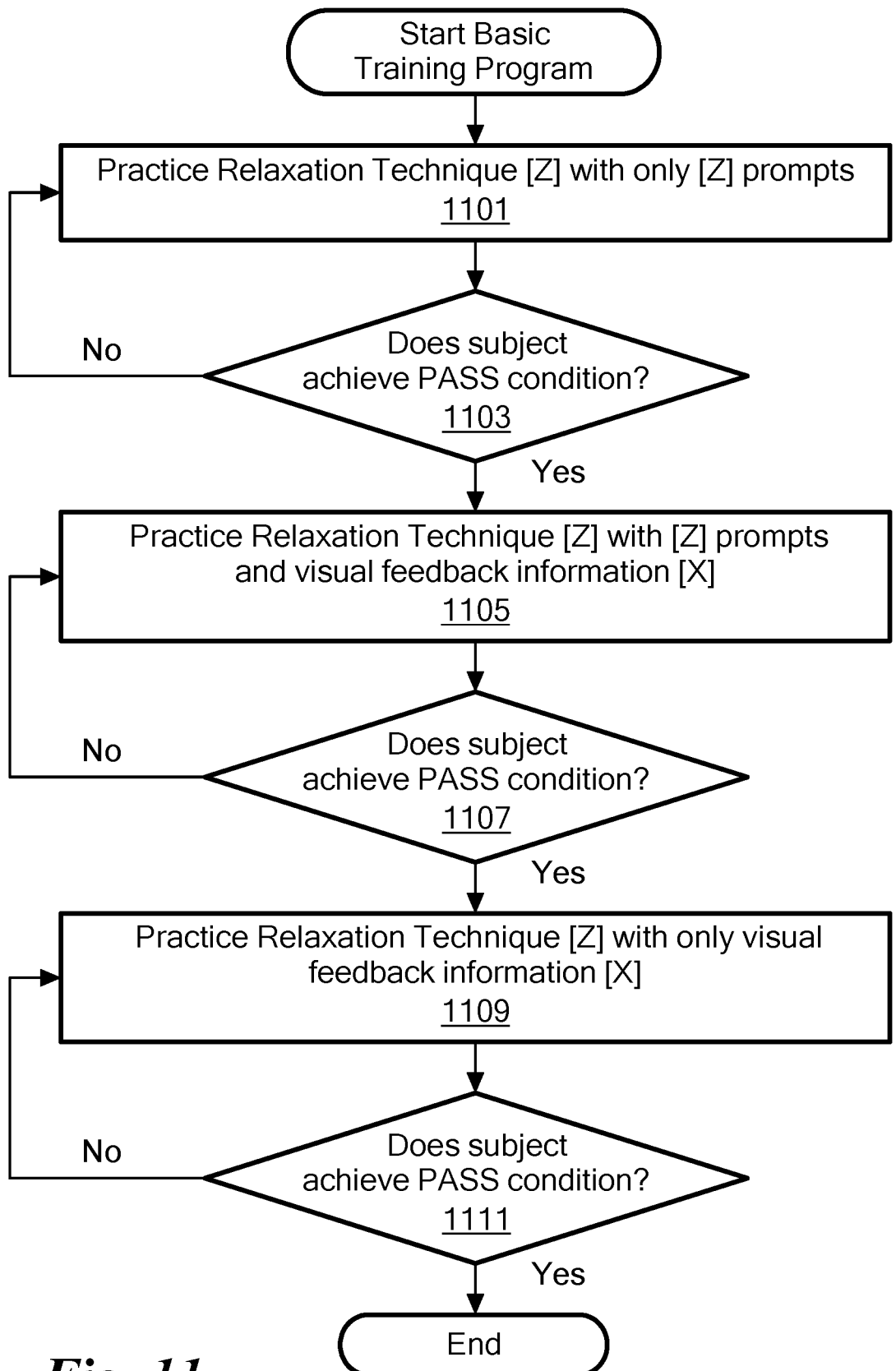
FIG. 11 is a block diagram of logical flow of an embodiment of the present invention, adding detail to FIG. 8, in which basic training is provided.

FIG. 11 is a block diagram of logical flow of an embodiment of the present invention, adding detail to FIG. 8, in which basic training is provided. In process 1101, the program running in the computer 231 initiates practice with visual prompting of the specified relaxation protocol for a specified period of time. During process 1101, the subject's specified stress-indicating physiological parameter is measured and compared to the baseline measurement of process 101. In process 1103, the program running in the computer 231 determines whether the subject's stress-indicating physiological parameter is within a certain range of the baseline measurement of process 101. Until the determination is positive, the program continues to loop back to the beginning of process 1101. Upon a determination that the subject's stress-indicating physiological parameter is within a certain range of the baseline measurement of process 101, the program initiates process 1105, wherein the program running in the computer 231 initiates practice with visual prompting of the specified relaxation protocol with visual feedback information regarding the subject's specified stress-indicating physiological parameter for a specified period of time. During process 1105, the subject's specified stress-indicating physiological parameter is measured and compared to the baseline measurement of process 101. In process 1107, the program running in the computer 231 determines whether the subject's stress-indicating physiological parameter is within a certain range of the baseline measurement of process 101. Until the determination is positive, the program continues to loop back to the beginning of process 1105. Upon a determination that the subject's stress-indicating physiological parameter is within a certain range of the baseline measurement of process 101, the program initiates process 1109, wherein the program running in the computer 231 initiates practice without visual prompting of the specified relaxation protocol but with visual feedback information regarding the subject's specified stress-indicating physiological parameter for a specified period of time. During process 1109, the subject's specified stress-indicating physiological parameter is measured and compared to the baseline measurement of process 101. In process 1111, the program running in the computer 231 determines whether the subject's stress-indicating physiological parameter is within a certain range of the baseline measurement of process 101. Until the determination is positive, the program continues to loop back to the beginning of process 1109. Upon a determination that the subject's stress-indicating physiological parameter is within a certain range of the baseline measurement of process 101, the subject is deemed to have passed the basic training program.

Figure 12:
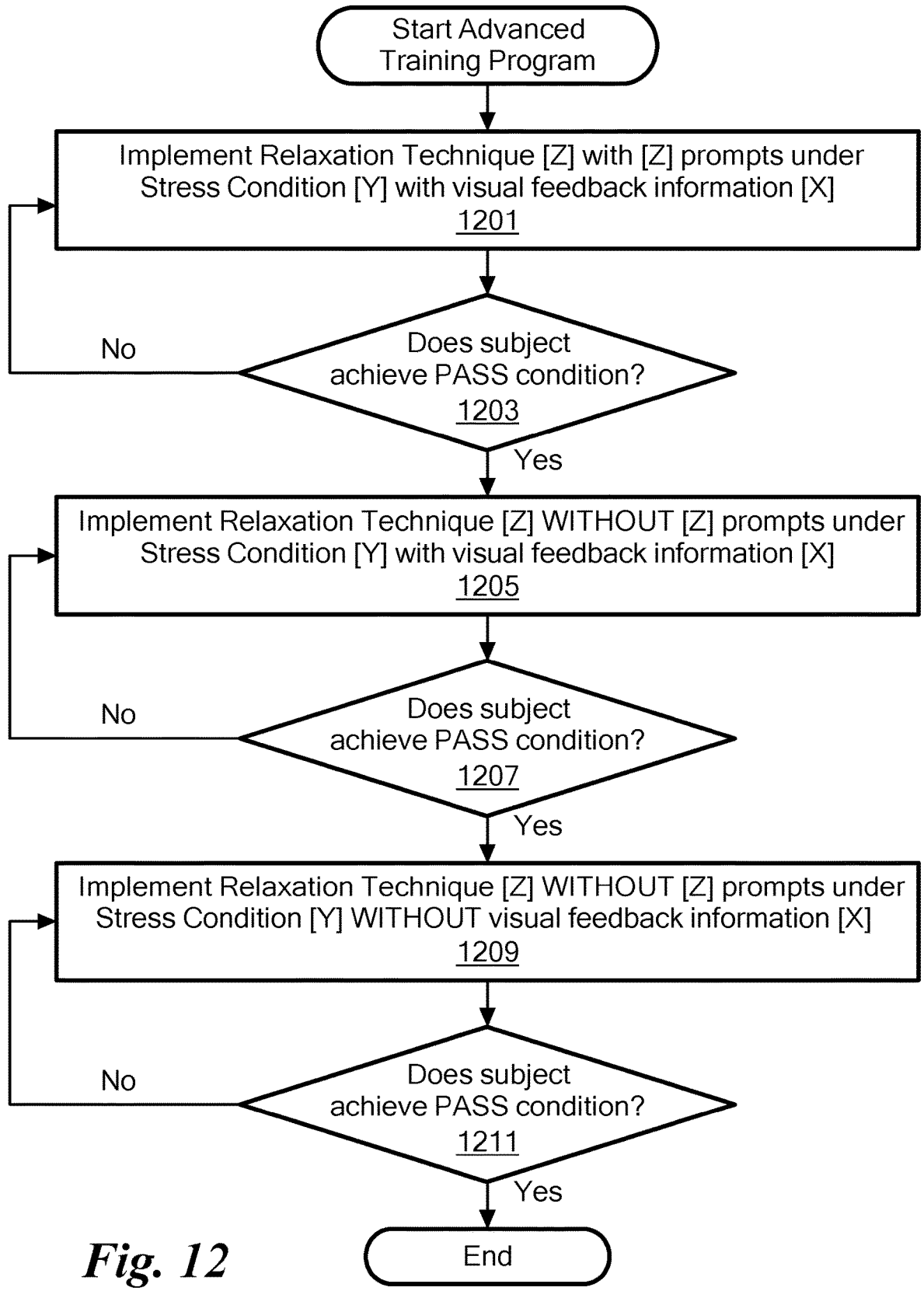
FIG. 12 is a block diagram of logical flow of an embodiment of the present invention, adding detail to FIG. 8, in which advanced training is provided.

FIG. 12 is a block diagram of logical flow of an embodiment of the present invention, adding detail to FIG. 8, in which advanced training is provided. In process 1201, the program running in the computer 231 initiates practice with visual prompting of the specified relaxation protocol with visual feedback information regarding the subject's specified stress-indicating physiological parameter while exposing the subject to the specified stress-inducing activity for a specified period of time. During process 1201, the subject's specified stress-indicating physiological parameter is measured and compared to the baseline measurement of process 101. In process 1203, the program running in the computer 231 determines whether the subject's stress-indicating physiological parameter is within a certain range of the baseline measurement of process 101. Until the determination is positive, the program continues to loop back to the beginning of process 1201. Upon a determination that the subject's stress-indicating physiological parameter is within a certain range of the baseline measurement of process 101, the program initiates process 1205, wherein the program running in the computer 231 initiates practice without visual prompting of the specified relaxation protocol but with visual feedback information regarding the subject's specified stress-indicating physiological parameter while exposing the subject to the specified stress-inducing activity for a specified period of time. During process 1205, the subject's specified stress-indicating physiological parameter is measured and compared to the baseline measurement of process 101. In process 1207, the program running in the computer 231 determines whether the subject's stress-indicating physiological parameter is within a certain range of the baseline measurement of process 101. Until the determination is positive, the program continues to loop back to the beginning of process 1205. Upon a determination that the subject's stress-indicating physiological parameter is within a certain range of the baseline measurement of process 101, the program initiates process 1209, wherein the program running in the computer 231 initiates practice without visual prompting of the specified relaxation protocol and without visual feedback information regarding the subject's specified stress-indicating physiological parameter while exposing the subject to the specified stress-inducing activity for a specified period of time. During process 1209, the subject's specified stress-indicating physiological parameter is measured and compared to the baseline measurement of process 101. In process 1211, the program running in the computer 231 determines whether the subject's stress-indicating physiological parameter is within a certain range of the baseline measurement of process 101. Until the determination is positive, the program continues to loop back to the beginning of process 1209. Upon a determination that the subject's stress-indicating physiological parameter is within a certain range of the baseline measurement of process 101, the subject is deemed to have passed the advanced training program.

Figure 13:
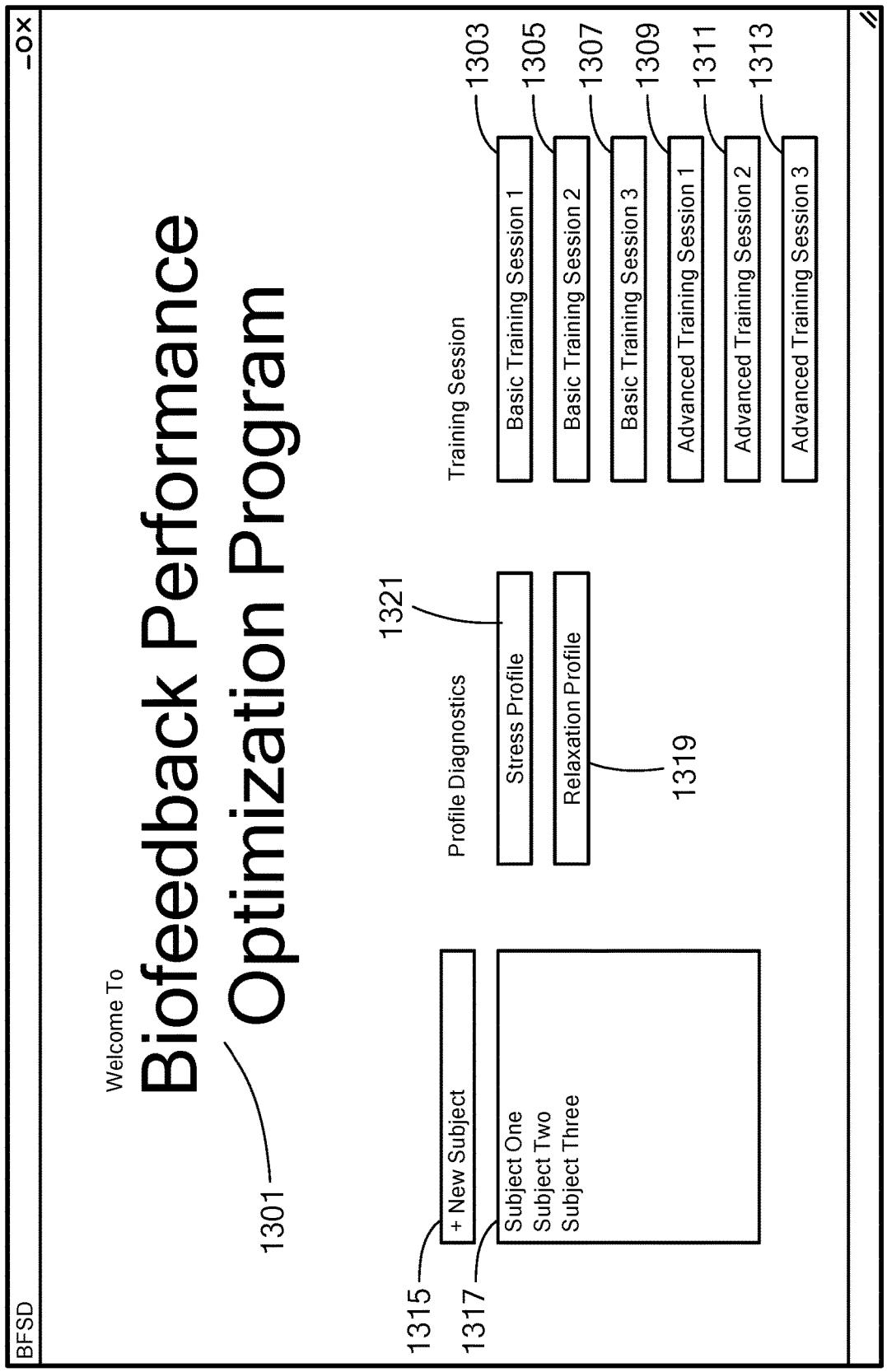
FIG. 13 is a representation of a display of a welcome screen, by a subject's computer, in accordance with an embodiment of the present invention, wherein the computer is running a program for training the subject to improve psychophysiological function.

FIG. 13 is a representation of a display of a welcome screen, by a subject's computer, in accordance with an embodiment of the present invention, wherein the computer is running a program for training the subject to improve psychophysiological function. On this welcome screen, the subject is presented with title 1301. A button 1315 enables the subject to create a new user profile. Upon creation of a user profile, the subject's user profile will be listed in window 1317. Buttons 1319 and 1321 enable the subject to undergo Relaxation Profile and Stress Profile testing, respectively. Buttons 1303, 1305, 1307, 1309, 1311, and 1313 enable the subject to perform basic training sessions 1, 2, and 3, and advanced training sessions 1, 2, and 3, respectively.

Figure 14:
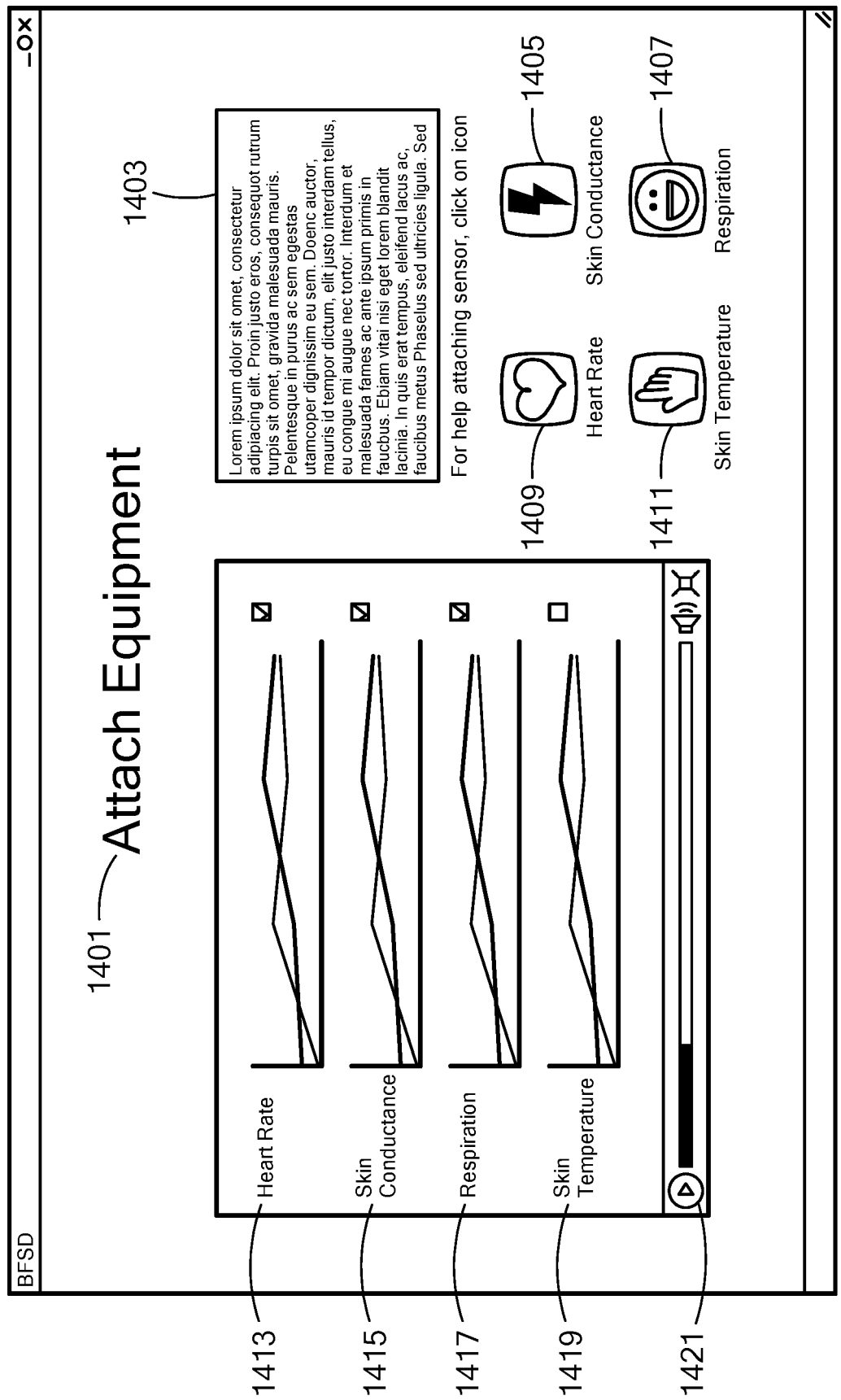
FIG. 14 is a representation of a display of an attach-equipment screen associated with the program of FIG. 13.

FIG. 14 is a representation of a display of an attach-equipment screen associated with the program of FIG. 13. On this screen, the subject is presented with title 1401 and text window 1403, which provides the subject with instructions on how to attach sensors (heart rate, skin temperature, respiration rate, and skin conductance). Buttons 1405, 1407, 1409, and 1411 enable the subject to receive audio instructions for attaching sensors, with audio controls 1421. Images 1413, 1415, 1417, and 1419 provide the subject with visual information regarding successful attachment and functioning of the sensors.

Figure 15:
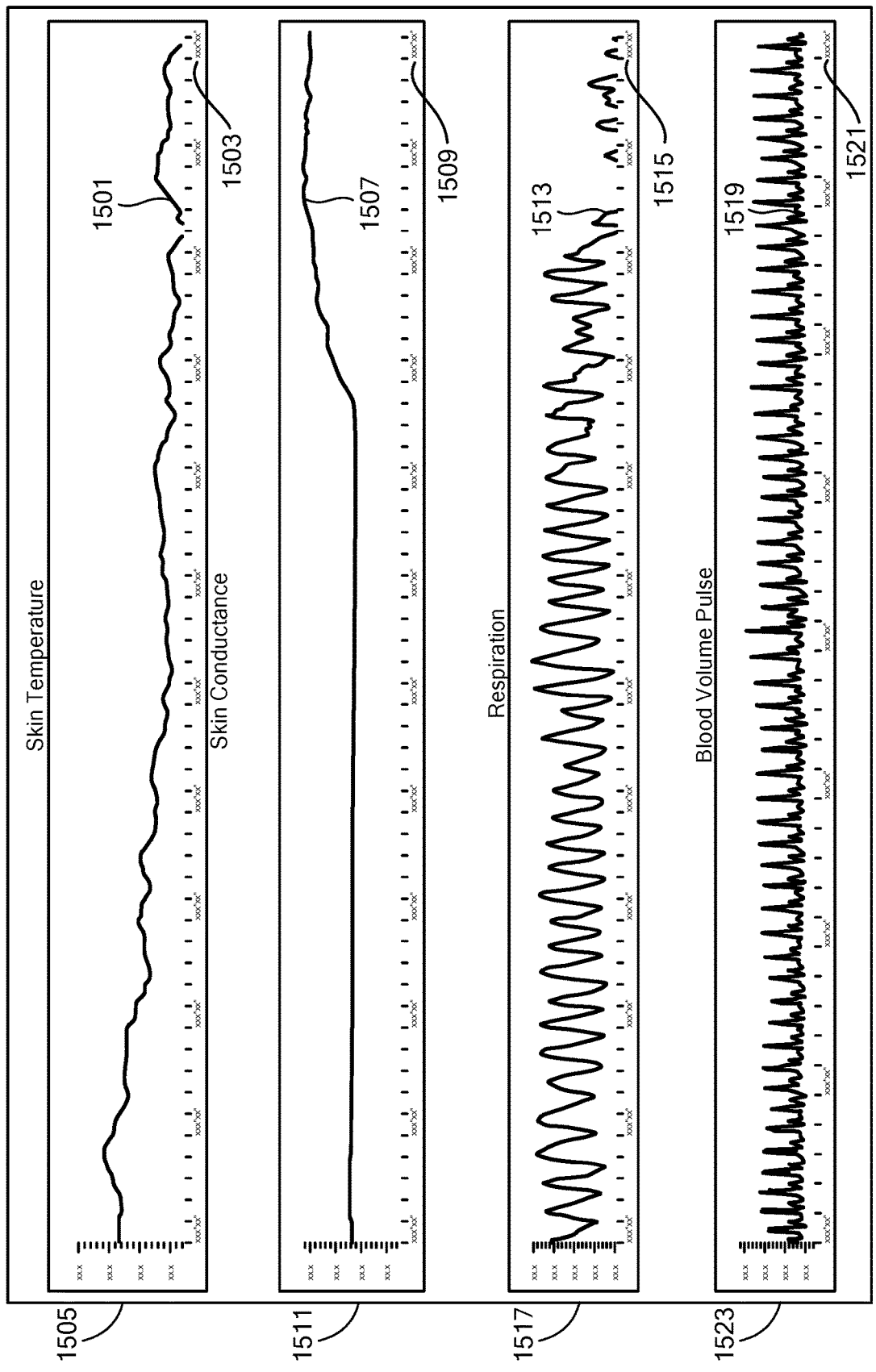
FIG. 15 is a representation of measurement data, as a function of time, that is transmitted by a sensor interface device to the subject's computer when the subject is receiving training while the subject's computer is running the program of FIG. 13.

FIG. 15 is a representation of measurement data, as a function of time, that is transmitted by a sensor interface device to the subject's computer when the subject is receiving training while the subject's computer is running the program of FIG. 13. Image 1501 displays the subject's skin temperature measurement on a scale 1505 over time 1503. Image 1507 displays the subject's skin conductance measurement on a scale 1511 over time 1509. Image 1513 displays the subject's respiration rate measurement on a scale 1517 over time 1515. Image 1519 displays the subject's respiration rate measurement on a scale 1523 over time 1521.

Figure 16:
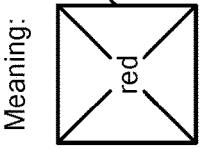
FIG. 16 is a representation of a screen display associated with a stress-inducing activity (Stroop test) established and monitored by the program of FIG. 13.

FIG. 16 is a representation of a screen display associated with a stress-inducing activity (Stroop test 911) established and monitored by the program of FIG. 13. On this screen, the subject is presented with title 1601, and text window 1603, a display of question numbers with indication of correct or incorrect. Image 1609 represents the meaning of the word being displayed. Image 1611 represents the color of the text being displayed. Buttons 1607 enable the subject to respond in the affirmative or negative if the meaning display 1609 and the color display 1611 match, thereby stressing the subject. Audio control 1605 enables the subject to adjust the program's volume.

FIG. 17 is a representation of a screen display associated with a stress-inducing activity (math test 903) established and monitored by the program of FIG. 13. On this screen, the subject is presented with title 1701, and text window 1705, a display of question numbers with indication of correct or incorrect. Image 1703 presents the subject with a math problem. Buttons 1707 enable the subject to enter an answer to math question 1703, thereby stressing the subject. Display 1709 indicates time remaining (in minutes and seconds) in the activity represented on the screen display.

Figure 18:
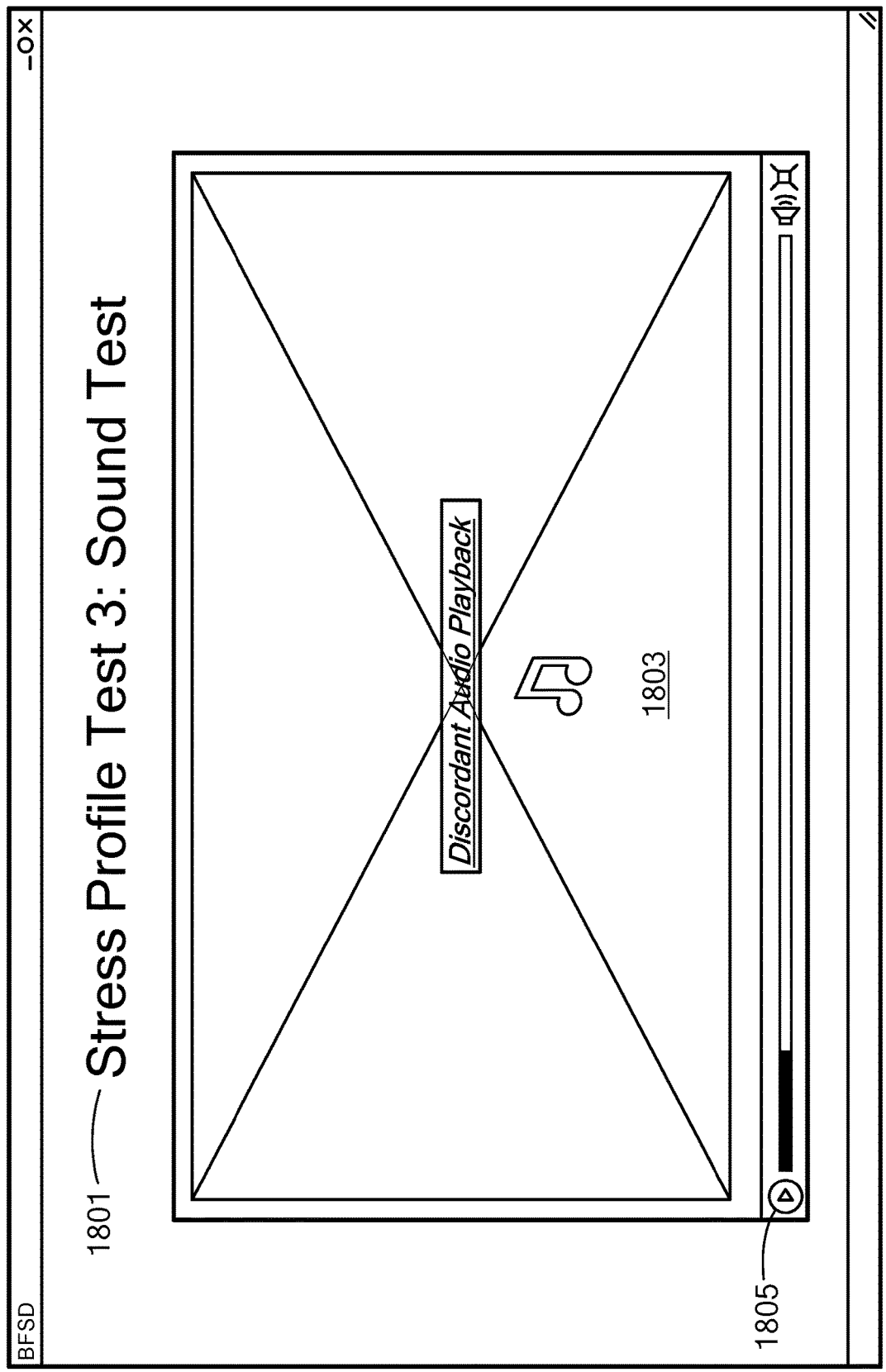
FIG. 18 is a representation of a screen display associated with a stress-inducing activity (sound test) established and monitored by the program of FIG. 13.

FIG. 18 is a representation of a screen display associated with a stress-inducing activity (sound test 907) established and monitored by the program of FIG. 13. On this screen, the subject is presented with title 1801 and volume control 1805. Blank window 1803 will produce discordant sounds to expose to the subject, thereby stressing the subject.

Figure 19:
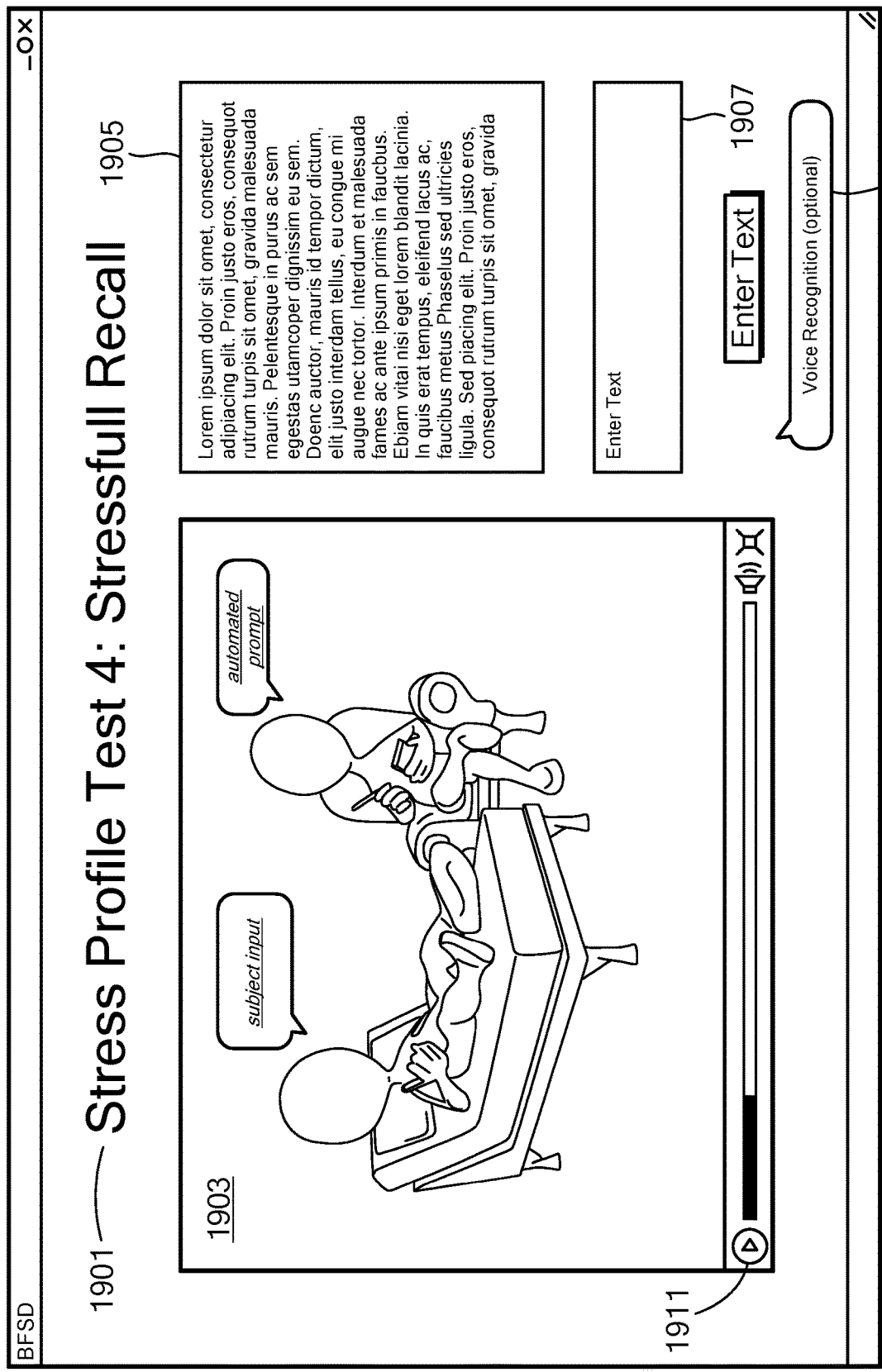
FIG. 19 is a representation of a screen display associated with a stress-inducing activity (stressful event recall) established and monitored by the program of FIG. 13.

FIG. 19 is a representation of a screen display associated with a stress-inducing activity (stressful event recall 915) established and monitored by the program of FIG. 13. On this screen, the subject is presented with title 1901 and text window 1905, which provides the subject with instructions on how to recall a particularly stressful event. Window 1903 provides the subject with a visual representation of an individual recalling a stressful event to a practitioner, who now and again may provide the subject with audio and visual prompts, controlled by volume control 1911. Box 1907 enables the subject to input type detailing the stressful event recall, and button 1909 optionally allows the subject to enable voice recognition capabilities.

Figure 20:
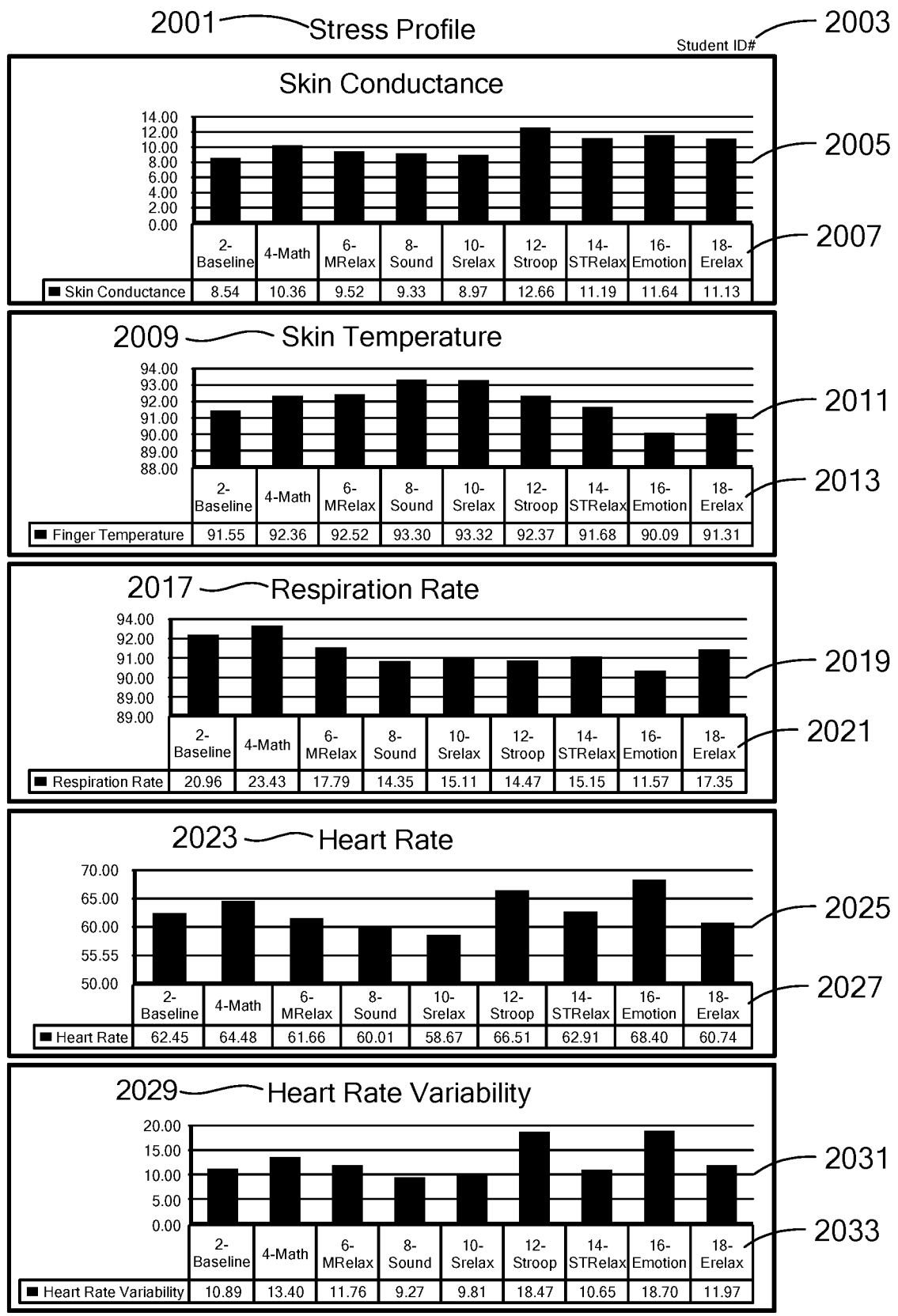
FIG. 20 is a representation of a display of a stress profile screen, wherein the results of activities associated with FIGS. 16-19 are summarized and presented visually to the subject by the program of FIG. 13.

FIG. 20 is a representation of a display of a stress profile screen, wherein the results of activities associated with FIGS. 16-19 are summarized and presented visually to the subject by the program of FIG. 13. On this screen, the subject is presented with title 2001 and user ID #2003. Visual image 2005 and text boxes 2007 present the subject with information regarding the subject's skin conductance measurements over the activities in Stress Profile testing associated with FIG. 9. Title 2009, visual image 2011 and text boxes 2013 present the subject with information regarding the subject's skin temperature measurements over the activities in Stress Profile testing associated with FIG. 9. Title 2017, visual image 2019, and text boxes 2021 present the subject with information regarding the subject's respiration rate measurements over the activities in Stress Profile testing associated with FIG. 9. Title 2023, visual image 2025, and text boxes 2027 present the subject with information regarding the subject's heart rate measurements over the activities in Stress Profile testing associated with FIG. 9. Title 2029, visual image 2031, and text boxes 2033 present the subject with information regarding the subject's heart rate variability measurements over the activities in Stress Profile testing associated with FIG. 9.

Figure 21:
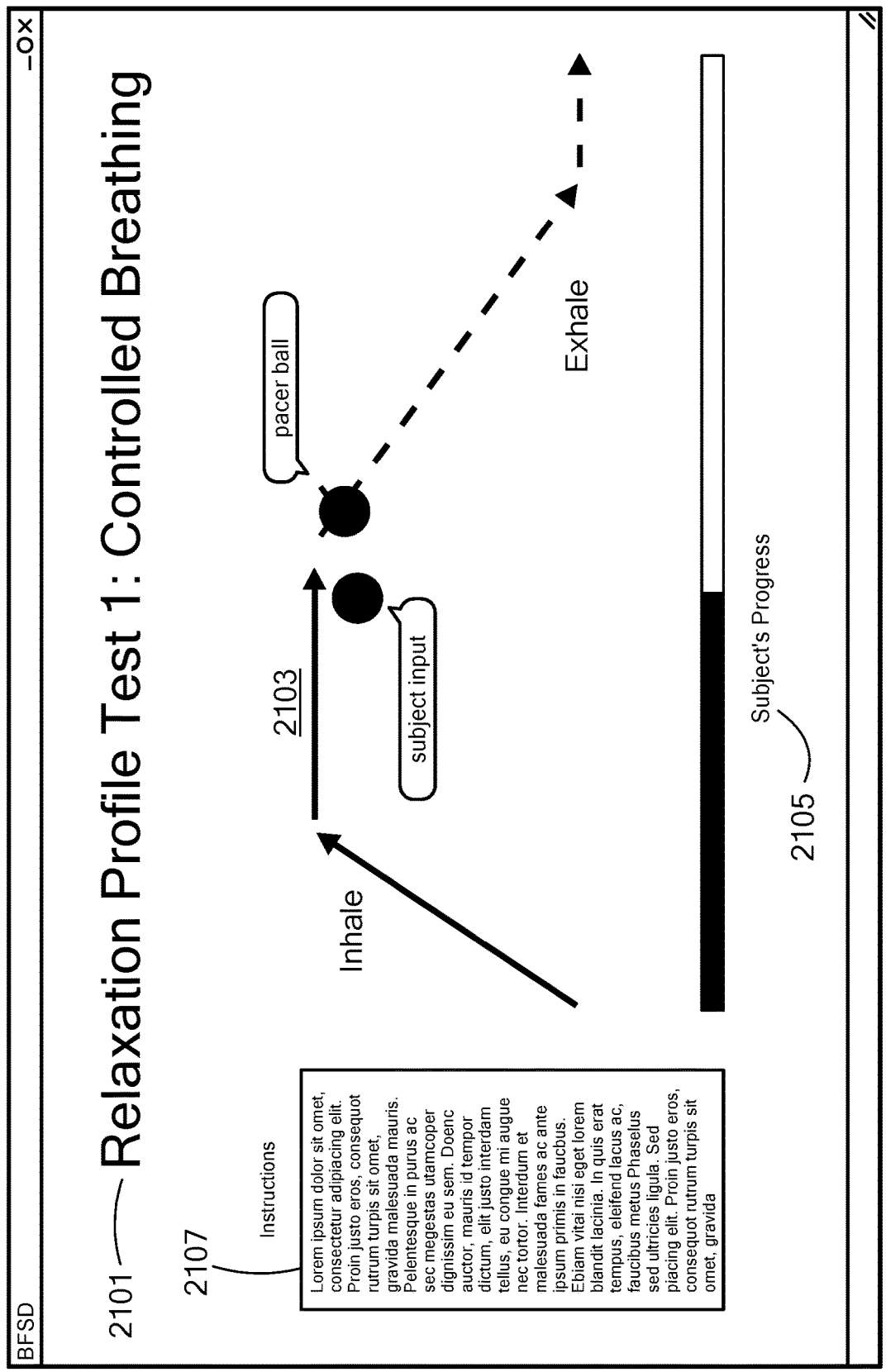
FIG. 21 is a representation of a screen display associated with testing, for effectiveness of controlled breathing for use in a relaxation protocol, established and monitored by the program of FIG. 13.

FIG. 21 is a representation of screen display associated with testing, for effectiveness of controlled breathing for use in a relaxation protocol, established and monitored by the program of FIG. 13. On this screen, the subject is presented with title 2101 and text window 2107, which provides the subject with instructions on how to undergo the relaxation-inducing protocol controlled breathing 1003. Window 2103 provides the subject with a visual representation of a pacer for controlled breathing, by which the subject is provided visual information regarding how closely he or she is breathing in sync with a specified respiration rate. Bar 2105 presents the subject with visual information regarding progress (time) through the exercise.

Figure 22:
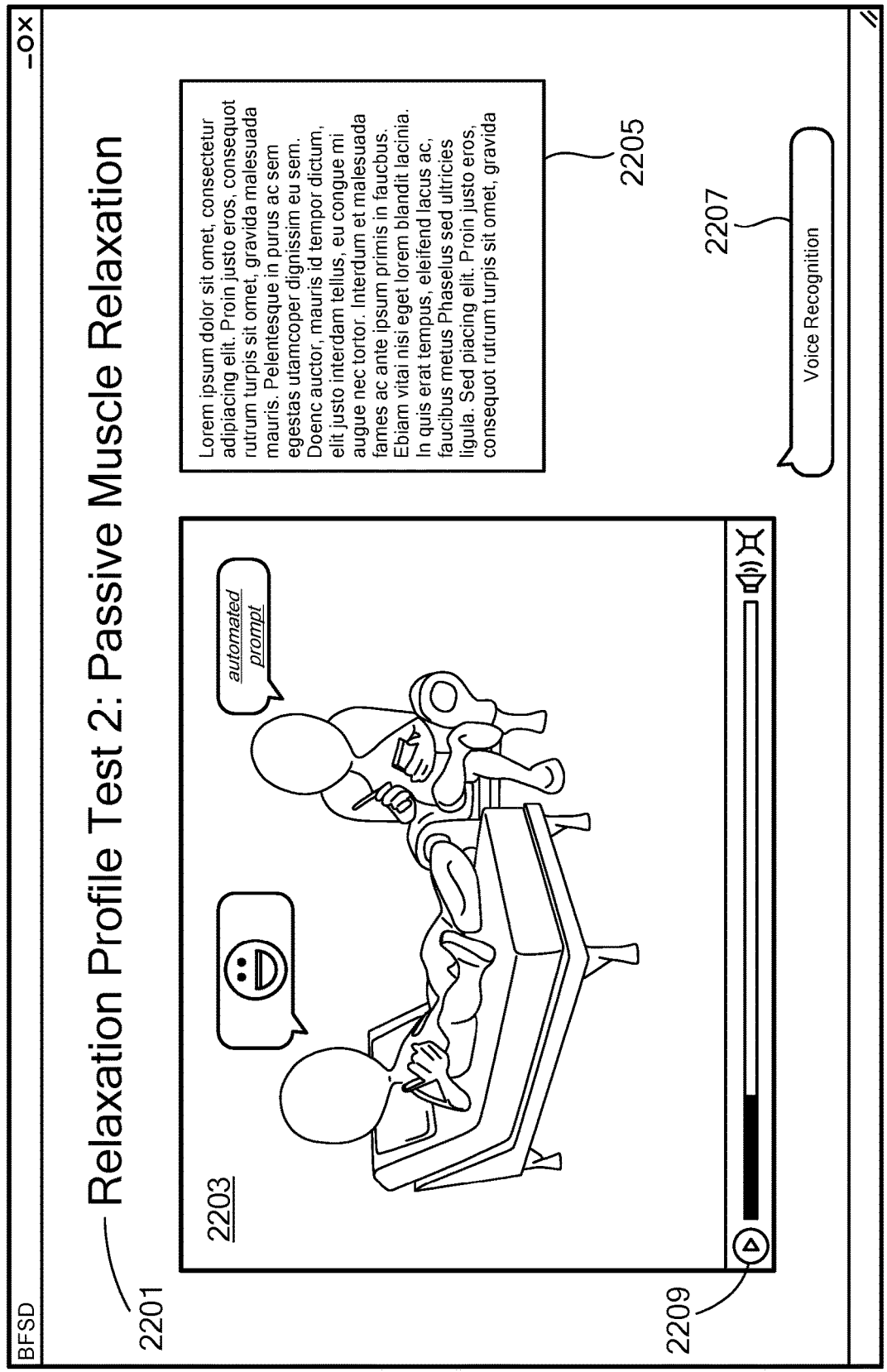
FIG. 22 is a representation of a screen display associated with testing, for effectiveness of passive muscle relaxation for use in a relaxation protocol, established and monitored by the program of FIG. 13.

FIG. 22 is a representation of a screen display associated with testing, for effectiveness of passive muscle relaxation for use in a relaxation protocol, established and monitored by the program of FIG. 13. On this screen, the subject is presented with title 2201 and text window 2205, which provides the subject with instructions on how undergo the relaxation-inducing protocol passive muscle relaxation 1007. Window 2203 provides the subject with a visual representation of an individual undergoing passive muscle relaxation exercises with a practitioner, who now and again may provide the subject with audio and visual prompts, controlled by volume control 2209. Button 2207 optionally allows the subject to enable voice recognition capabilities.

Figure 23:
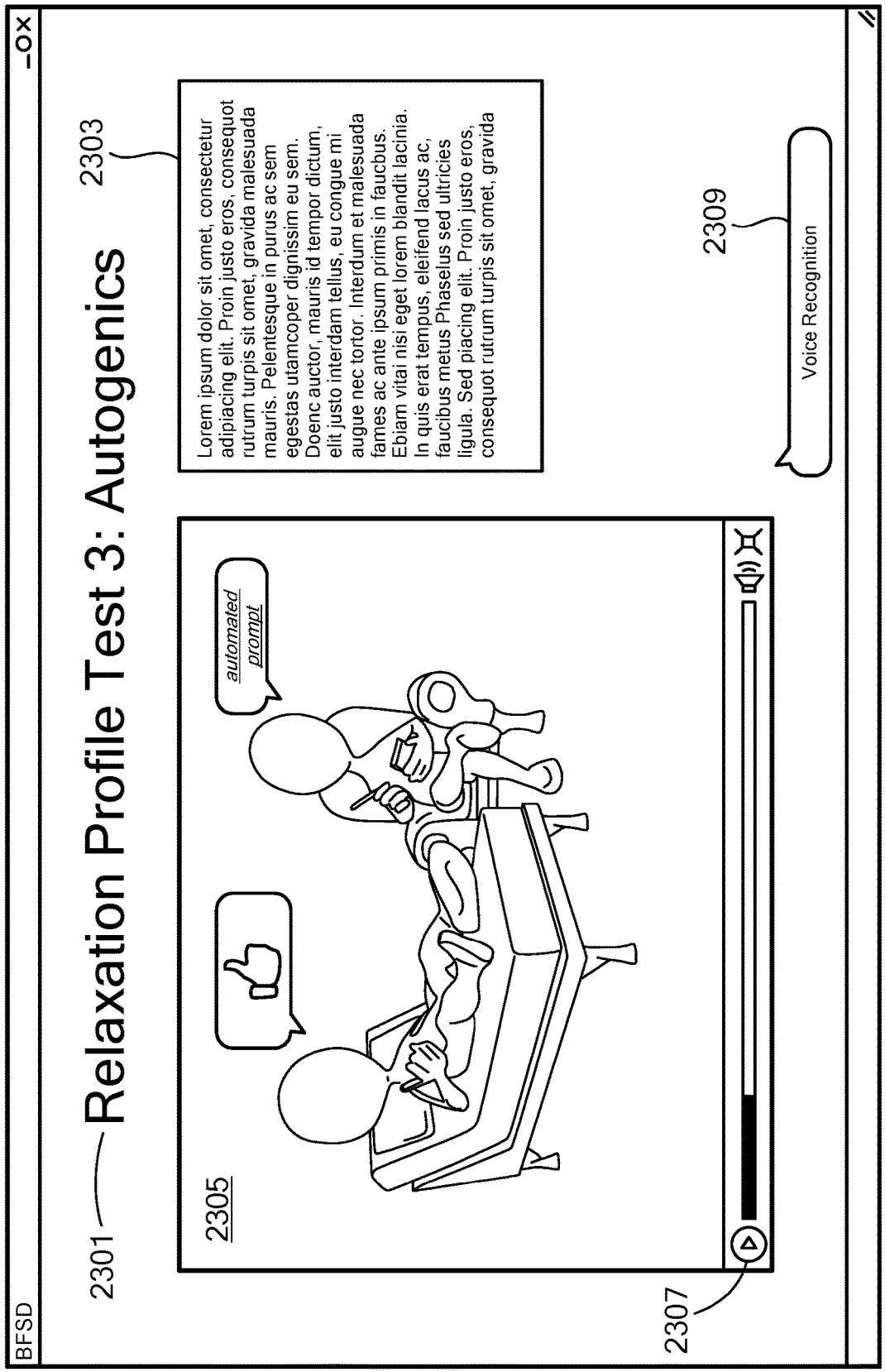
FIG. 23 is a representation of a screen display associated with testing, for effectiveness of autogenics for use in a relaxation protocol, established and monitored by the program of FIG. 13.

FIG. 23 is a representation of a screen display associated with testing, for effectiveness of autogenics for use in a relaxation protocol, established and monitored by the program of FIG. 13. On this screen, the subject is presented with title 2301 and text window 2303, which provides the subject with instructions on how undergo the relaxation-inducing protocol autogenics 1011. Window 2305 provides the subject with a visual representation of an individual undergoing autogenics exercises with a practitioner, who now and again may provide the subject with audio and visual prompts, controlled by volume control 2307. Button 2309 optionally allows the subject to enable voice recognition capabilities.

Figure 24:
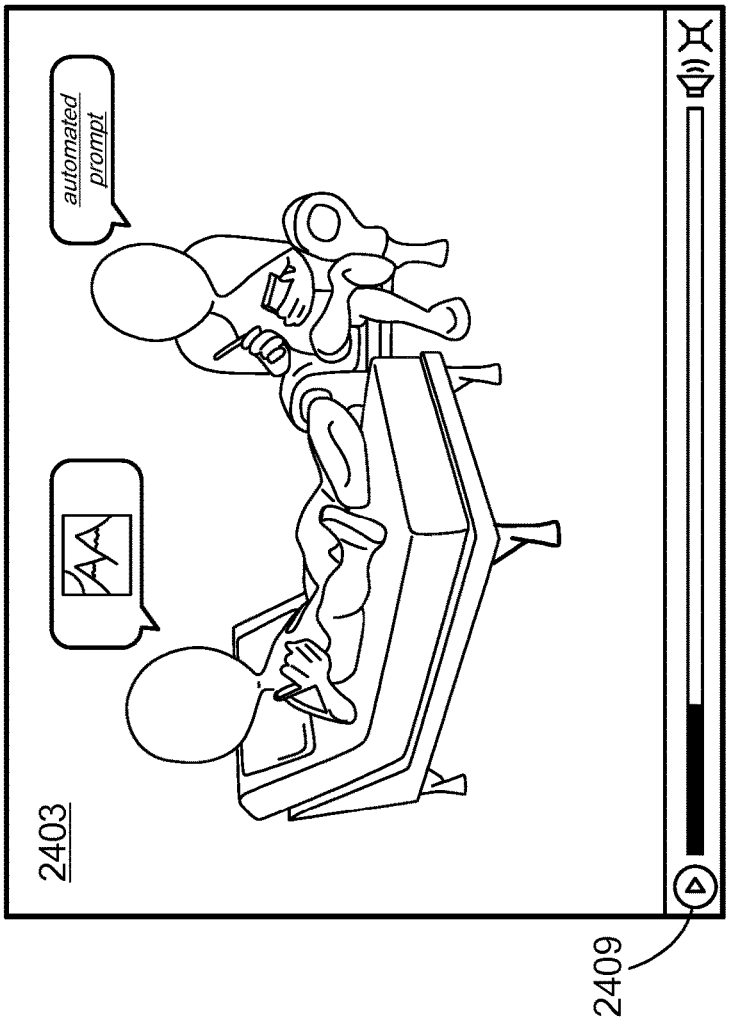
FIG. 24 is a representation of a screen display associated with testing, for effectiveness of guided imagery for use in a relaxation protocol, established and monitored by the program of FIG. 13.

FIG. 24 is a representation of a screen display associated with testing, for effectiveness of guided imagery for use in a relaxation protocol, established and monitored by the program of FIG. 13. On this screen, the subject is presented with title 2401 and text window 2405, which provides the subject with instructions on how undergo the relaxation-inducing protocol guided imagery 1015. Window 2403 provides the subject with a visual representation of an individual undergoing guided imagery exercises with a practitioner, who now and again may provide the subject with audio and visual prompts, controlled by volume control 2409. Button 2407 optionally allows the subject to enable voice recognition capabilities.

Figure 25:
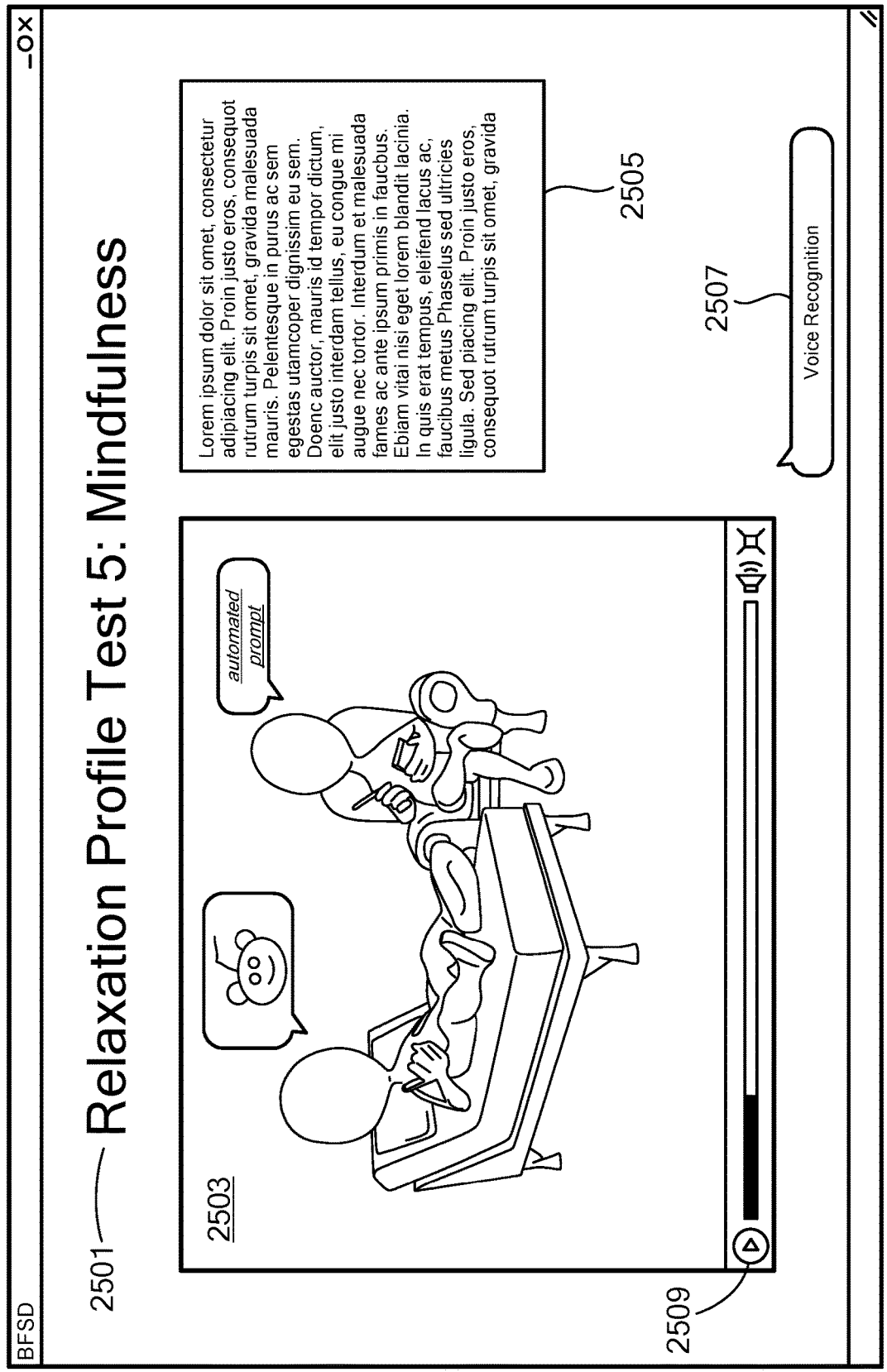
FIG. 25 is a representation of a screen display associated with testing, for effectiveness of mindfulness for use in a relaxation protocol, established and monitored by the program of FIG. 13.

FIG. 25 is a representation of a screen display associated with testing, for effectiveness of mindfulness for use in a relaxation protocol, established and monitored by the program of FIG. 13. On this screen, the subject is presented with title 2501 and text window 2505, which provides the subject with instructions on how undergo the relaxation-inducing protocol mindfulness 1019. Window 2503 provides the subject with a visual representation of an individual undergoing mindfulness exercises with a practitioner, who now and again may provide the subject with audio and visual prompts, controlled by volume control 2509. Button 2507 optionally allows the subject to enable voice recognition capabilities.

Figure 26:
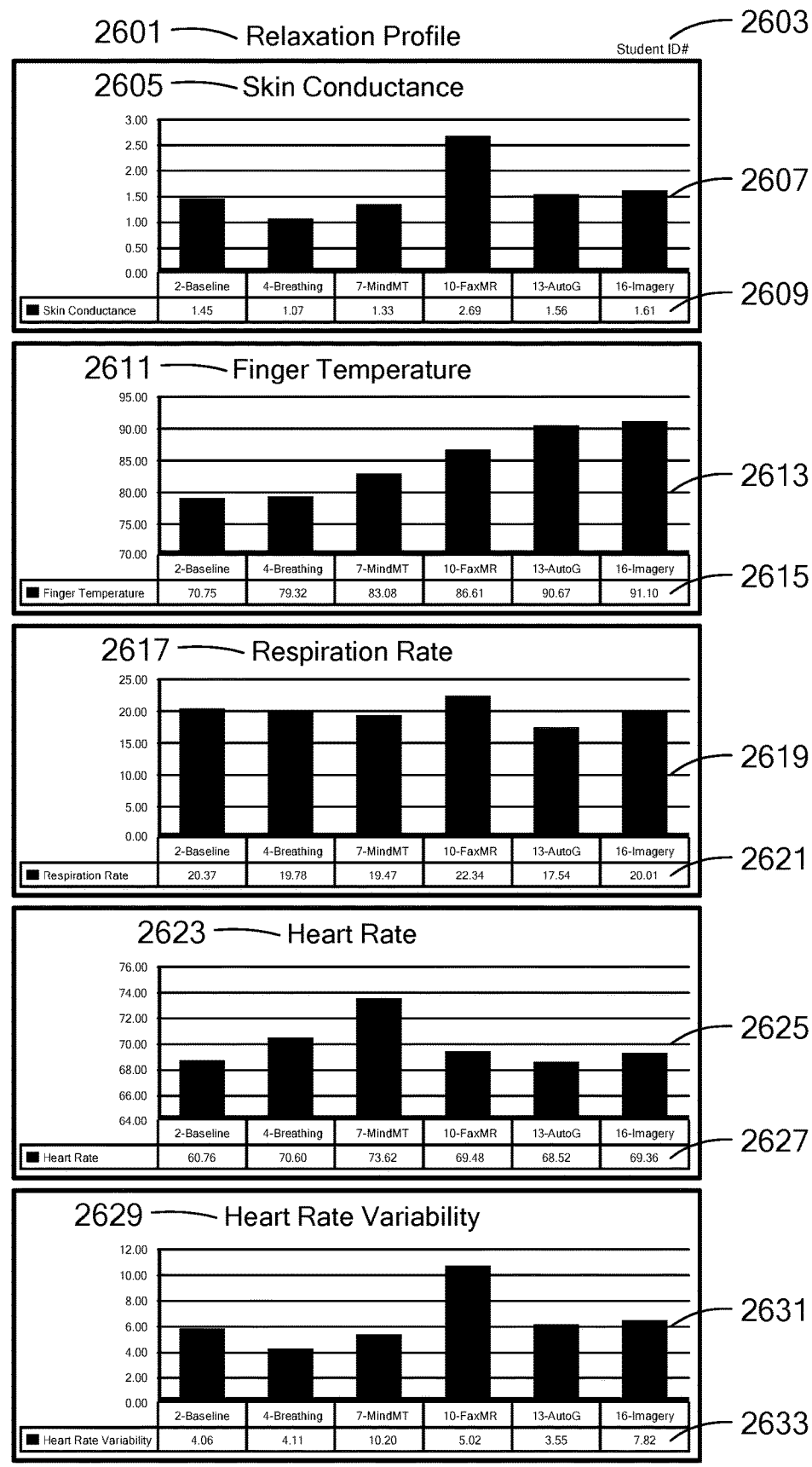
FIG. 26 is a representation of a display of a relaxation profile screen, wherein the results of activities associated with FIGS. 21-25 are summarized and presented visually to the subject by the program of FIG. 13.

FIG. 26 is a representation of a display of a relaxation profile screen, wherein the results of activities associated with FIGS. 21-25 are summarized and presented visually to the subject by the program of FIG. 13. On this screen, the subject is presented with title 2601 and user ID #2603. Title 2605, visual image 2607, and text boxes 2609 present the subject with information regarding the subject's skin conductance measurements over the activities in Relaxation Profile testing associated with FIG. 10. Title 2611, visual image 2613, and text boxes 2615 present the subject with information regarding the subject's skin temperature measurements over the activities in Relaxation Profile testing associated with FIG. 10. Title 2617, visual image 2619, and text boxes 2621 present the subject with information regarding the subject's respiration rate measurements over the activities in Relaxation Profile testing associated with FIG. 10. Title 2623, visual image 2625, and text boxes 2627 present the subject with information regarding the subject's heart rate measurements over the activities in Relaxation Profile testing associated with FIG. 10. Title 2629, visual image 2631, and text boxes 2633 present the subject with information regarding the subject's heart rate variability measurements over the activities in Relaxation Profile testing associated with FIG. 10.

Figure 27:
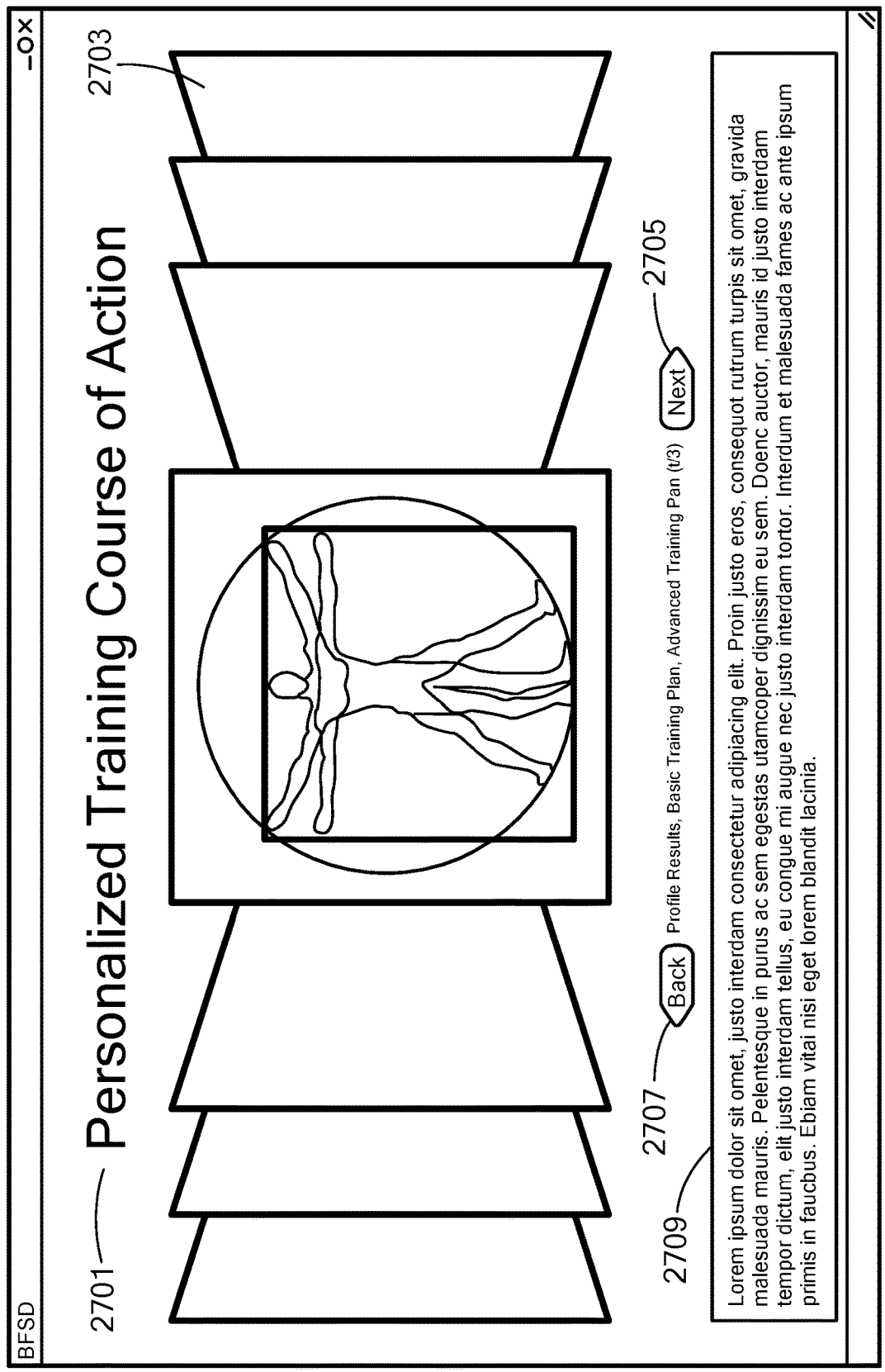
FIG. 27 is a representation of a screen display detailing a synthesized summary of the results associated with FIGS. 20 and 26, together with an detailed course of action that the subject will be caused to follow over subsequent iterations of the program of FIG. 13.

FIG. 27 is a representation of a screen display detailing a synthesized summary of the results associated with FIGS. 20 and 26, together with a detailed course of action that the subject will be caused to follow over subsequent iterations of the program of FIG. 13. On this screen, the subject is presented with title 2701 and text box 2709, wherein the subject is presented with a detailed analysis and explanation of the Stress Profile testing associated with FIG. 9, Relaxation Profile testing associated with FIG. 10, and a synthesis thereof. Image scroll 2703 presents the subject with a visual representation of the information provided in textbox 2709. Buttons 2705 and 2707 enable the subject to scroll between images in the image scroll 2703.

Figure 28:
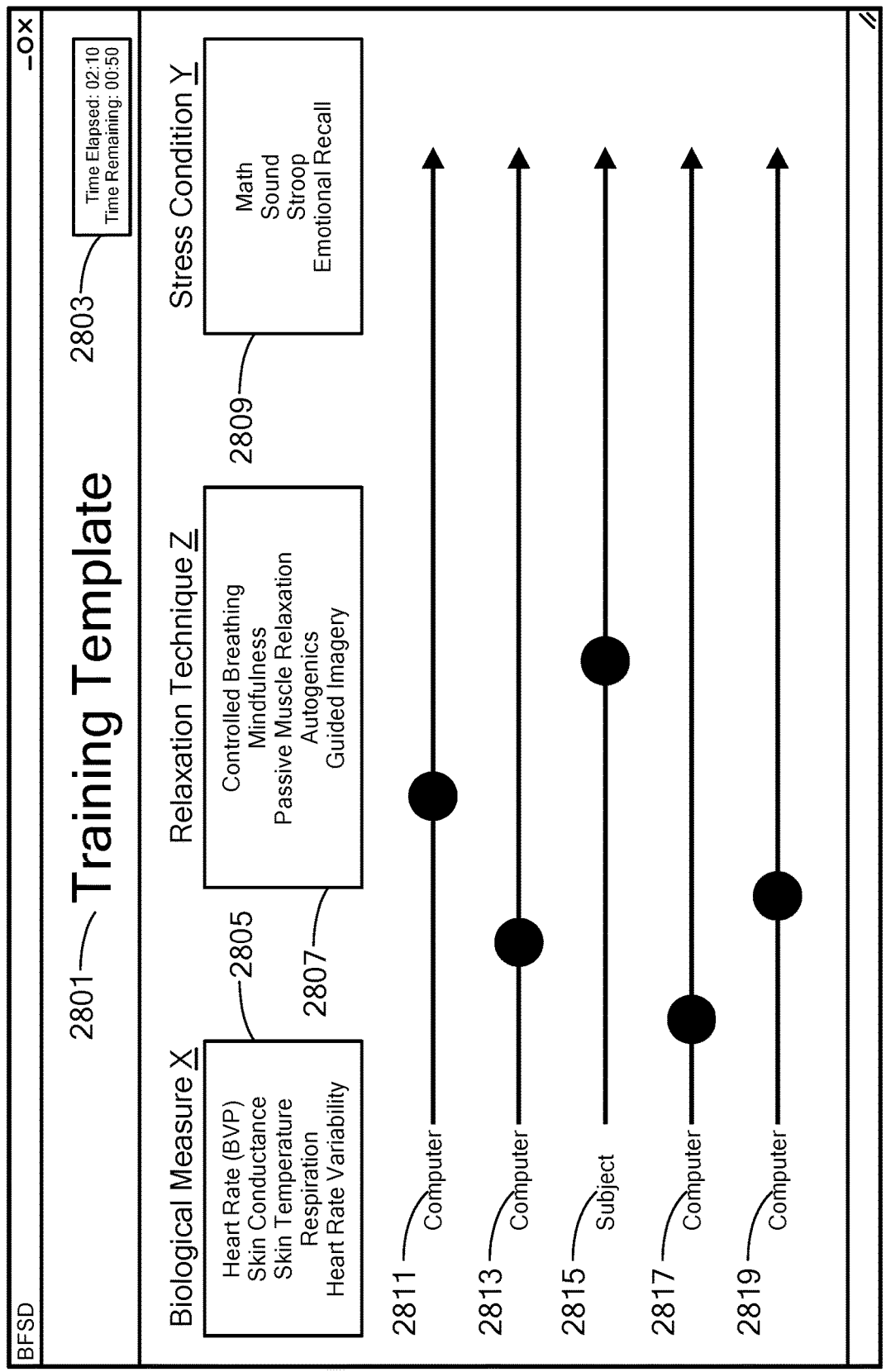
FIG. 28 is a representation of a screen display providing a visual template for the course of action associated with FIG. 27 by the program of FIG. 13.

FIG. 28 is a representation of a screen display providing a visual template for the course of action associated with FIG. 27 by the program of FIG. 13. On this screen, the subject is presented with title 2801 and box 2803, which displays time elapsed and time remaining (in minutes and seconds) for a particular training module. Window 2805 displays information pertaining to the subject's selected stress-indicating physiological parameter. Window 2807 displays information pertaining to the subject's selected relaxation protocol. Window 2809 displays information pertaining to the subject's selected stress-inducing activity. Arrow bars 2811, 2813, 2815, 2817, and 2819, taken together, present the subject with a simulated race challenge, wherein the subject attempts to affect user ball 2815 to reach the end of its arrow bar before balls 2811, 2813, 2817, and 2819 (opponent balls) reach the end of their respective arrow bars. The manner by which all balls move along their respective arrow lines is a function of the magnitude of discrepancy between the subject's stress condition measurements and a specified baseline measurement of the selected stress-indicating physiological parameter. The closer the subject's stress-condition measurement is to the target baseline measurement, the more likely the subject's ball 2815 will reach the end of its arrow line before the opponent balls 2811, 2813, 2817, and 2819 reach the end of their respective arrow lines.

Figure 29:
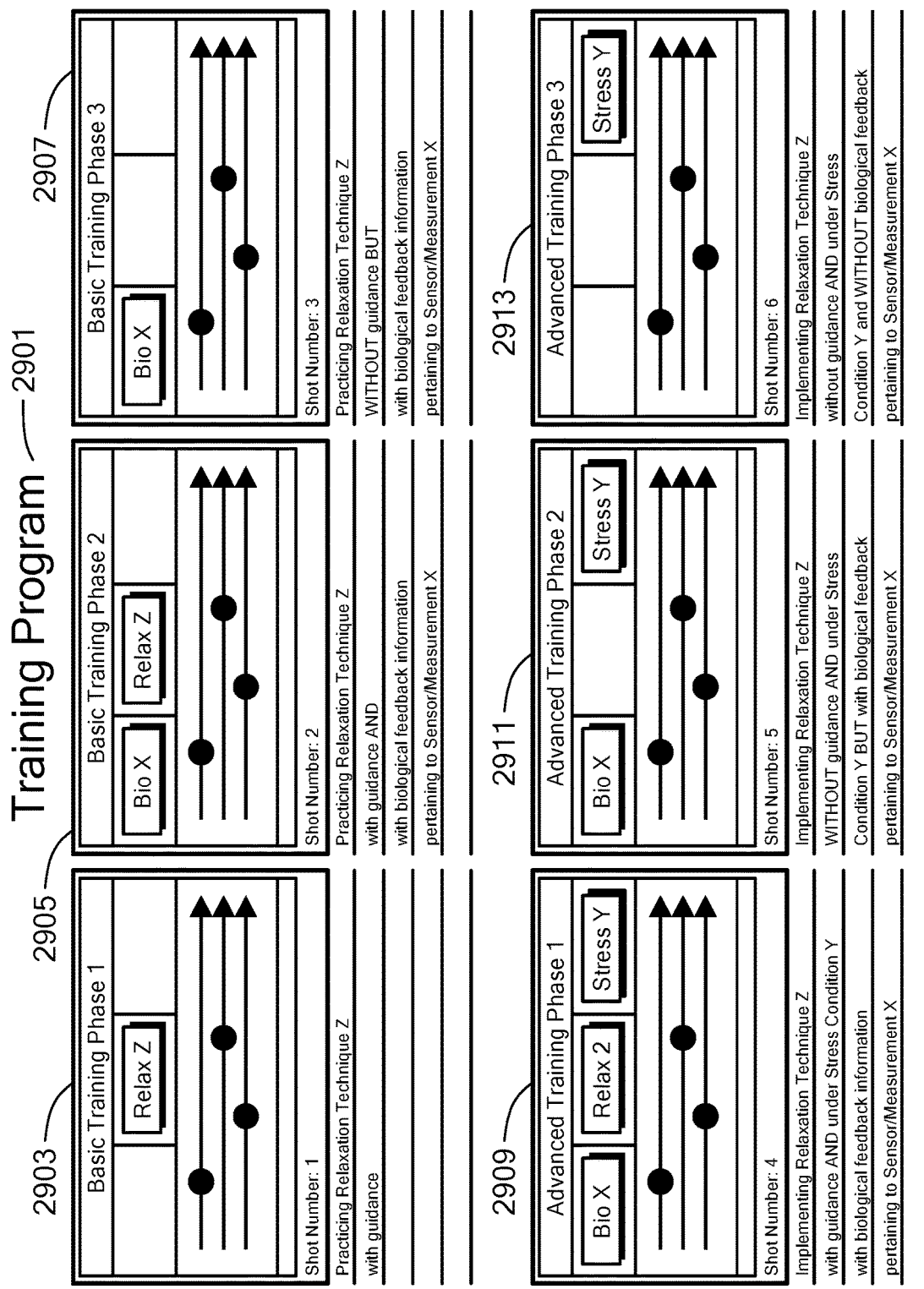
FIG. 29 is a representation of a visual progression of training sessions associated with the course of action presented in FIG. 27 that the subject will experience in a sequenced manner as a function of the program of FIG. 13, from Basic Training I, II, and III through Advanced Training I, II, and III.

FIG. 29 is a representation of a visual progression of training sessions associated with the course of action presented in FIG. 27 that the subject will experience in a sequenced manner as a function of the program of FIG. 13, from Basic Training I, II, and III through Advanced Training I, II, and III. This screen contains title 2901 and six sequenced training phase images: 2903, 2905, 2907, 2909, 2911 and 2913, respectively. Image 2903 represents a display of Basic Training session I, wherein the subject will undergo processes 1101 and 1103, with the results thereof to be presented real-time to the subject in the race game associated with FIG. 28 (items 2811-2819). Image 2905 represents a display of Basic Training session II, wherein the subject will undergo processes 1105 and 1107, with the results thereof to be presented real-time to the subject in the race game associated with FIG. 28 (items 2811-2819). Image 2907 represents a display of Basic Training session III, wherein the subject will undergo processes 1109 and 1111, with the results thereof to be presented real-time to the subject in the race game associated with FIG. 28 (items 2811-2819).

Image 2909 represents a display of Advanced Training session I, wherein the subject will undergo processes 1201 and 1203, with the results thereof to be presented real-time to the subject in the race game associated with FIG. 28 (items 2811-2819). Image 2911 represents a display of Advanced Training session II, wherein the subject will undergo processes 1205 and 1207, with the results thereof to be presented real-time to the subject in the race game associated with FIG. 28 (items 2811-2819). Image 2911 represents a display of Advanced Training session III, wherein the subject will undergo processes 1209 and 1211, with the results thereof to be presented real-time to the subject in the race game associated with FIG. 28 (items 2811-2819).

Figure 30:
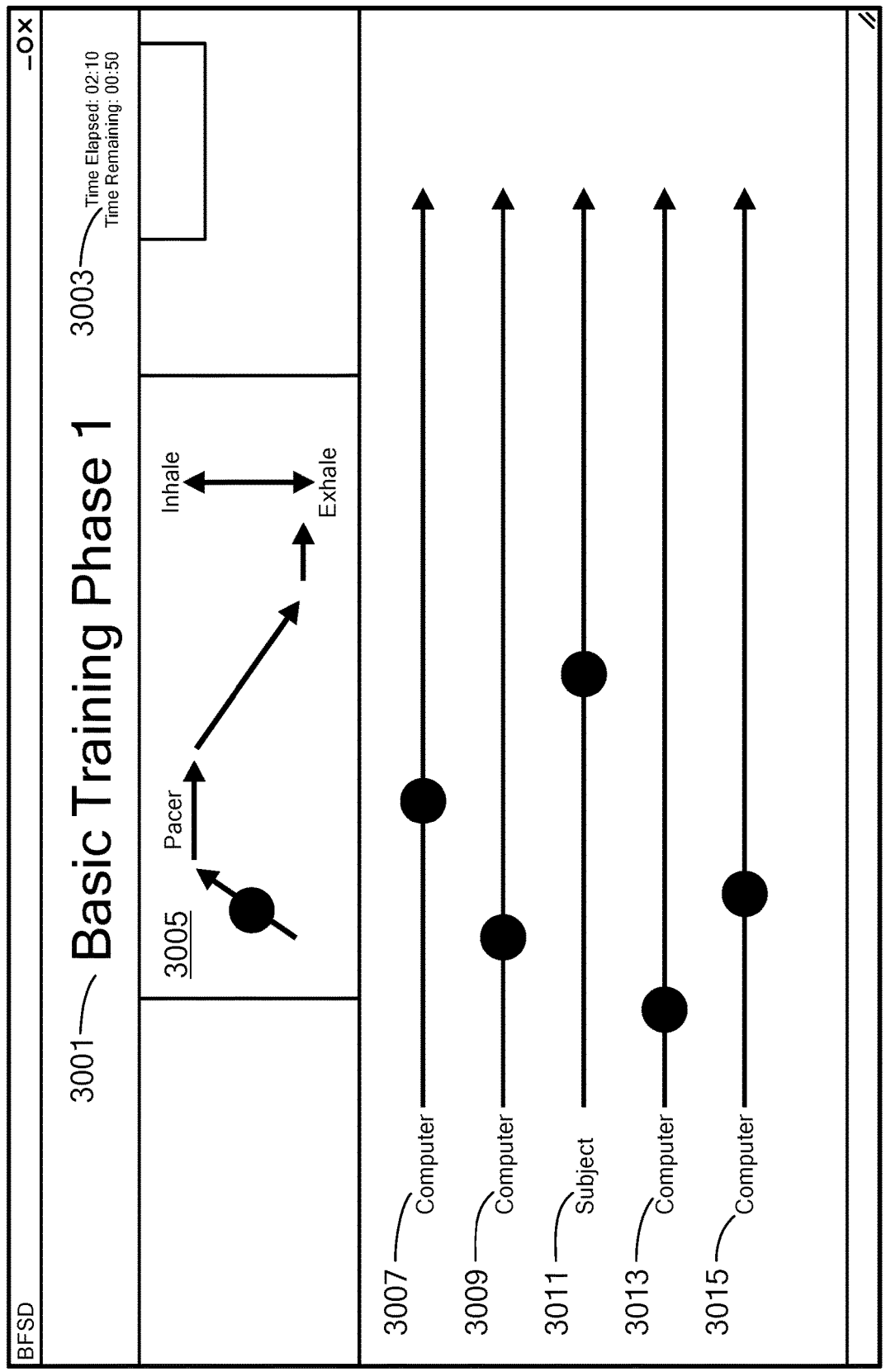
FIG. 30 is a representation of a screen display associated with the first of three basic training sessions that the subject will undergo as established by the course of action associated with FIG. 27 by the program of FIG. 13.

FIG. 30 is a representation of a screen display associated with the first of three basic training sessions that the subject will undergo as established by the course of action associated with FIG. 27 by the program of FIG. 13. On this screen, the subject is presented with title 3001 and timer window 3003. Window 3005 provides the subject with a visual representation of a pacer for controlled breathing, by which the subject is provided visual information regarding how closely he or she is breathing in sync with a specified respiration rate. Arrow line and ball images 3007, 3009, 3011, 3013, and 3015 together represent a visual image of the race game associated with FIG. 28 (items 2811-2819).

Figure 31:
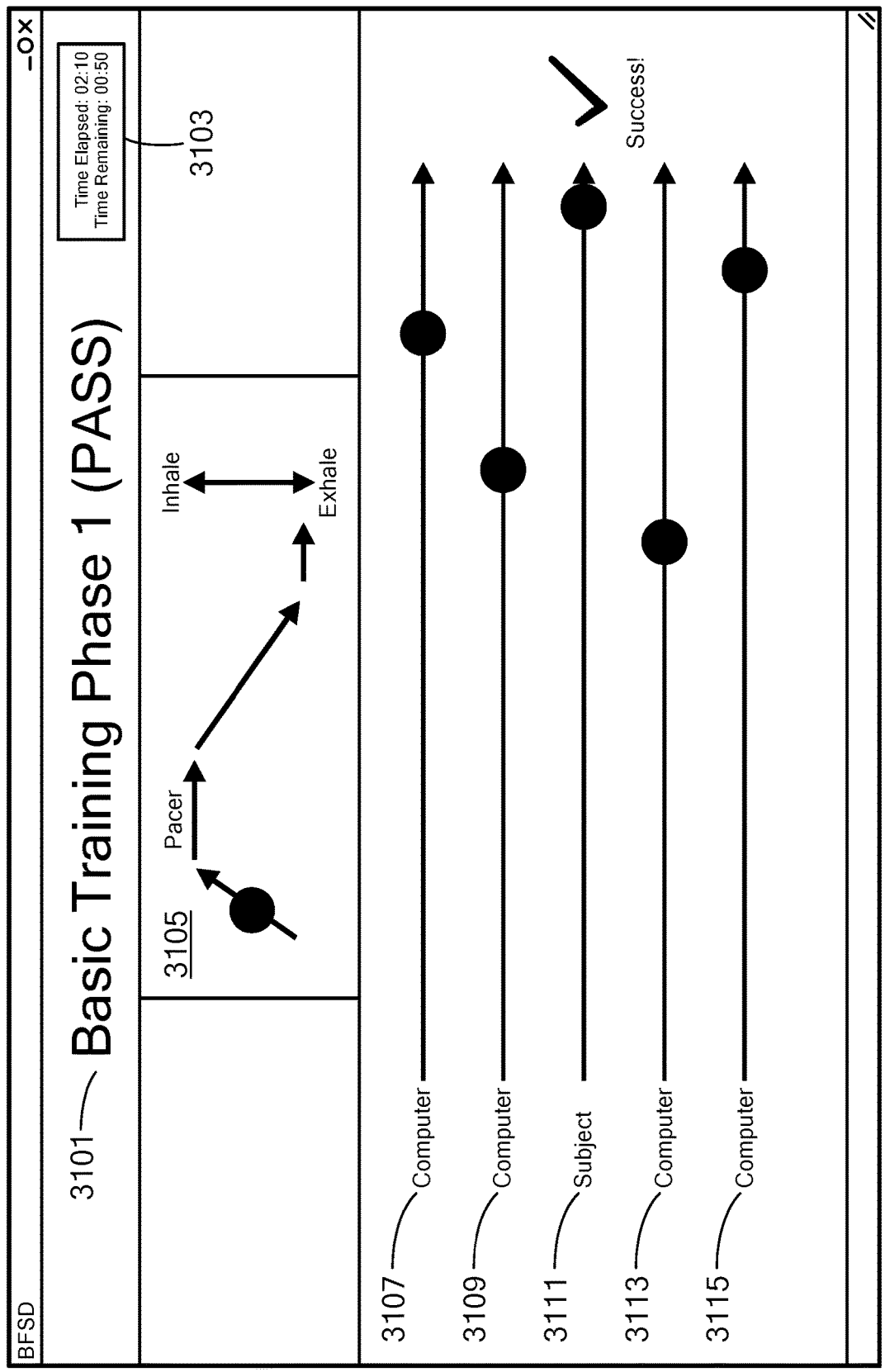
FIG. 31 is a representation of a screen display associated with the subject's attainment of a specific goal, established by the results associated with FIGS. 20, 26, and 27, during the first of three basic training sessions that the subject will undergo as established by the course of action associated with FIG. 27 by the program of FIG. 13.

FIG. 31 is a representation of a screen display associated with the subject's attainment of a specific goal, established by the results associated with FIGS. 20, 26, and 27, during the first of three basic training sessions that the subject will undergo as established by the course of action associated with FIG. 27 by the program of FIG. 13. On this screen, the subject is presented with title 3101 and timer window 3103. Window 3105 provides the subject with a visual representation of a pacer for controlled breathing, by which the subject is provided visual information regarding how closely he or she is breathing in sync with a specified respiration rate. Arrow line and ball images 3107, 3109, 3111, 3113, and 3115 together represent a visual image of the race game associated with FIG. 28 (items 2811-2819). In this screen display, ball 3111 has reached the end of its arrow before balls 3107, 3109, 3113, and 3115 have reached the end of their respective arrow lines, the result of which represents the subject's attaining a specified goal and passing the training phase.

Figure 32:
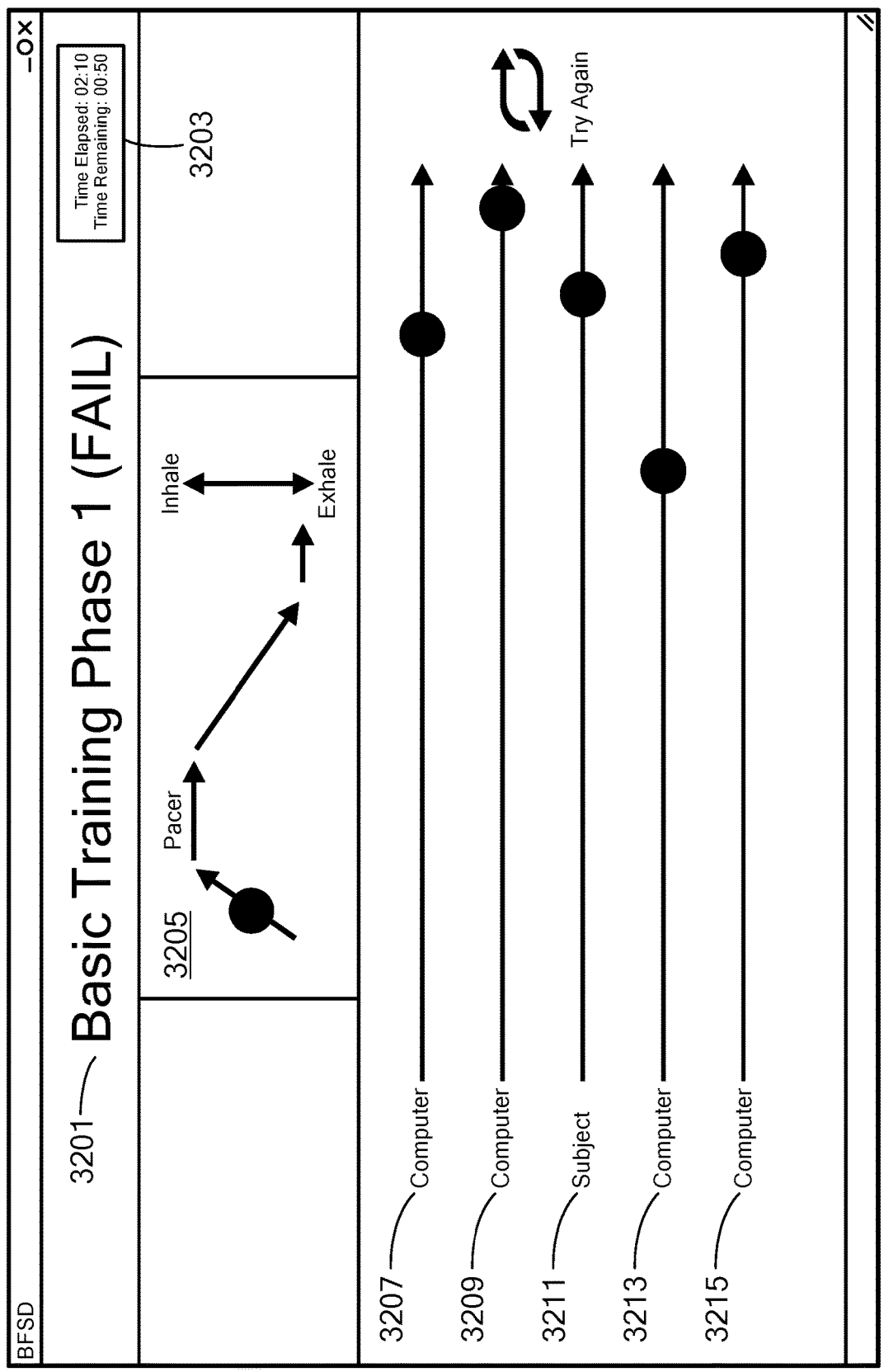
FIG. 32 is a representation of a screen display associated with the subject's failure to attain a specified goal, established by the results associated with FIGS. 20, 26, and 27, during the first of three basic training sessions that the subject will undergo as established by the course of action associated with FIG. 27 by the program of FIG. 13.

FIG. 32 is a representation of a screen display associated with the subject's failure to attain a specified goal, established by the results associated with FIGS. 20, 26, and 27, during the first of three basic training sessions that the subject will undergo as established by the course of action associated with FIG. 27 by the program of FIG. 13. On this screen, the subject is presented with title 3201 and timer window 3203. Window 3205 provides the subject with a visual representation of a pacer for controlled breathing, by which the subject is provided visual information regarding how closely he or she is breathing in sync with a specified respiration rate. Arrow line and ball images 3207, 3209, 3211, 3213, and 3215 together represent a visual image of the race game associated with FIG. 28 (items 2811-2819). In this screen display, ball 3209 has reached the end of its arrow before balls 3207, 3211, 3213, and 3215 have reached the end of their respective arrow lines, the result of which represents the subject's not attaining a specified goal and not passing the training phase.

Figure 33:
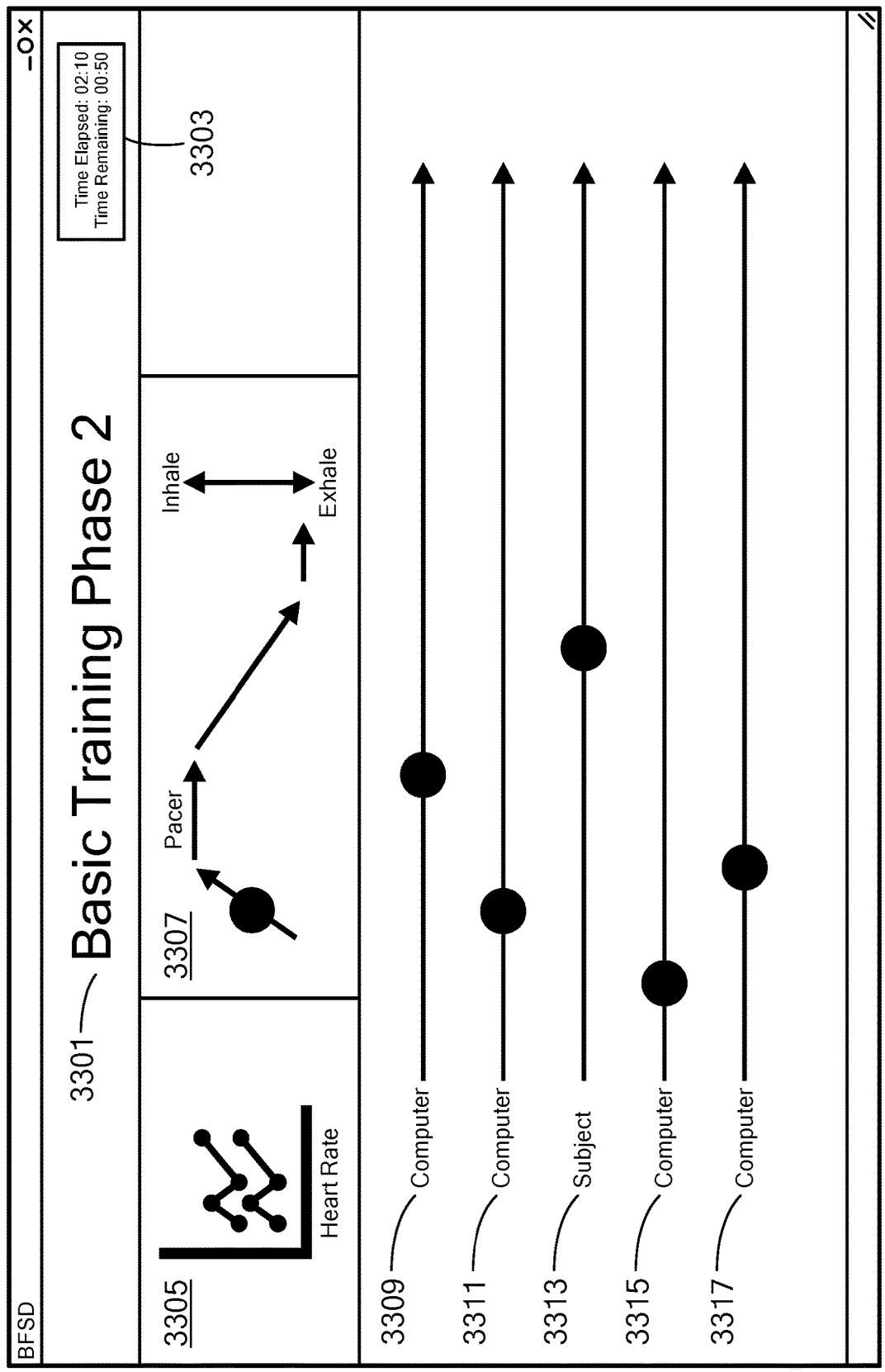
FIG. 33 is a representation of screen display associated with the second of three basic training sessions that the subject will undergo as established by the course of action associated with FIG. 27 by the program of FIG. 13.

FIG. 33 is a representation of screen display associated with the second of three basic training sessions that the subject will undergo as established by the course of action associated with FIG. 27 by the program of FIG. 13. On this screen, the subject is presented with title 3301 and timer window 3303. Window 3305 provides the subject with a visual representation of a pacer for controlled breathing, by which the subject is provided visual information regarding how closely he or she is breathing in sync with a specified respiration rate. Window 3305 provides the subject with a visual representation of his or her selected stress-indicating physiological parameter. Arrow line and ball images 3309, 3311, 3313, 3315, and 3317 together represent a visual image of the race game associated with FIG. 28 (items 2811-2819).

Figure 34:
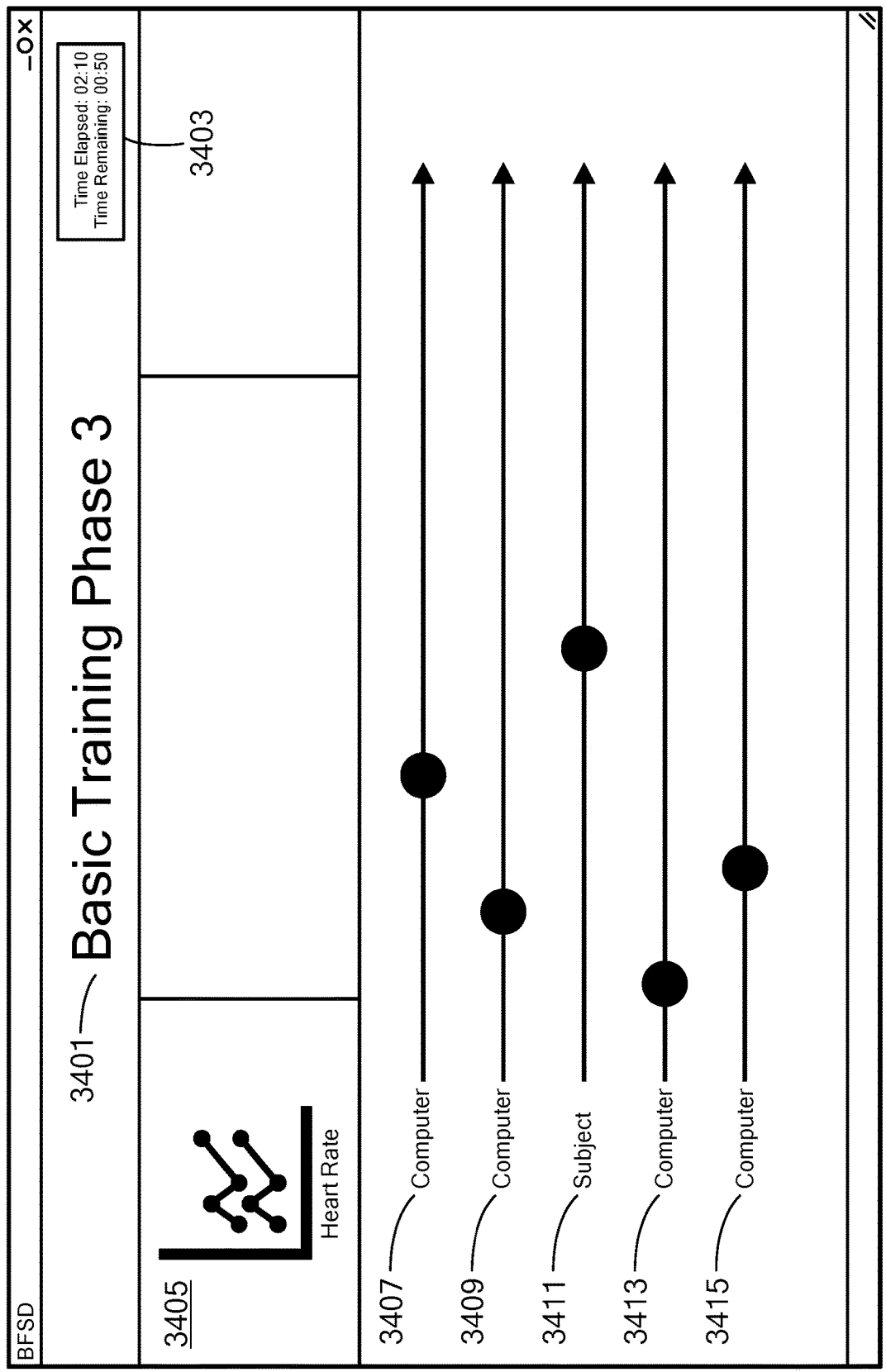
FIG. 34 is a representation of a screen display associated with the third of three basic training sessions that the subject will undergo as established by the course of action associated with FIG. 27 by the program of FIG. 13.

FIG. 34 is a representation of a screen display associated with the third of three basic training sessions that the subject will undergo as established by the course of action associated with FIG. 27 by the program of FIG. 13. On this screen, the subject is presented with title 3401 and timer window 3403. Window 3405 provides the subject with a visual representation of his or her selected stress-indicating physiological parameter. Arrow line and ball images 3407, 3409, 3411, 3413, and 3415 together represent a visual image of the race game associated with FIG. 28 (items 2811-2819).

Figure 35:
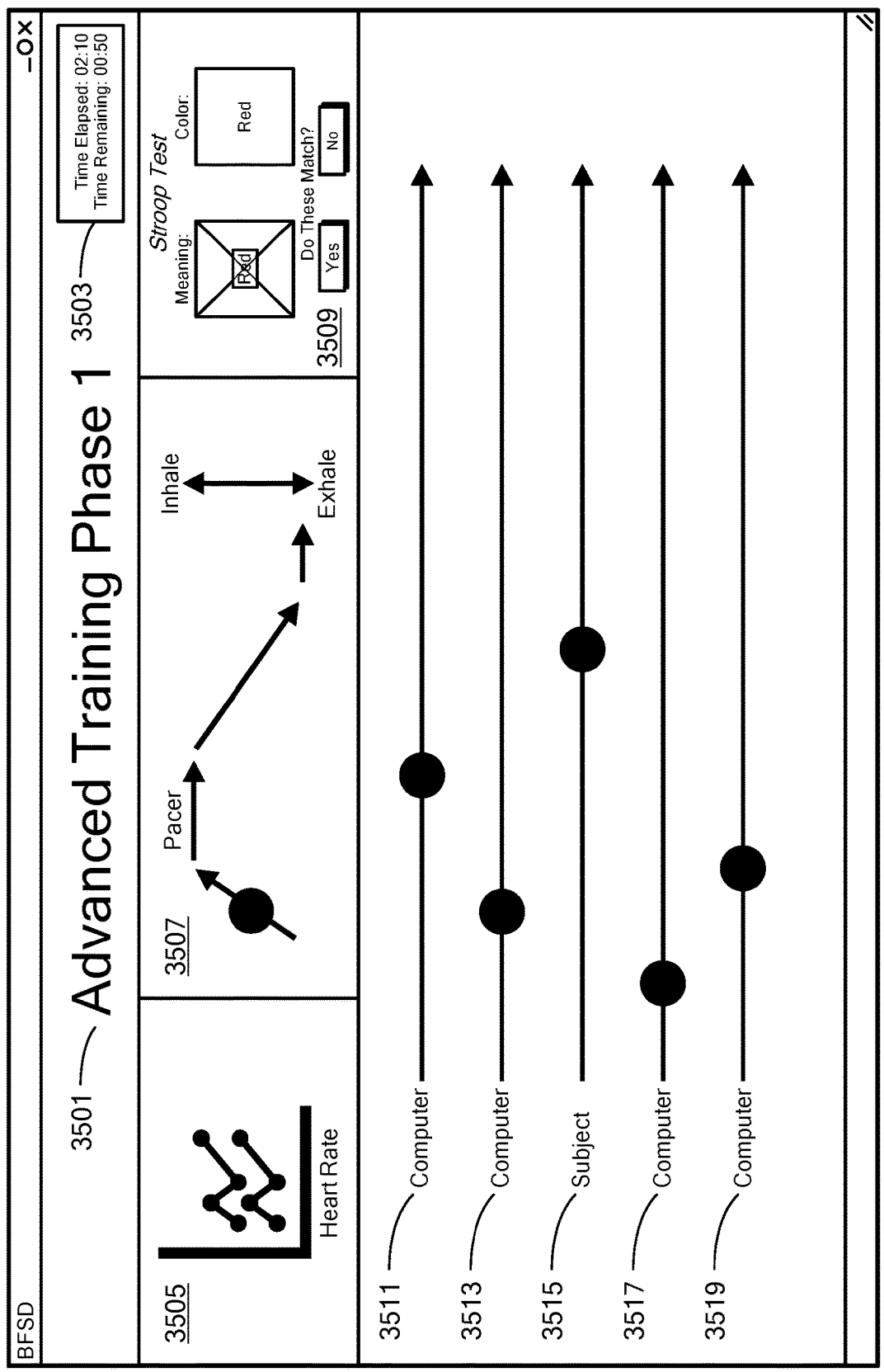
FIG. 35 is a representation of a screen display associated with the first of three advanced training sessions that the subject will undergo as established by the course of action associated with FIG. 27 by the program of FIG. 13.

FIG. 35 is a representation of a screen display associated with the first of three advanced training sessions that the subject will undergo as established by the course of action associated with FIG. 27 by the program of FIG. 13. On this screen, the subject is presented with title 3501 and timer window 3503. Window 3507 provides the subject with a visual representation of a pacer for controlled breathing, by which the subject is provided visual information regarding how closely he or she is breathing in sync with a specified respiration rate. Window 3505 provides the subject with a visual representation of his or her selected stress-indicating physiological parameter. Window 3509 prompts the subject to perform the selected stress-inducing activity for a period of time. Arrow line and ball images 3511, 3513, 3515, 3517, and 3519 together represent a visual image of the race game associated with FIG. 28 (items 2811-2819).

Figure 36:
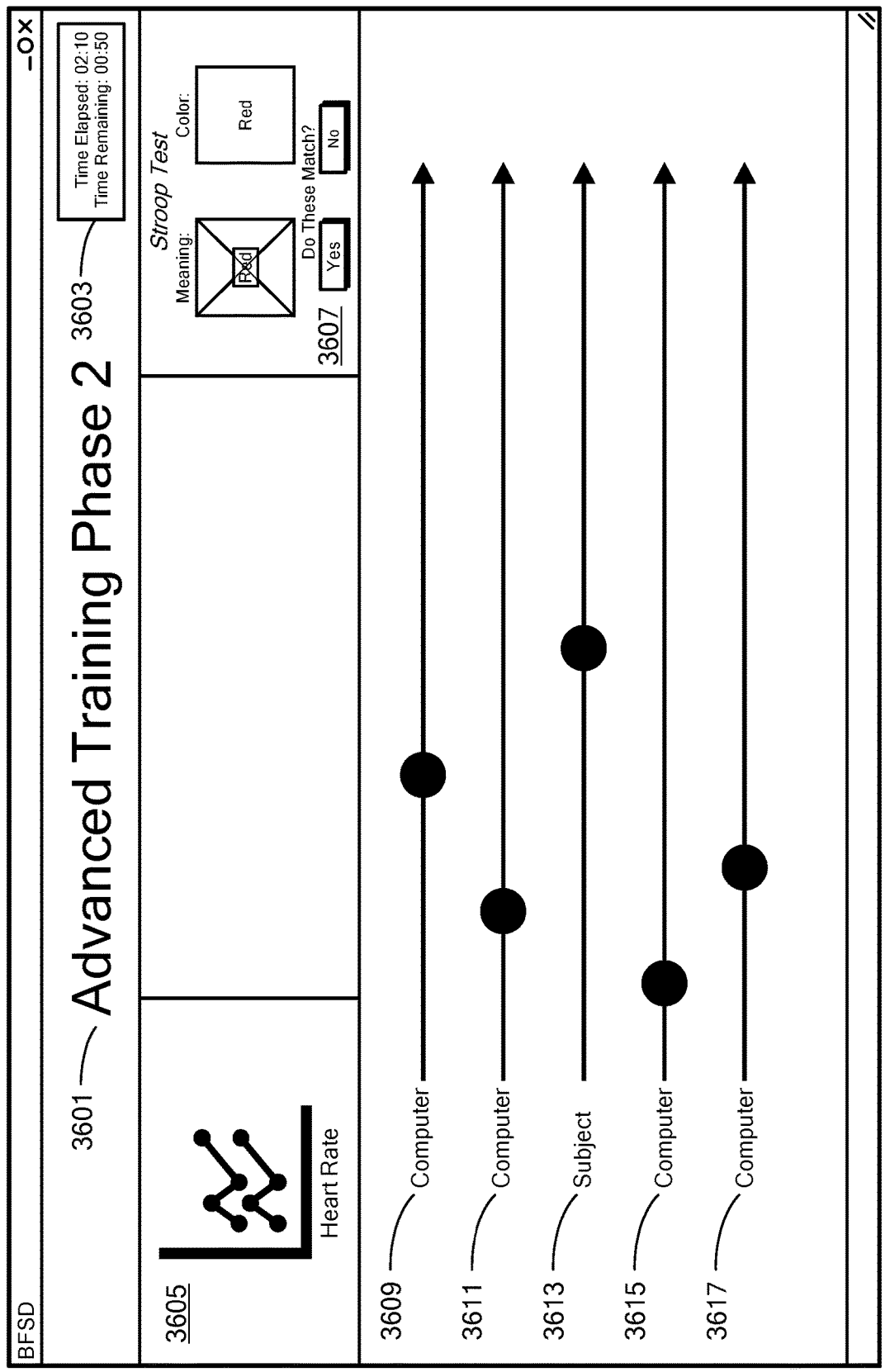
FIG. 36 is a representation of a screen display associated with the second of three advanced training sessions that the subject will undergo as established by the course of action associated with FIG. 27 by the program of FIG. 13.

FIG. 36 is a representation of a screen display associated with the second of three advanced training sessions that the subject will undergo as established by the course of action associated with FIG. 27 by the program of FIG. 13. On this screen, the subject is presented with title 3601 and timer window 3603. Window 3605 provides the subject with a visual representation of his or her selected stress-indicating physiological parameter. Window 3607 prompts the subject to perform the selected stress-inducing activity for a period of time. Arrow line and ball images 3609, 3611, 3613, 3615, and 3617 together represent a visual image of the race game associated with FIG. 28 (items 2811-2819).

Figure 37:
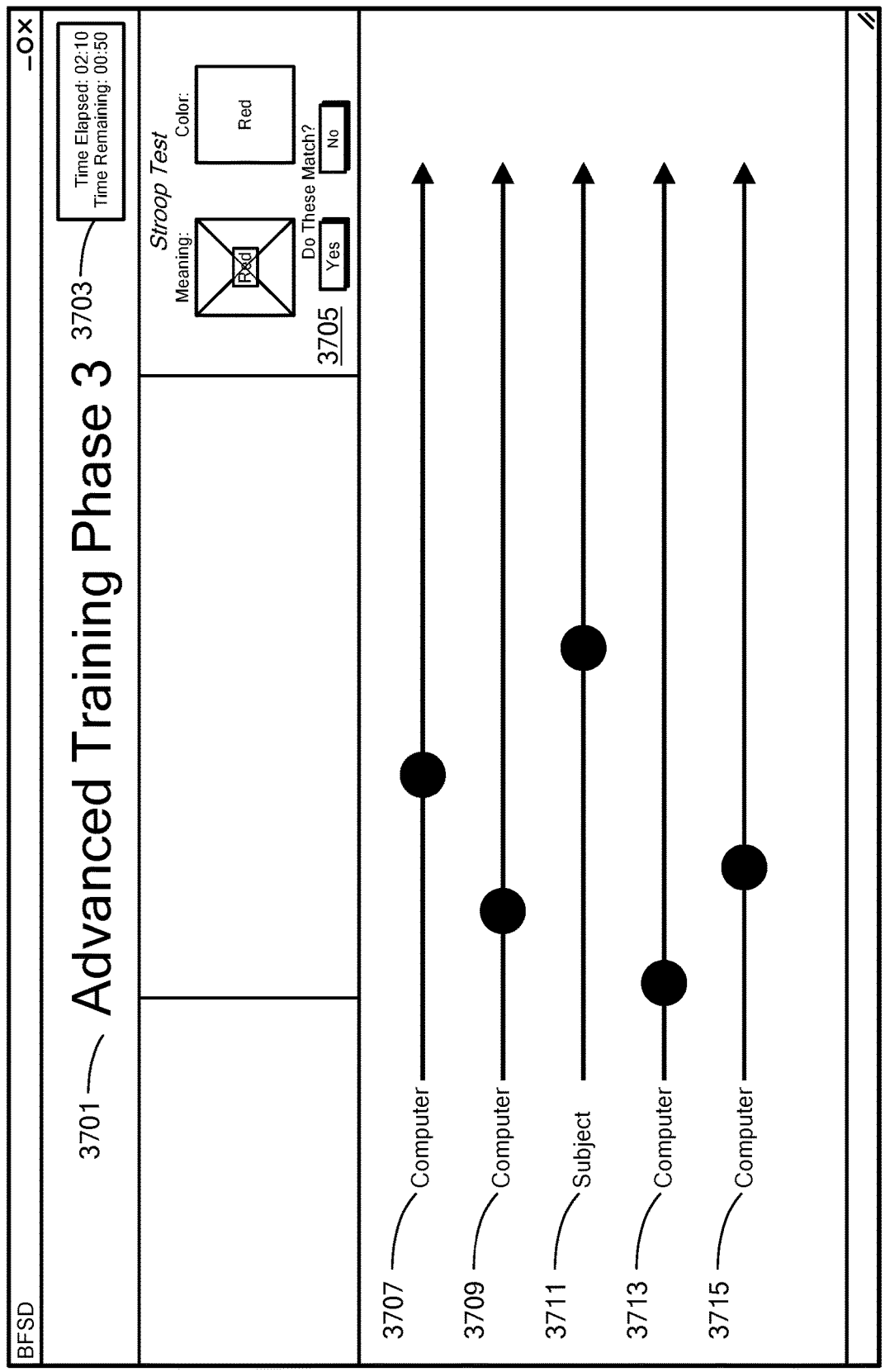
FIG. 37 is a representation of a screen display associated with the third of three advanced training sessions that the subject will undergo as established by the course of action associated with FIG. 27 by the program of FIG. 13.

FIG. 37 is a representation of a screen display associated with the third of three advanced training sessions that the subject will undergo as established by the course of action associated with FIG. 27 by the program of FIG. 13. On this screen, the subject is presented with title 3701 and timer window 3703. Window 3505 prompts the subject to perform the selected stress-inducing activity for a period of time. Arrow line and ball images 3707, 3709, 3711, 3713, and 3715 together represent a visual image of the race game associated with FIG. 28 (items 2811-2819).

Figure 38:
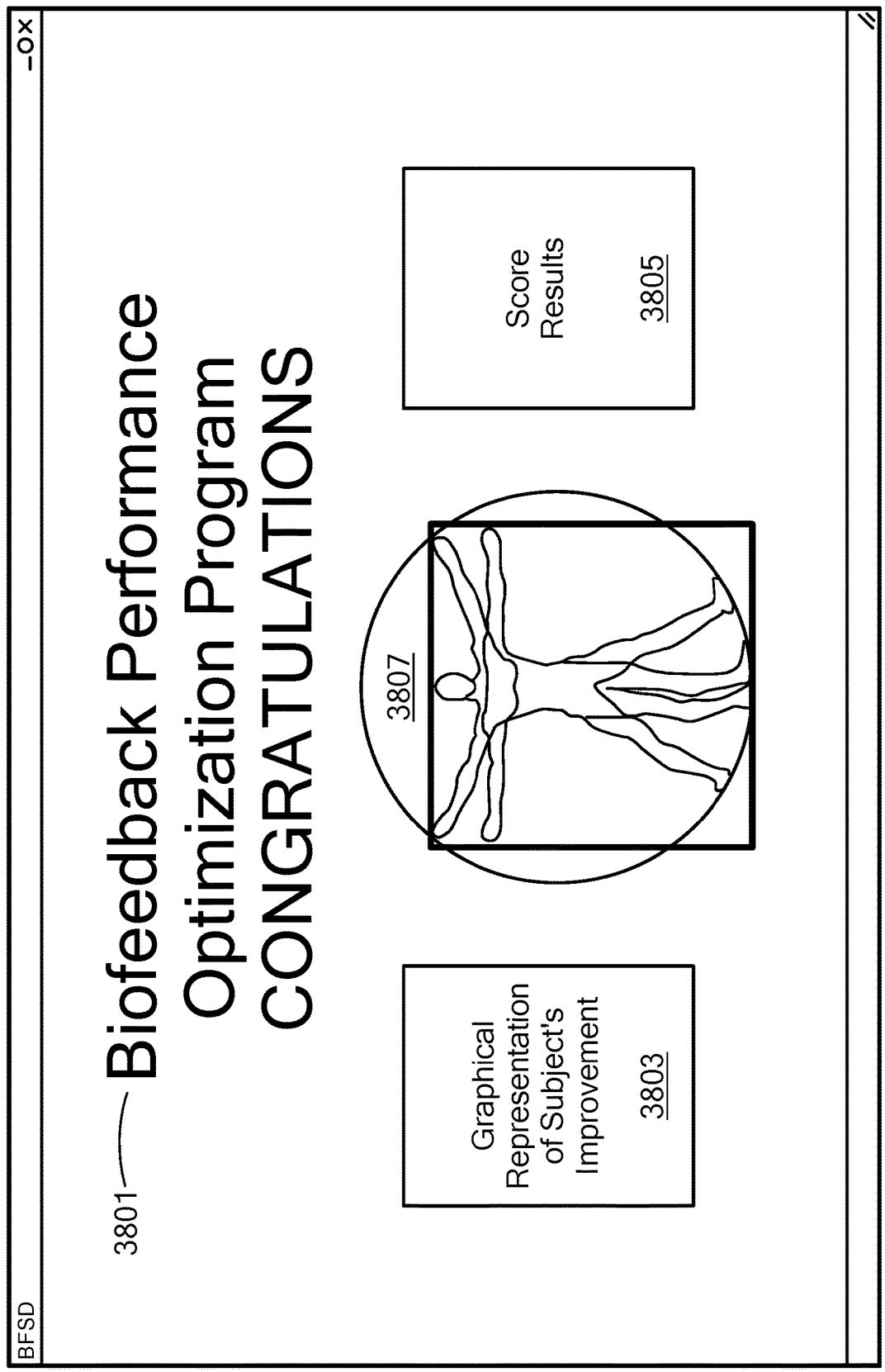
FIG. 38 is a representation of a display of an end screen by the program of FIG. 13.

FIG. 38 is a representation of a display of an end screen by the program of FIG. 13. On this screen, the subject is presented with title 3801 and company logo image 3807. Windows 3803 and 3805 provide the subject with a graphical representation of his or her progress and his or her score results, respectively, through the processes associated with FIGS. 16-19, 21-25, 30, and 33-37.

Figure 39:
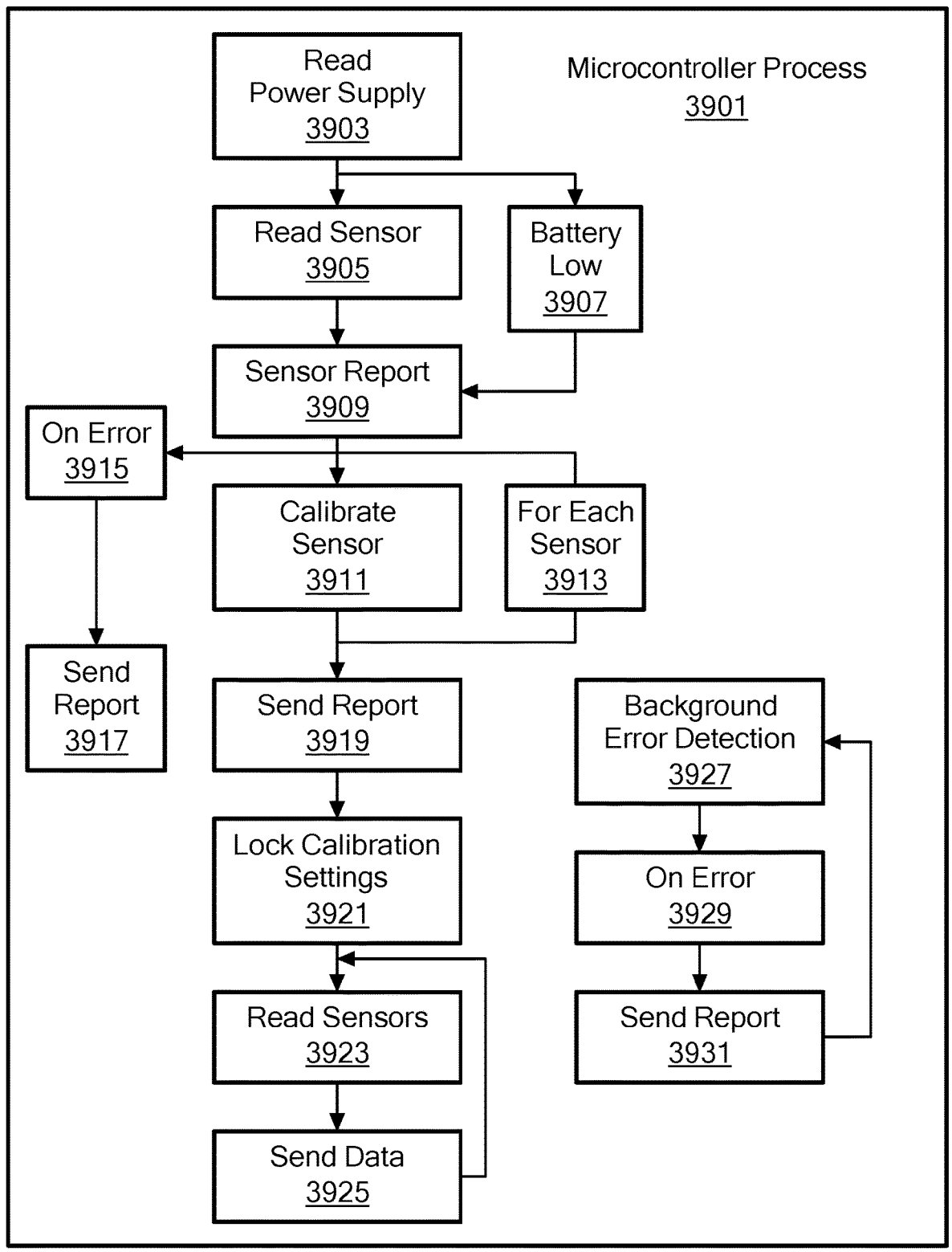
FIG. 39 is block diagram of architecture of a microcontroller process associated with the system architecture of FIG. 2, in accordance with an embodiment of the present invention, for carrying out the method embodiment of FIG. 1.

FIG. 39 schematically represents a microcontroller firmware process 3901 associated with the system architecture of FIG. 2, in accordance with an embodiment of the present invention, for carrying out the method embodiment of FIG. 1. In accordance with this embodiment, a microcontroller first carries out an initialization process. The firmware reads the microcontroller power supply in process 3903 to ensure stability and accuracy in measurements. If process 3903 returns a value at or above a preset threshold, process 3905 is allowed to begin, whereby the controller reads sensory values provided by mechanism 225. If the value is below the preset threshold, state 3907 is assumed, whereby the controller recognizes that the battery power is too low for process 3905 to be properly carried out. This information is then sent to the computer via process 3909.

The firmware then calibrates the sensors in process 3911 to normalize the measurements. Each sensor that is in need of adjustments is calibrated one at a time, which is regulated via process 3913. If a sensor is unable to provide calibrated measurements, status 3915 is entered, wherein the controller sends an error report to the computer in process 3917 and terminates. Process 3919 sends a confirmation report to the computer if all sensors in need of calibration do so without error.

Once the report is sent, the microcontroller locks the calibration settings in process 3921, thereby enabling the device to begin reading sensors in process 3923 and sending measurements to the computer in process 3925. In processes 3923 and 3925, the controller enters a stream of communication with the host computer in which ADC is carried out for each sensor and sent to the computer periodically.

If at any time an error occurs during operation of any of the aforementioned processes 3903-3925, processes 3927, 3929 and 3931 act to detect such an error and report it to the computer. Process 3927 detects errors separately from the main program flow. This allows the device to detect various errors in process 3929, and interrupt the main program flow so as to allow process 3931 to send a report of the error to the host computer.

Figure 40:
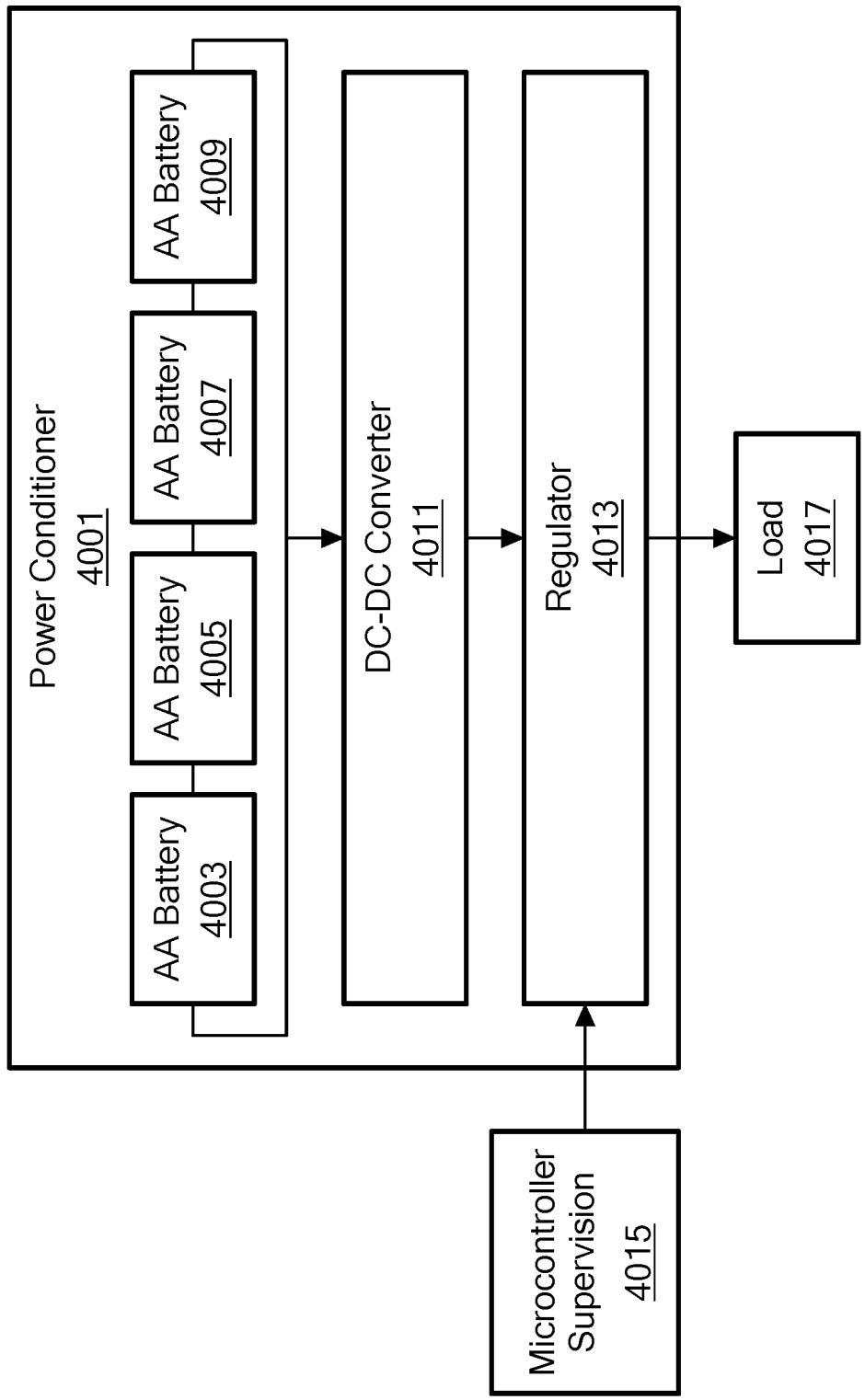
FIG. 40 is block diagram of architecture of a power conditioner associated with the system architecture of FIG.

FIG. 40 schematically represents an architecture of a power conditioner 4001 associated with the system architecture of FIG. 2, in accordance with an embodiment of the present invention, for carrying out the method embodiment of FIG. 1. Four AA batteries 4003, 4005, 4007, and 4009 are connected in series to supply a 6 volt voltage source. This voltage is conditioned in DC-to-DC converter 4011 to supply positive and negative supply rails so as to ensure the stable operational amplifiers used to carry out the method embodiment of FIG. 1. The voltage source level is then reduced in regulator 4013 in accordance with 221 power requirements. This regulation process is monitored by a program executing in the microcontroller 4015 in accordance with processes 3903, 3907, and 3909. The regulated power source is then supplied to the rest of the device, as embodied by the load 4017.

FIG. 41 schematically represents an architecture of a skin conductance sensor pre-filter system 4101 associated with the system architecture of FIG. 2, in accordance with an embodiment of the present invention, for carrying out the method embodiment of FIG. 1. Skin conductance sensor 4103 connects to DAQ board 209, and includes two finger straps 4105 and 4111 for fixing the sensor to fingers of the subject, and two contacts 4107 and 4109 for measuring skin conductance of the subject. Before conditioning the signal, a microcontroller controls the flow of the signal in a process under control of microcontroller 4113 by either enabling or disabling sensor 4103. A high-pass filter 4115 filters the signal from 4103 of high-frequency electrical noise so as to prepare the signal for analog-to-digital conversion by ADC 225. A low-pass filter 4117 filters the signal of DC electrical offset, so as to normalize and prepare the signal for conversion. The signal is then amplified in amplifier 4119 to a range suitable for conversion. A reference voltage 4121 is supplied to the amplification circuitry 4119 so as to provide a baseline to which the signal deviates according to user stimuli. This output signal is then sent to ADC 225 as shown by block 4123.

FIG. 42 schematically represents an architecture of a respiration rate sensor pre-filter system 4201 associated with the system architecture of FIG. 2, in accordance with an embodiment of the present invention, for carrying out the method embodiment of FIG. 1. A breathing rate sensor 4203 connects to DAQ board 209, and includes a chest strap 4205 for fixing the sensor to the subject, and a resistive belt 4207 for measuring the expansion of the subject's chest. Instrumentation amplifier 4213 amplifies the signal from resistive belt 4207. A reference resistance 4209 provides a precision reference to the differential amplifier 4213 to compare to the unknown resistance in the sensor 4203 to produce a signal with optimal resolution and without major DC offset. A microcontroller 4211 controls this resistance so as to calibrate the sensor through the firmware process 3911. A reference voltage 4215 is provided to the amplifier 4213 to provide a baseline to which the signal deviates according to user stimuli. A high-pass filter 4217 then filters the signal from the amplifier 4213 of high-frequency electrical noise so as to prepare the signal for ADC 225. A low-pass filter 4219 filters the signal from the high-pass filter 4217 of DC electrical offset, so as to normalize and prepare the signal for measurements in analog-to-digital conversion. The microcontroller also controls the flow of the signal from the resistive belt 4207 to the amplifier 4213 in a firmware process 4211, in accordance to the methods embodied by FIG. 39. This filtered signal is then sent to the controller for ADC 225 as shown by block 4221.

FIG. 43 schematically represents an architecture of a heart rate sensor system 4301 associated with the system architecture of FIG. 2, in accordance with an embodiment of the present invention, for carrying out the method embodiment of FIG. 1. The heart rate sensor 4303 includes a photodiode 4305 that captures light emanating from an infrared diode 4307. The finger clip 4309 keeps both diodes in fixed relation to the subject's finger while process 4311 controls the electrical current flowing to the infrared diode 4307. The absorbed infrared light is detected by the photodiode 4305, producing a signal that is sent to 4313, where it is filtered of high-frequency noise. This signal is then filtered of DC offset via a low-pass filter 4315. The filtered signal is then amplified in 4317 with a baseline voltage reference 4319 and sent to process 225 to be converted into a digital format as shown by block 4321.

FIG. 44 schematically represents an architecture of a skin temperature sensor system 4401 associated with the system architecture of FIG. 2, in accordance with an embodiment of the present invention, for carrying out the method embodiment of FIG. 1. A temperature sensor 4403 is made of a sensor 4407 which is strapped to the subject via a hand strap 4405. A microcontroller 4409 controls the signal flow from the sensor 4407 via firmware embodied in process 3901. The signal is sent from sensor 4407 to a high-pass filter 4411 and is filtered of any high-frequency noise. This signal is then filtered of any DC-offset in a low-pass filter 4413, after which the signal is amplified in accordance to 221 with a reference voltage 4417 supplying a baseline for which the signal deviates according to user stimuli. This filtered and formatted signal is then sent to ADC 225 as shown by block 4419.

The present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof.

Computer program logic implementing all or part of the functionality previously described herein may be embodied in various forms, including, but in no way limited to, a source code form, a computer executable form, and various intermediate forms (e.g., forms generated by an assembler, compiler, networker, or locator.) Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink wrapped software or a magnetic tape), preloaded with a computer system (e.g., on system ROM or fixed disk), or distributed from a server or electronic bulletin board over the communication system (e.g., the Internet or World Wide Web.)

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL.)

Embodiments of the present invention may be described, without limitation, by the following clauses. While these embodiments have been described in the clauses by process steps, an apparatus comprising a computer with associated display capable of executing the process steps in the clauses below is also included in the present invention. Likewise, a computer program product including computer executable instructions for executing the process steps in the clauses below and stored on a computer readable medium is included within the present invention.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method of improving psychophysiological function of a subject with respect to a stress-inducing activity, using a computer having an output interface, the method comprising:

providing, by the computer to the subject, a profiling segment in which a stress-indicating physiological parameter and a baseline value of the stress-indicating physiological parameter are determined for use in providing a set of training segments; and providing, by the computer to the subject, the set of training segments until the computer determines that a value of the stress-indicating physiological parameter is within a pre-defined range of the baseline value of the parameter, each training segment in the set presenting the subject with one or more visual, audible, or tactile prompts or a combination of such prompts using the output interface, wherein at least one of the training segments simultaneously presents the subject with a stress-inducing prompt while inducing the subject to perform a relaxation-inducing protocol.

2. The method according to claim 1, wherein the stress-indicating physiological parameter is determined in the profiling segment, the method further comprising:

receiving, by the computer, a stream of measured values for each of a plurality of physiological parameters, each value in the stream being measured by a respective sensor coupled to the subject; and selecting, by the computer, as the stress-indicating physiological parameter, the physiological parameter for which the greatest variation of values exists within the respective stream of measured values.

3. The method according to claim 1, wherein the baseline value of the stress-indicating physiological parameter is determined in the profiling segment, the method further comprising:

receiving, by the computer, a stream of measured values for the stress-indicating physiological parameter, each value in the stream being measured by a sensor coupled to the subject; and determining the baseline range of values for the stress-indicating physiological parameter based on the greatest variation of its values.

4. The method according to claim 1, wherein providing the set of training segments comprises:

providing a sequence of training segments selected from the group consisting of those segments that do not present the stress-inducing prompt and those segments that do present the stress-inducing prompt.

5. The method according to claim 1, wherein providing the set of training segments comprises providing a sequence of training segments that do not present the stress-inducing prompt and the sequence comprises, in any order:

a training segment in which the subject is prompted to perform the relaxation-inducing protocol;

a training segment in which the subject is prompted to perform the relaxation-inducing protocol while receiving feedback indicative of the at least one physiological parameter; and a training segment in which the subject receives feedback indicative of the at least one physiological parameter without being prompted to perform the relaxation-inducing protocol.

6. The method according to claim 1, wherein providing the set of training segments comprises providing a sequence of training segments that do present the stress-inducing prompt and the sequence comprises, in any order:

a training segment in which the subject is simultaneously presented with the stress-inducing prompt and induced to perform the relaxation-inducing protocol, while receiving feedback indicative of the at least one physiological parameter;

a training segment in which the subject is presented with the stress-inducing prompt, but not induced to perform the relaxation-inducing protocol, while receiving feedback indicative of the at least one physiological parameter; and a training segment in which the subject is presented with the stress-inducing prompt, but not induced to perform the relaxation-inducing protocol, while not receiving feedback indicative of the at least one physiological parameter.

7. The method according to claim 1, wherein the relaxation-inducing protocol is determined in the profiling segment, the method further comprising:

presenting, by the computer to the subject, a set of relaxation exercises, and, for each relaxation exercise, recording a first set of biological measurements while the subject is performing the relaxation exercise and then recording a second set of biological measurements during a recovery period following performance of the relaxation exercise.

8. A computer program product comprising a tangible non-transitory computer-readable storage medium on which is stores program code that, when executed by a processor of a computer having an output interface, causes the computer to implement a method of improving psychophysiological function of a subject with respect to a stress-inducing activity, the method comprising:

providing, by the computer to the subject, a profiling segment in which a stress-indicating physiological parameter and a baseline value of the stress-indicating physiological parameter are determined for use in providing a set of training segments; and providing, by the computer to the subject, the set of training segments until the computer determines that a value of the stress-indicating physiological parameter is within a pre-defined range of the baseline value of the parameter, each training segment in the set presenting the subject with one or more visual, audible, or tactile prompts or a combination of such prompts using the output interface, wherein at least one of the training segments simultaneously presents the subject with a stress-inducing prompt while inducing the subject to perform a relaxation-inducing protocol.

9. The computer program product according to claim 8, wherein the stress-indicating physiological parameter is determined in the profiling segment, the method further comprising:

receiving, by the computer, a stream of measured values for each of a plurality of physiological parameters, each value in the stream being measured by a respective sensor coupled to the subject; and selecting, by the computer, as the stress-indicating physiological parameter, the physiological parameter for which the greatest variation of values exists within the respective stream of measured values.

10. The computer program product according to claim 8, wherein the baseline value of the stress-indicating physiological parameter is determined in the profiling segment, the method further comprising:

receiving, by the computer, a stream of measured values for the stress-indicating physiological parameter, each value in the stream being measured by a sensor coupled to the subject; and determining the baseline range of values for the stress-indicating physiological parameter based on the greatest variation of its values.

11. The computer program product according to claim 8, wherein providing the set of training segments comprises:

providing a sequence of training segments selected from the group consisting of those segments that do not present the stress-inducing prompt and those segments that do present the stress-inducing prompt.

12. The computer program product according to claim 8, wherein providing the set of training segments comprises providing a sequence of training segments that do not present the stress-inducing prompt and the sequence comprises, in any order:

a training segment in which the subject is prompted to perform the relaxation-inducing protocol;

a training segment in which the subject is prompted to perform the relaxation-inducing protocol while receiving feedback indicative of the at least one physiological parameter; and a training segment in which the subject receives feedback indicative of the at least one physiological parameter without being prompted to perform the relaxation-inducing protocol.

13. The computer program product according to claim 8, wherein providing the set of training segments comprises providing a sequence of training segments that do present the stress-inducing prompt and the sequence comprises, in any order:

a training segment in which the subject is simultaneously presented with the stress-inducing prompt and induced to perform the relaxation-inducing protocol, while receiving feedback indicative of the at least one physiological parameter;

a training segment in which the subject is presented with the stress-inducing prompt, but not induced to perform the relaxation-inducing protocol, while receiving feedback indicative of the at least one physiological parameter; and a training segment in which the subject is presented with the stress-inducing prompt, but not induced to perform the relaxation-inducing protocol, while not receiving feedback indicative of the at least one physiological parameter.

14. The computer program product according to claim 8, wherein the relaxation-inducing protocol is determined in the profiling segment, the method further comprising:

presenting, by the computer to the subject, a set of relaxation exercises, and, for each relaxation exercise, recording a first set of biological measurements while the subject is performing the relaxation exercise and then recording a second set of biological measurements during a recovery period following performance of the relaxation exercise.

15. A device for training a subject to improve psychophysiological function with respect to a stress-inducing activity, the device comprising:

a processor;

at least one sensor input coupled to the processor, the at least one sensor input being connectable to a set of sensors coupled to the subject for measuring at least one physiological parameter of the subject, at least one physiological parameter indicating stress in the subject, wherein the processor is programmed to receive from the sensors a measurement stream that quantifies the at least one stress-indicating physiological parameter;

an output interface coupled to the processor; and a non-transitory storage medium storing program code that, when executed by the processor, causes the processor to implement a method of improving psychophysiological function of a subject with respect to the stress-inducing activity, the method comprising:

providing, by the processor to the subject, a profiling segment in which a stress-indicating physiological parameter and a baseline value of the stress-indicating physiological parameter are determined for use in providing a set of training segments; and providing, by the processor to the subject, the set of training segments until a computer determines that a value of the stress-indicating physiological parameter is within a pre-defined range of the baseline value of the parameter, each training segment in the set presenting the subject with one or more visual, audible, or tactile prompts or a combination of such prompts using the output interface, wherein at least one of the training segments simultaneously presents the subject with a stress-inducing prompt while inducing the subject to perform a relaxation-inducing protocol.

16. The device according to claim 15, wherein the stress-indicating physiological parameters is determined in the profiling segment, the method further comprising:
   receiving, by the processor, a stream of measured values for each of a plurality of physiological parameters, each value in the stream being measured by a respective sensor coupled to the subject; and
   selecting, by the processor, as the stress-indicating physiological parameter, the physiological parameter for which the greatest variation of values exists within the respective stream of measured values.

17. The device according to claim 15, wherein the baseline value of the stress-indicating physiological parameter is determined in the profiling segment, the method further comprising:
   receiving, by the processor, a stream of measured values for the stress-indicating physiological parameter, each value in the stream being measured by a sensor coupled to the subject; and
   determining the baseline range of values for the stress-indicating physiological parameter based on the greatest variation of its values.

18. The device according to claim 15, wherein providing the set of training segments comprises providing a sequence of training segments selected from the group consisting of those segments that do not present the stress-inducing prompt and those segments that do present the stress-inducing prompt.

19. The device according to claim 15, wherein providing the set of training segments comprises providing a sequence of training segments that do not present the stress-inducing prompt and the sequence comprises, in any order:
   a training segment in which the subject is prompted to perform the relaxation-inducing protocol;
   a training segment in which the subject is prompted to perform the relaxation-inducing protocol while receiving feedback indicative of the at least one physiological parameter; and
   a training segment in which the subject receives feedback indicative of the at least one physiological parameter without being prompted to perform the relaxation-inducing protocol.

20. The device according to claim 15, wherein providing the set of training segments comprises providing a sequence of training segments that do present the stress-inducing prompt and the sequence comprises, in any order:
   a training segment in which the subject is simultaneously presented with the stress-inducing prompt and induced to perform the relaxation-inducing protocol, while receiving feedback indicative of the at least one physiological parameter;
   a training segment in which the subject is presented with the stress-inducing prompt, but not induced to perform the relaxation-inducing protocol, while receiving feedback indicative of the at least one physiological parameter; and
   a training segment in which the subject is presented with the stress-inducing prompt, but not induced to perform the relaxation-inducing protocol, while not receiving feedback indicative of the at least one physiological parameter.

21. The device according to claim 15, wherein the relaxation-inducing protocol is determined in the profiling segment, the method further comprising:
   presenting, by the processor to the subject, a set of relaxation exercises, and, for each relaxation exercise, recording a first set of biological measurements while the subject is performing the relaxation exercise and then recording a second set of biological measurements during a recovery period following performance of the relaxation exercise.

* * * * *